US010947320B2

(12) United States Patent
Bilgicer et al.

(10) Patent No.: US 10,947,320 B2
(45) Date of Patent: Mar. 16, 2021

(54) COVALENT HETEROBIVALENT ANTIBODY INHIBITORS AND LIGANDS

(71) Applicant: University of Notre Dame du Lac, South Bend, IN (US)

(72) Inventors: Zihni Basar Bilgicer, South Bend, IN (US); Peter Edward Deak, South Bend, IN (US); Tanyel Kiziltepe Bilgicer, South Bend, IN (US); Michael William Handlogten, South Bend, IN (US); Jonathan Darryl Ashley, South Bend, IN (US)

(73) Assignee: University of Notre Dame du Lac, South Bend, IN (US)

(*) Notice: Subject to any disclaimer, the term of this patent is extended or adjusted under 35 U.S.C. 154(b) by 118 days.

(21) Appl. No.: 16/062,832

(22) PCT Filed: Dec. 19, 2016

(86) PCT No.: PCT/US2016/067588
§ 371 (c)(1),
(2) Date: Jun. 15, 2018

(87) PCT Pub. No.: WO2017/106859
PCT Pub. Date: Jun. 22, 2017

(65) Prior Publication Data
US 2019/0375857 A1     Dec. 12, 2019

Related U.S. Application Data

(60) Provisional application No. 62/269,355, filed on Dec. 18, 2015.

(51) Int. Cl.
| A61K 9/48 | (2006.01) |
| C07K 7/08 | (2006.01) |
| C07K 14/415 | (2006.01) |
| C07K 14/385 | (2006.01) |
| A61P 37/08 | (2006.01) |
| C07K 16/46 | (2006.01) |
| A61K 47/62 | (2017.01) |
| A61K 47/54 | (2017.01) |
| A61K 9/127 | (2006.01) |
| A61K 38/05 | (2006.01) |
| A61K 38/07 | (2006.01) |
| A61K 47/02 | (2006.01) |
| A61K 47/10 | (2017.01) |

(52) U.S. Cl.
CPC ............. *C07K 16/46* (2013.01); *A61K 9/127* (2013.01); *A61K 38/05* (2013.01); *A61K 38/07* (2013.01); *A61K 47/02* (2013.01); *A61K 47/10* (2013.01); *A61K 47/54* (2017.08); *A61K 47/62* (2017.08)

(58) Field of Classification Search
CPC .. A61K 9/4866; A61K 9/0014; A61K 9/0019; A61K 9/0073; A61K 9/2018; A61K 9/2027; A61K 9/2054; A61K 9/2059; A61K 9/4858; A61K 35/00; A61K 38/00; A61K 39/35; A61K 38/07; C07K 7/00; C07K 7/06; C07K 7/08; C07K 17/00; C07K 14/485; C07K 14/415; C07K 14/385; C07K 11/00; C07K 9/01; C07K 9/00; C07K 16/46; A61P 37/08
See application file for complete search history.

(56) References Cited

U.S. PATENT DOCUMENTS 8,349,333 B2    1/2013   Wang et al.

FOREIGN PATENT DOCUMENTS

| EP | 1846031 A1 | 10/2007 |
| WO | 2006092908 A1 | 9/2006 |
| WO | 2012088290 A3 | 9/2012 |
| WO | 2014121291 A2 | 8/2014 |
| WO | 2014152801 A1 | 9/2014 |

OTHER PUBLICATIONS

Greenspan et al., Nature Biotechnology 17: 936-937 (Year: 1999).*
Dodson et al., Nature 450: 176-177 (Year: 2007).*
Albrecht et al., "Relevance of IgE Binding to Short Peptides for the Allergenic Activity of Food Allergens," J Allergy Clin Immunol., 124(2):328-336, Aug. 2009.
Alves et al., "Conjugation of a Reactive Thiol at the Nucleotide Binding Site for Site-Specific Antibody Functionalization," Bioconjug Chem., 25(7):1198-1202, Jul. 2014.
Alves et al., "Oriented Antibody Immobilization by Site-specific UV Photocrosslinking of Biotin at the Conserved Nucleotide Binding Site for Enhanced Antigen Detection," Biosens Bioelectron., 49:387-393, Nov. 2013.
Alves et al., "Small-Molecule-Based Affinity Chromatography Method for Antibody Purification via Nucleotide Binding Site Targeting," Anal Chem., 84(18):7721-7728, Sep. 2012.
(Continued)

*Primary Examiner* — Phuong Huynh
(74) *Attorney, Agent, or Firm* — Haukaas Fortius PLLC; Michael H. Haukaas

(57) ABSTRACT

The invention provides a strategy for site specific covalent modification of antibodies using a specialized targeting covalent heterobivalent ligand (cHBL), and corresponding design for a covalent heterobivalent inhibitor (cHBI) that can be used to prevent Immunoglobulin E (IgE) mediated allergic reactions triggered by drug molecules, according to one embodiment. These molecules contain four important components: (1) an IgE antigen binding site (ABS) ligand that can be a mimotope for the allergen protein, a small molecule, or a peptidomimetic, (2) an appropriate linker, which can be any flexible or rigid chemical linker, providing spacing between the ABS binder and the other moieties, (3) a nucleotide binding site (NBS) ligand, and (4) a reactive moiety to form a covalent link with an amino acid side chain of target IgE antibodies.

12 Claims, 52 Drawing Sheets

Specification includes a Sequence Listing.

(56) References Cited

OTHER PUBLICATIONS

Bernard et al., "Allergenicity of Peanut Component Ara h 2: Contribution of Conformational Versus Linear Hydroxyproline-Containing Epitopes," J Allergy Clin Immunol., 135(5):1267-1274, May 2015.

Cox et al., "Allergen Immunotherapy Practice in the United States: Guidelines, Measures, and Outcomes," Ann Allergy Asthma Immunol., 107(4):289-299, Oct. 2011.

Deak et al., "Nanoallergens: A Multivalent Platform for Studying and Evaluating Potency of Allergen Epitopes in Cellular Degranulation," Exp Biol Med (Maywood), 241(9):996-1006, May 2016.

Handlogten et al., "A Heterobivalent Ligand Inhibits Mast Cell Degranulation via Selective Inhibition of Allergen-IgE Interactions In Vivo," J Immunol., 192(5):2035-2041, Mar. 2014.

Handlogten et al., "Design of a Heterobivalent Ligand to Inhibit IgE Clustering on Mast Cells," Chem Biol.,18(9):1179-1188, Sep. 2011.

Handlogten et al., "Design of a Heterotetravalent Synthetic Allergen that Reflects Epitope Heterogeneity and IgE Antibody Variability to Study Mast Cell Degranulation," Biochem J., 449(1):91-99, Jan. 2013.

International Search Report and Written Opinion of the ISA/US dated Mar. 9, 2017 in International Application No. PCT/US2016/067588; 10pgs.

Kurosu et al., "Efficient Synthesis of Tertiary Amines from Secondary Amines," Tetrahedron Letters, 47(28):4871-4875, Jul. 2006.

Levine et al., "Studies on the Mechanism of the Formation of the Penicillin Antigen," J Exp Med., 114:875-904, Dec. 1961.

Meng et al., "PEGylation of Human Serum Albumin: Reaction of PEG-phenyl-isothiocyanate with Protein," Bioconjugate Chem., 19(7):1352-1360, Jun. 2008.

Mueller et al., "Ara h 2: Crystal Structure and IgE Binding Distinguish Two Subpopulations of Peanut Allergic Patients by Epitope Diversity," Allergy, 66(7):878-885, Jul. 2011.

Munch et al., "A New Efficient Synthesis of Isothiocyanates from Amines Using di-tert-butyl Dicarbonate," Tetrahedron Lett., 49(19):3117-3119, May 2008.

Mustafaoglu et al., "Oriented Immobilization of Fab Fragments by Site-Specific Biotinylation at the Conserved Nucleotide Binding Site for Enhanced Antigen Detection," Langmuir, 31(35):9728-9736, Sep. 2015.

Otsu et al., "Epitope Analysis of Ara h 2 and Ara h 6: Characteristic Patterns of IgE-binding Fingerprints Among Individuals with Similar Clinical Histories," Clin Exp Allergy, 45(2):471-484, Feb. 2015.

Peter et al., "The T-cell Receptor Zeta-Chain Contains a GTP/GDP Binding-Site," EMBO J., 11(3):933-941, Mar. 1992.

Rajagopalan et al., "Novel Unconventional Binding Site in the Variable Region of Immunoglobulins," PNAS USA, 93(12):6019-6024, Jun. 1996.

Sampson et al., "A Phase II, Randomized, Double-Blind, Parallel-Group, Placebo-Controlled Oral Food Challenge Trial of Xolair (Omalizumab) in Peanut Allergy," J Allergy Clin Immunol., 127(5):1309-U338, May 2011.

Stanley et al., "Identification and Mutational Analysis of the Immunodominant IgE-Binding Epitopes of the Major Peanut Allergen Ara h 2," Arch Biochem Biophys., 342(2):244-253, Jun. 1997.

University of Notre Dame du Lac, Chemical and Biomolecular Engineering Graduate Student Organization (CBEGSO) Poster "Inhibitors for Allergic Reactions to Drugs and Other Small Molecules," Nov. 2016, 1 pg.

* cited by examiner

A. 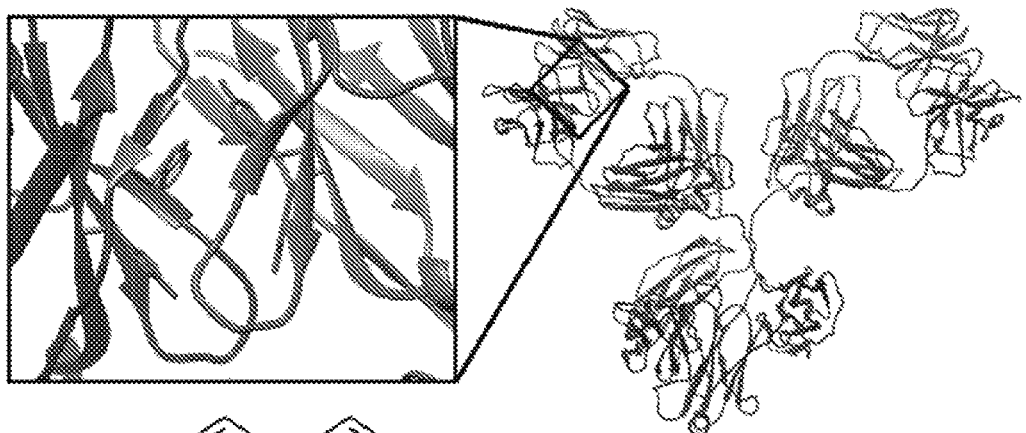
B. 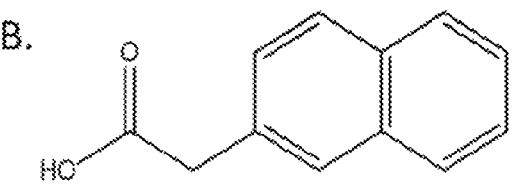
Naphthaleneacetic acid
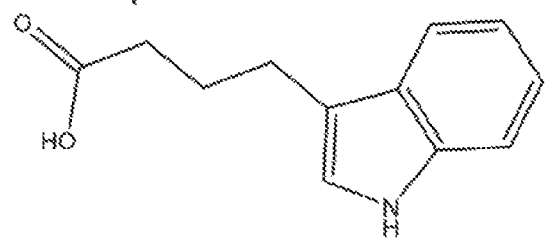
indole-3-butyric acid
C. 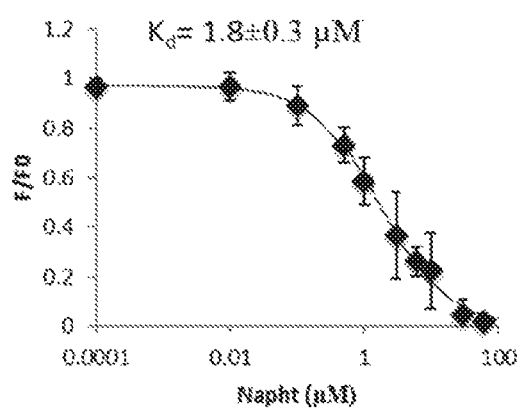
D. 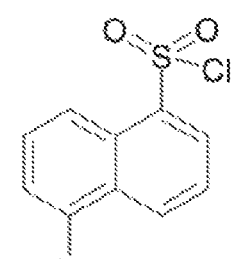
Dansyl
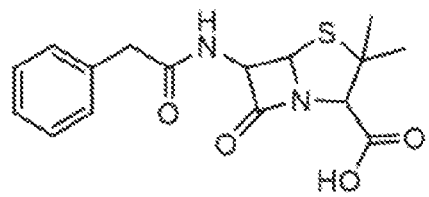
Penicillin G
*Fig. 1A-1D*

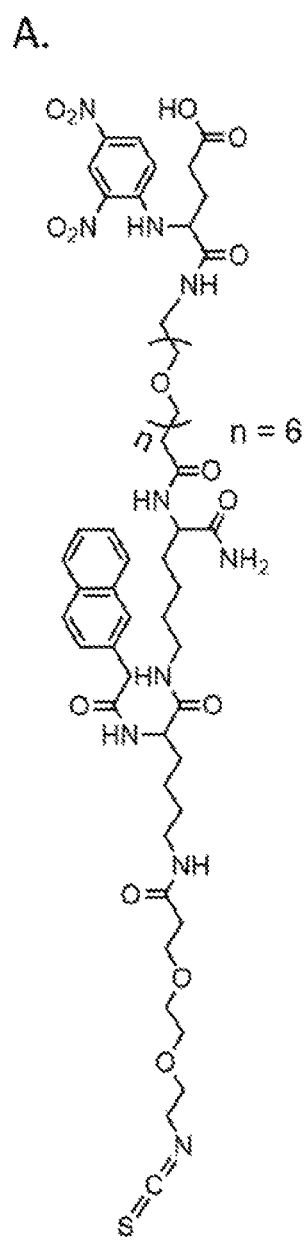
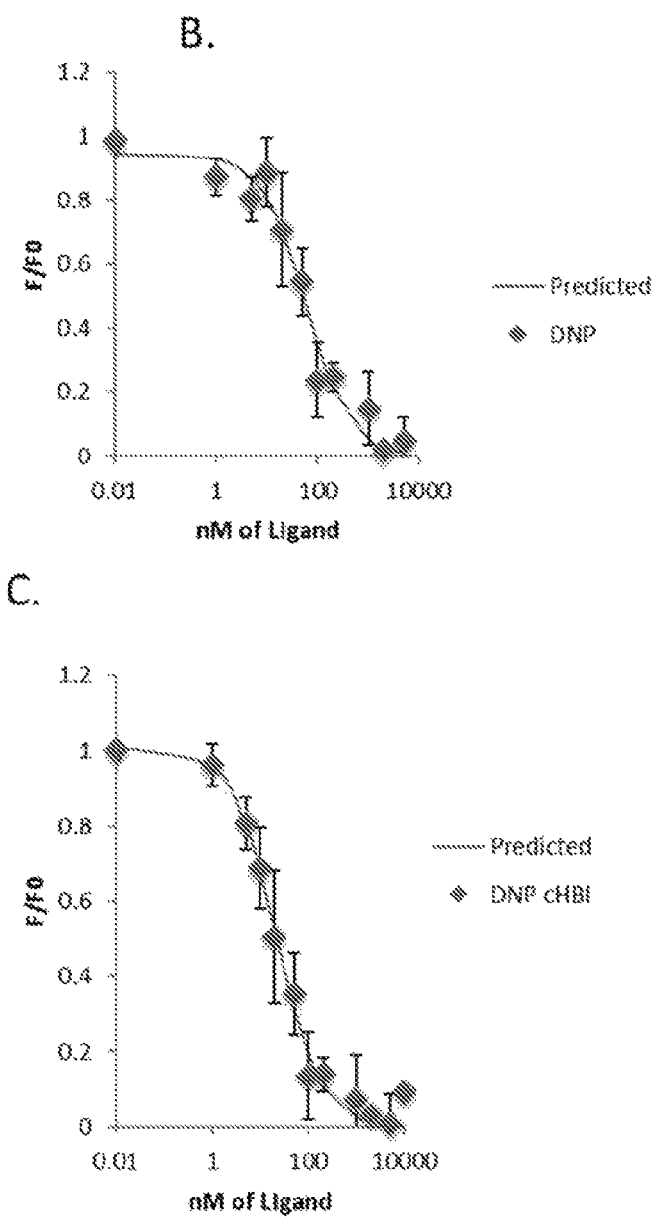
Fig. 10A-10C

Fig. 45

COVALENT HETEROBIVALENT ANTIBODY INHIBITORS AND LIGANDS

RELATED APPLICATIONS

This application is a National Stage filing under 35 U.S.C. § 371 of International Application No. PCT/US2016/067588 filed Dec. 19, 2016, which claims priority under 35 U.S.C. § 119(e) to U.S. Provisional Patent Application No. 62/269,355, filed Dec. 18, 2015, which applications are incorporated herein by reference.

GOVERNMENT SUPPORT

This invention was made with government support under Grant No. R01 AI108884, R03 AI108884, and R56 AI108884 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Jul. 28, 2020, is named 501_051US1_SL.txt and is 13,557 bytes in size.

BACKGROUND OF THE INVENTION

Antibodies are a major target of contemporary scientific research due to their wide variety of applications in immunology, therapeutics, diagnostics and biosensing. Thus, there is also a great need for adequate tools to study and analyze antibodies both in vitro and in vivo. With the advent of genetically engineered antibodies and commercial monoclonal antibody production, there has been an increasing interest in antibody drug conjugates (ADCs) and site specific tags of antibodies for cancer and other disease treatment as well as for biosensing applications. Likewise, for hypersensitivity reactions and many autoimmune disorders that produce autoantibodies, antibodies are a primary target of potential therapeutics.

The most challenging aspect of making specific ADCs is ensuring that drug conjugation occurs at a specific location. Most attempts to perform site specific modification of antibodies occur ex vivo and typically require genetic modification of the germ line of an organism producing monoclonal antibodies (mAbs). Though addition of an unnatural amino acid or other specific tag (such as His tags), several studies have demonstrated specific attachment to a region of mAbs. However, these require complex techniques and sometimes require manipulation of antibody structure that may prove detrimental to overall antibody activity. Furthermore, and more importantly, these techniques require controlled conditions and purified mAbs to ensure that site specific modification is occurring, which is not always feasible or practical.

In addition, drug allergies are a type of adverse drug reaction that afflicts over 2 million people per year in the US. These allergies are particularly dangerous because unlike other adverse drug reactions, they are unpredictable and can have a wide variety of symptoms and triggers, and these reactions occur to very commonly used drugs such as sulfa drugs and antibiotics. In particular, immediate immunoglobulin E (IgE) mediated hypersensitivity reactions caused by drugs can be the most life threatening because they cause rapid and severe anaphylaxis reactions. Furthermore, over half of allergy fatalities are due to anaphylaxis reactions to drugs. Currently, the only FDA approved treatments for drug allergies are post-reaction treatments such as antihistamines or corticosteroids, both of which have not shown dependable prevention of anaphylaxis responses, likely due to the rapid onset of anaphylaxis. The only treatment for anaphylaxis reactions to drugs is treatment with epinephrine, which only delays onset of the symptoms for several minutes so that the patient can reach proper medical care. Given the prevalence of these reactions and the lack of adequate treatments, there is a need for development of preventative and/or more rapidly acting treatments for drug reactions.

The allergic reaction (type I hypersensitivity) is a complex immune reaction to innocuous compounds such as food, environmental factors and drugs. These reactions can cause symptoms from harmless skin irritation to a life-threatening anaphylaxis reaction. The characteristic cellular process of type I hypersensitivity is the release of inflammatory cytokines such as histamine from mast cells and basophils after exposure to an allergen, also known as a degranulation response.

Molecules for the treatment of allergy symptoms include antihistamine drugs such as Diphenhydramine, Cetirizine, and others which are agonists to histamine receptors. Also, there are mast cell stabilizer drugs such as cromolyn which bind calcium channels on mast cells and help to prevent some degranulation events. Finally, there are steroid drugs designed to non-specifically suppress immune system function and therefore allergic reactions. However, these treatments are for post-reaction treatment and/or chronic allergy symptom management and do no prevent degranulation events from occurring.

There have also been some preventative treatments using anti-IgE antibodies, specifically using a monoclonal antibody called Omalizumab to bind to free IgE in patient sera and prevent them from priming mast cells. However, this treatment does not affect IgE's already bound to mast cells and does not prevent mast cells from degranulating. Instead this treatment is more focused on chronic autoimmune conditions with high levels of IgE in patient sera. Finally, it is also a significantly costly treatment.

The most common form of long term preventative allergy treatment is the called immunosuppressive therapy. In this therapy, small doses of antigens are given with adjuvants to modulate the immune system's response to the antigen from IgE mediated to T cell mediated. This has drawbacks in that the treatment takes place over the course of months and cannot be used with highly allergic individuals at the risk of triggering anaphylactic reactions.

There have been attempts to competitively inhibit allergen reactive IgE antibodies by genetic engineering to place a vector coding an allergy reactive peptide into cells and then the cells generated the competitive inhibitor (U.S. Pat. No. 8,349,333 B2). This approach appears to be for scientific research purposes and has limited, if any, clinical applications.

To solve the described problems, a substance is needed that can effectively prevent degranulation responses to specific antigens and thus inhibit allergic reactions by covalent heterobivalent inhibition (cHBI) of allergic reactions to food, environmental factors and drugs. Such cHBI substance could be used i) preemptively as a preventative measure by allergy patients who will be in an unknown environment (in situations such as public transportation or air travel, or eating at a restaurant, etc.), ii) as a post-reaction emergency treatment to prevent or stop proliferation of the anaphylactic reaction, or iii) as a treatment to be used in combination with allergy immunotherapy methods. Selective and site specific covalent antibody modification techniques would be particularly useful both for laboratory use and for potential therapeutics.

SUMMARY

In this disclosure, we describe a strategy for a) site specific covalent modification of antibodies using specialized targeting molecules referred to as covalent heterobivalent ligands (cHBLs), and b) the synthesis and in vitro and in vivo characterization of corresponding designs for a covalent heterobivalent inhibitor (cHBI) that can be used to prevent Immunoglobulin E (IgE) mediated allergic reactions triggered by drug molecules.

A covalent heterobivalent inhibitor compounds or a cocktail of such compounds, specifically bind and covalently react with allergen reactive immunoglobulin E (IgE) antibody molecules, deactivating and rendering them incapable of triggering a degranulation response to a specific allergen by permanently blocking their antigen binding site (ABS). Given that mast cell and basophil degranulation responses are primarily triggered by the crosslinking of IgE molecules, inhibition of IgE-allergen binding interaction results in the inhibition of the allergic reaction. The cHBI molecules covalently bind to an amino acid side chain on the IgE molecule near the antigen binding site, thereby tethering the inhibitor molecule to the IgE and increasing its effective concentration. This increased effective concentration competitively inhibits any allergen from binding and crosslinking the IgE antibodies, preventing mast cell and basophil degranulation and consequentially the allergic reaction for a specific allergen.

The antibody ligands and allergy inhibitors described here are molecules that contains four critical covalent components: moieties. Each moiety can be independently modified and optimized for the complete inhibition of a wide range of allergy-inducing compounds. These moieties are: (1) an IgE ABS ligand which can be a mimotope for the allergen protein, a small molecule, or any peptido-mimetic, (2) an appropriate linker, which can be any flexible or rigid chemical linker, providing spacing between the ABS binder and the other moieties, (3) a nucleotide binding site (NBS) ligand, and (4) a reactive moiety to form a covalent link with an amino acid side chain of target IgE antibodies.

Embodiments of an antibody inhibitor or an antibody ligand include Formula I:

$$TM-\underset{|}{S^1}-FG \quad (I)$$
$$TL$$

wherein

TM is a targeting moiety for an antigen binding site (ABS) wherein the targeting moiety comprises a) a mimotope of an allergen protein epitope peptide sequence, b) a peptidomimetic, or c) a small molecule hapten, each which have a selective electrostatic affinity for the ABS of an immunoglobulin;

TL is a targeting ligand for a conserved nucleotide binding site (NBS) of the immunoglobulin wherein the targeting ligand has a selective electrostatic affinity for the NBS located proximal to the ABS and between the heavy chain and light chain of the immunoglobulin;

FG is a reactive functional group capable of forming a site-directed covalent bond to the amine moiety of an amino acid proximal to the NBS of an allergen reactive immunoglobulin; and $S^1$ is a variable length spacer comprising oligomers of ethylene glycol, amino acids, saccharides, hydrocarbons, fluorinated hydrocarbons, or combination thereof, wherein the spacer is conjugated by one or more lysine moieties and one or more amide bonds to TM, TL, and FG;

wherein when the antibody inhibitor bivalently binds to both the ABS and the NBS, the effective concentration of the reactive functional group (FG) near the amino acid of the immunoglobulin increases to irreversibly inhibit the immunoglobulin by the site-directed covalent bond formed by the inhibitor.

Another embodiment of an antibody inhibitor or an antibody ligand is represented by Formula II:

$$\underset{|}{S^2}-TM-\underset{|}{S^1}-FG \quad (II)$$
$$TG \qquad TL$$

wherein

TM is a targeting moiety for an antigen binding site (ABS) wherein the targeting moiety comprises a) a mimotope of an allergen protein epitope peptide sequence, b) a peptidomimetic, or c) a small molecule hapten, each which have a selective electrostatic affinity for the ABS of an immunoglobulin;

TL is a targeting ligand for a conserved nucleotide binding site (NBS) of the immunoglobulin wherein the targeting ligand has a selective electrostatic affinity for the NBS located proximal to the ABS and between the heavy chain and light chain of the immunoglobulin;

FG is a reactive functional group capable of forming a site-directed covalent bond to the amine moiety of an amino acid proximal to the NBS of an allergen reactive immunoglobulin;

$S^1$ is a variable length spacer comprising one or more variable length ethylene glycol ($EG^1$) spacers and one or more lysine ($K^1$) spacers wherein each $EG^1$ spacer and each $K^1$ spacer is linked by one or more amide bonds;

$S^2$ comprises a variable length ethylene glycol ($EG^2$) spacer and a lysine ($K^2$) spacer linked by an amide bond; and TG is a tag comprising a chromophore or a fluorophore;

wherein the ABS targeting moiety (TM), the NBS targeting ligand (TL), and the reactive functional group (FG) are conjugated to $S^1$, and TM is further conjugated to a tag (TG) by a second spacer $S^2$, wherein when the antibody inhibitor bivalently binds to both the ABS and the NBS, the effective concentration of the reactive functional group (FG) near the amino acid of the immunoglobulin increases to irreversibly inhibit the immunoglobulin by the site-directed covalent bond formed by the inhibitor, and the irreversibly inhibited immunoglobulin is tagged by the chromophore or the fluorophore.

Yet another embodiment of an antibody inhibitor or antibody ligand is represented by Formula III:

$$\begin{array}{c} \text{FG} \\ | \\ \text{EG}^2 {-} \overset{K^2}{{-}} \text{TM} {-} \overset{EG^1}{{-}} \overset{K^1}{{-}} \overset{EG^1}{{-}} \\ | \\ \text{TG} \quad\quad\quad \overset{EG^2}{{-}} \\ \quad\quad\quad\quad \text{TL} \end{array} \quad\quad (\text{III})$$

wherein

TM is a targeting moiety for an antigen binding site (ABS) wherein the targeting moiety comprises a) a mimotope of an allergen protein epitope peptide sequence, b) a peptidomimetic, or c) a small molecule hapten, each which have a selective electrostatic affinity for the ABS of an immunoglobulin;

TL is an optional targeting ligand for a conserved nucleotide binding site (NBS) of the immunoglobulin wherein the targeting ligand has a selective electrostatic affinity for the NBS located proximal to the ABS and between the heavy chain and light chain of the immunoglobulin;

FG is an optional reactive functional group capable of forming a site-directed covalent bond to the amine moiety of an amino acid proximal to the NBS of an allergen reactive immunoglobulin;

wherein the inhibitor comprises at least one of TL or FG;

$EG^1$ is a variable length spacer comprising one or more spacers of the formula —$(CH_2—X—CH_2CH_2—X—CH_2)_y$— wherein the —$(CH_2—X—CH_2CH_2—X—CH_2)_y$— spacer is linked to one or more $K^1$ spacers;

y is 1 to 12;

X is O or NR wherein R is H or ($C_1$-$C_4$) alkyl;

$K^1$ is a spacer comprising one or more lysine moieties;

$EG^2$ is an optional variable length spacer comprising the formula —$(CH_2—X—CH_2CH_2—X—CH_2)_y$—;

$K^2$ is an optional spacer comprising a lysine moiety;

wherein the spacers $EG^1$, $EG^2$, $K^1$, $K^2$, and —$(CH_2—X—CH_2CH_2—X—CH_2)_y$— are linked by one or more amide bonds; and TG is an optional tag comprising a chromophore or a fluorophore;

wherein the ABS targeting moiety (TM), the NBS targeting ligand (TL), and the reactive functional group (FG) are conjugated to $K^1$, $EG^1$ and $EG^2$, and TM is further conjugated to an optional tag (TG) by $K^2$ and $EG^2$, wherein when the antibody inhibitor bivalently binds to both the ABS and the NBS, the effective concentration of the reactive functional group (FG) near the amino acid of the immunoglobulin increases to irreversibly inhibit the immunoglobulin by the site-directed covalent bond formed by the inhibitor, and the irreversibly inhibited immunoglobulin is tagged by the chromophore or the fluorophore when the inhibitor contains TG.

The cHBI incorporates all four of these moieties into a single molecule to selectively form covalent bonds with allergen reactive IgEs. For our example, in the proof of principle experiments, we chose to synthesize the ABS ligand either as a peptide mimotope (in the case of Ara h 2 inhibitors) or a small molecule (such as DNP or penicillin). We designed the cHBI molecule to form a covalent bond with the amine group on a lysine residue that is situated in proximity to the NBS only on allergen reactive IgE's. The NBS is a well conserved binding pocket located between the light and heavy chain on the antigen binding region of all Ig's (FIG. 1). We have also identified two compounds, indole-3-butyric acid (IBA) and 2-Naphtheleneacetic acid (Napht) that have a moderate affinity for the NBS site and these were used in the example molecules. By studying crystal structures of several Ig's, we demonstrate that there are lysine residues near the NBS pocket which are can be covalently bound (FIG. 2). We chose the use of isothiocyanate (ITC) group to facilitate this covalent bound formation. ITC groups form covalent reactions with primary amines and in physiological pH's, this reaction is rather slow, which is ideal for selective bond formation because it limits the number of non-specific covalent interactions. By simultaneously targeting the ABS and NBS of an allergen specific IgE, we selectively increase the likelihood of forming a covalent bond with a lysine residue that is situated near the NBS and thereby inhibiting degranulation reactions. To optimize these interactions, we chose a flexible ethylene glycol (EG) linker to link the various moieties. A schematic is shown in FIG. 3.

Although there was a clear enhancement in our ability to inhibit the degranulation response using the NBS ligand in the design, we have also observed that in certain examples the inhibition was still accomplished at an acceptable rate when the NBS ligand was not incorporated in the design (hence the inhibitor molecule was composed of only the 3 moieties out of the 4 we had earlier described). Therefore, in certain cases, it is plausible to use only the 3 components of the inhibitor (ABS ligand, linker, and reactive moiety) to achieve similar results.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

FIGS. 1A-1D. Location of the nucleotide binding site (NBS) and chemical structures of two small molecules specific for the NBS. Light chain is colored in purple and heavy chain is colored in green. A crystal structure of a mouse IgG (PDB: 1IGY) demonstrating the location of the NBS between the heavy chain (in blue) and light chain (in red) shown in A. Tryptophan residue is colored green while tryosines are labeled purple. Naphthaleneacetic acid, a NBS ligand used in this study, is given in B. A fluorescence quenching experiment demonstrating binding between a DNP labeled naphthalene molecule and $IgE^{dansyl}$ shown in C. The chemical structures of the haptens (dansyl and Benzyl Penicillin) used in this study in D.

FIG. 10A-10C. Schematic of DNP cHBI (A) and fluorescence quenching binding data for SPE-7 with DNP (Kd=58.3 nM) (B) or DNP cHBI (Kd=21.5 nM) (C).

FIG. 45. Ara h 2 and Ara h 6 epitopes $EC_{50}$ values to 2% loaded nanoallergens with four patient sera.

DETAILED DESCRIPTION

Figures 2A, 2B, 2C, 2D:
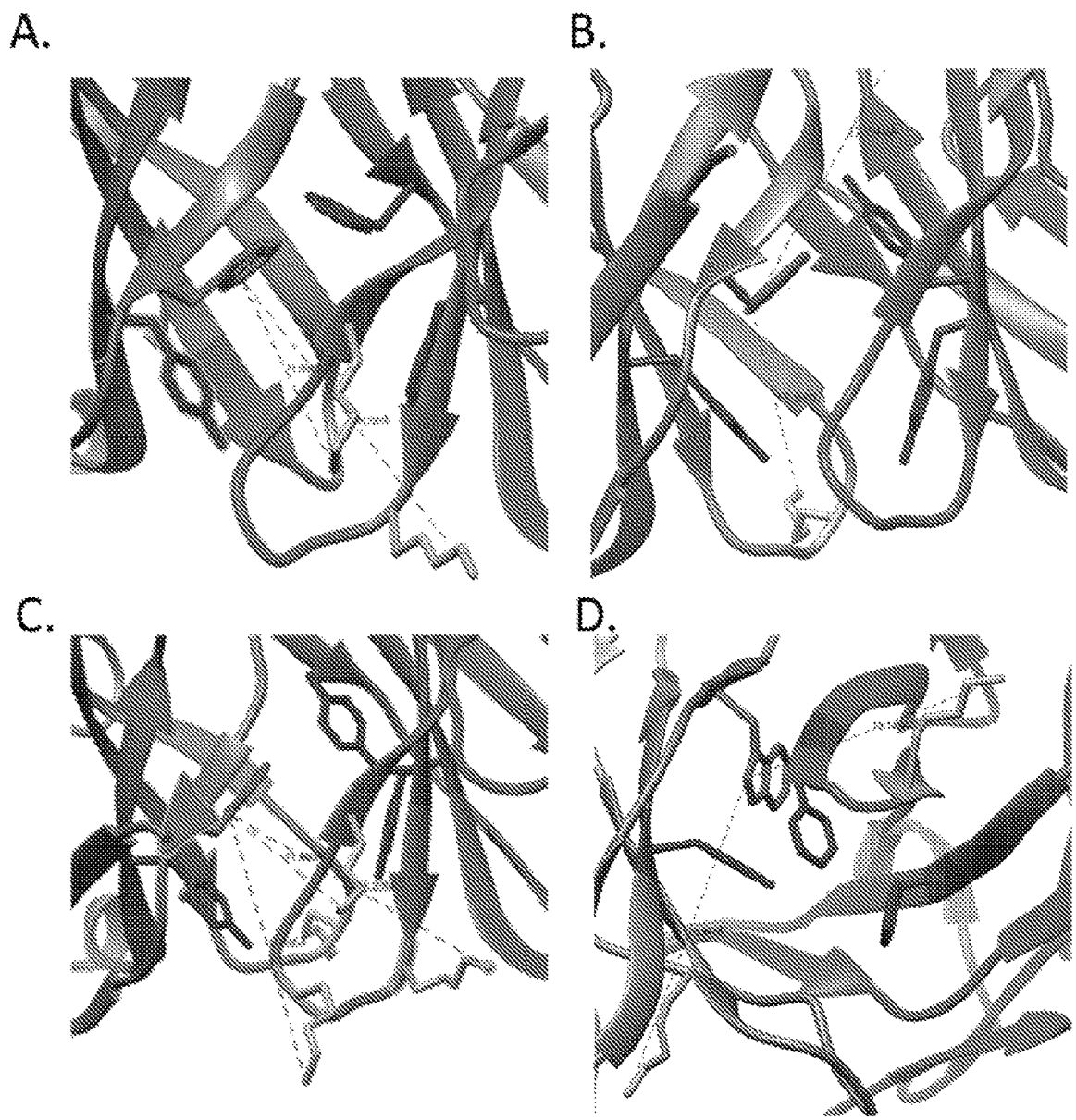
FIG. 2A-2D. NBS sites of various Ig molecules with accessible lysines near the NBS site in orange with distances from tryptophan in binding pocket. (A) Rituximab (11 Å, 16.7 Å), (B) Cetuximab (17 Å, 15.8 Å), (C) Trastuzumab (11.1 Å, 15.5 Å, and 13.5 Å) and (D) SPE-7 (Anti DNP) (13.1 Å, 15.4 Å).

Our strategy for site specific conjugation of monoclonal antibodies (mAbs) rely upon binding to a conserved binding site on immunoglobulins called the nucleotide binding site (NBS) that was initially discovered by Rajagopalan et al. (*Proc Natl Acad Sci USA*. 1996; 93(12): 6019-6024). The NBS is a hydrophobic binding pocket that is located proximal to the antigen binding site (ABS) between the light and heavy chains on the antigen binding fragment (Fab) region of immunoglobulins. We have identified a pair of ind Definitions The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit. For example, one or more substituents on a phenyl ring refers to one to five, or one to four, for example if the phenyl ring is disubstituted.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements. When values are expressed as approximations, by use of the antecedent "about," it will be understood that the particular value without the modifier "about" also forms a further aspect.

The terms "about" and "approximately" are used interchangeably. Both terms can refer to a variation of ±5%, ±10%, ±20%, or ±25% of the value specified. For example, "about 50" percent can in some embodiments carry a variation from 45 to 55 percent, or as otherwise defined by a particular claim. For integer ranges, the term "about" can include one or two integers greater than and/or less than a recited integer at each end of the range. Unless indicated otherwise herein, the terms "about" and "approximately" are intended to include values, e.g., weight percentages, proximate to the recited range that are equivalent in terms of the functionality of the individual ingredient, composition, or embodiment. The terms "about" and "approximately" can also modify the end-points of a recited range as discussed above in this paragraph.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. It is therefore understood that each unit between two particular units are also disclosed. For example, if 10 to 15 is disclosed, then 11, 12, 13, and 14 are also disclosed, individually, and as part of a range. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents. It will be further understood that the endpoints of each of the ranges are significant both in relation to the other endpoint, and independently of the other endpoint.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to treat a disease, disorder, and/or condition, or to bring about a recited effect. For example, an effective amount can be an amount effective to reduce the progression or severity of the condition or symptoms being treated. Determination of a therapeutically effective amount is well within the capacity of persons skilled in the art, especially in light of the detailed disclosure provided herein. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect.

The terms "treating", "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" can extend to prophylaxis and can include prevent, prevention, preventing, lowering, stopping or reversing the progression or severity of the condition or symptoms being treated. As such, the term "treatment" can include medical, therapeutic, and/or prophylactic administration, as appropriate.

An "effective amount" can also refer to an amount effective to bring about a recited effect, such as an amount necessary to form products in a reaction mixture. Determination of an effective amount is typically within the capacity of persons skilled in the art, especially in light of the detailed disclosure provided herein. The term "effective amount" is intended to include an amount of a compound or reagent described herein, or an amount of a combination of compounds or reagents described herein, e.g., that is effective to form products in a reaction mixture. Thus, an "effective amount" generally means an amount that provides the desired effect.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

The term "substantially" as used herein, is a broad term and is used in its ordinary sense, including, without limitation, being largely but not necessarily wholly that which is specified.

The term "proximal" refers the distance from the center of the nucleotide binding site (NBS) to the antigen binding site (ABS) or to the lysine moiety which reacts to form a covalent bond with a functional group (FG) on the antibody inhibitor or the antibody ligand. The proximal distance is less than about 50 angstroms (Å), less than about 40 Å, less than about 30 Å, less than about 20 Å, less than about 10 Å, or less than about 5 Å. The proximal distance can also be in a range between about 5 Å to about 50 Å, a range between about 10 Å to about 40 Å, or a range between about 25 Å to about 35 Å.

The term "alkyl" refers to a branched or unbranched hydrocarbon having, for example, from 1-20 carbon atoms, and often 1-12, 1-10, 1-8, 1-6, or 1-4 carbon atoms. Examples include, but are not limited to, methyl, ethyl, 1-propyl, 2-propyl (iso-propyl), 1-butyl, 2-methyl-1-propyl (isobutyl), 2-butyl (sec-butyl), 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or substituted, for example, with a substituent described below. The alkyl can also be optionally partially or fully unsaturated. As such, the recitation of an alkyl group can include both alkenyl and alkynyl groups. The alkyl can be a monovalent hydrocarbon radical, as described and exemplified above, or it can be a divalent hydrocarbon radical (i.e., an alkylene).

The term "substituted" indicates that one or more hydrogen atoms on the group indicated in the expression using "substituted" is replaced with a "substituent". The number referred to by 'one or more' can be apparent from the moiety on which the substituents reside. For example, one or more can refer to, e.g., 1, 2, 3, 4, 5, or 6; in some embodiments 1, 2, or 3; and in other embodiments 1 or 2, and if the substituent is an oxo group, two hydrogen atoms are replaced by the presence of the substituent. The substituent can be one of a selection of indicated groups, or it can be a suitable group recited below or known to those of skill in the art, provided that the substituted atom's normal valency is not exceeded, and that the substitution results in a stable compound. Suitable substituent groups include, e.g., alkyl, alkenyl (e.g., vinyl, or allyl), alkynyl, alkoxy, halo, haloalkyl, hydroxy, hydroxyalkyl, aryl, aroyl, (aryl)alkyl (e.g., benzyl or phenylethyl), heteroaryl, heterocycle, cycloalkyl, alkanoyl, alkoxycarbonyl, alkylcarbonyloxy, amino, alkylamino, dialkylamino, trifluoromethyl, trifluoromethoxy, trifluoromethylthio, difluoromethyl, acylamino, nitro, carboxy, carboxyalkyl, keto, thioxo, alkylthio, alkylsulfinyl, alkylsulfonyl, arylsulfinyl, arylsulfonyl, heteroarylsulfinyl, heteroarylsulfonyl, heterocyclesulfinyl, heterocyclesulfonyl, phosphate, sulfate, hydroxyl amine, hydroxyl (alkyl)amine, and cyano, as well as the moieties illustrated in the schemes and Figures of this disclosure; or combinations thereof. Additionally, suitable substituent groups can be, e.g., —X, —R, —O$^-$, —OR, —SR, —S$^-$, —NR$_2$, —NR$_3$, =NR, —CX$_3$, —CN, —OCN, —SCN, —N=C=O, —NCS, —NO, —NO$_2$, =N$_2$, —N$_3$, —NC(=O)R, —C(=O)R, —C(=O)NRR, —S(=O)$_2$O$^-$, —S(=O)$_2$OH, —S(=O)$_2$R, —OS(=O)$_2$OR, —S(=O)$_2$NR, —S(=O)R, —OP(=O) (OR)$_2$, —P(=O)(OR)$_2$, —OP(=O)(OH)(OR), —P(=O) (OH)(OR), —P(=O)(O$^-$)$_2$, —P(=O)(OH)$_2$, —C(=O)R, —C(=O)X, —C(S)R, —C(O)OR, —C(O)O$^-$, —C(S)OR, —C(O)SR, —C(S)SR, —C(O)NRR, —C(S)NRR, or —C(NR)NRR, where each X is independently a halogen ("halo"): F, Cl, Br, or I; and each R is independently H, alkyl, cycloalkyl, aryl, (aryl)alkyl (e.g., benzyl), heteroaryl, (heteroaryl)alkyl, heterocycle, heterocycle(alkyl), or a protecting group. As would be readily understood by one skilled in the art, when a substituent is keto (=O) or thioxo (=S), or the like, then two hydrogen atoms on the substituted atom are replaced. In some embodiments, one or more substituents above can be excluded from the group of potential values for substituents on the substituted group. The various R groups in the schemes and figures of this disclosure can be one or more of the substituents recited above, thus the listing of certain variables for such R groups (including $R^1$, $R^2$, $R^3$, etc.) are representative and not exhaustive, and can be supplemented with and/or substituted by one or more of the substituents above.

The term "amino acid" refers to a natural amino acid residue (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acid (e.g. phosphoserine; phosphothreonine; phosphotyrosine; hydroxyproline; gamma-carboxyglutamate; hippuric acid; octahydroindole-2-carboxylic acid; statine; 1,2,3,4,-tetrahydroisoquinoline-3-carboxylic acid; penicillamine; ornithine; citruline; methyl-alanine; para-benzoylphenylalanine; phenylglycine; propargylglycine; sarcosine; and tert-butylglycine) residue having one or more open valences. The term also comprises natural and unnatural amino acids bearing amino protecting groups (e.g. acetyl, acyl, trifluoroacetyl, or benzyloxycarbonyl), as well as natural and unnatural amino acids protected at carboxy with protecting groups (e.g. as a ($C_1$-$C_6$)alkyl, phenyl or benzyl ester or amide). Other suitable amino and carboxy protecting groups are known to those skilled in the art (see for example, T. W. Greene, *Protecting Groups In Organic Synthesis*; Wiley: New York, Third Edition, 1999, and references cited therein; D. Voet, *Biochemistry*, Wiley: New York, 1990; L. Stryer, *Biochemistry*, (3rd Ed.), W.H. Freeman and Co.: New York, 1975; J. March, *Advanced Organic Chemistry, Reactions, Mechanisms and Structure*, (2nd Ed.), McGraw Hill: New York, 1977; F. Carey and R. Sundberg, *Advanced Organic Chemistry, Part B: Reactions and Synthesis*, (2nd Ed.), Plenum: New York, 1977; and references cited therein).

The terms "linker" or "spacer" means a chemical moiety comprising a covalent bond or a chain of atoms that covalently attaches a targeting moiety (TM), a targeting ligand (TL), a functional group (FG), or a combination thereof to an antibody inhibitor or antibody ligand. The linker can be an alkyl or aryl chain, including heteroatoms, particularly oxygen or nitrogen, repeating units of ethane, ethylene, ethylene glycol, alkyloxy (e.g. polyethylenoxy, polyethylene glycol (PEG), polymethyleneoxy), alkylamino (e.g. polyethyleneamino), lipids, saccharides, peptides, amino acids, for example lysine, diacid esters and amides, wherein the repeating units can range from 2. to about 20. Furthermore, the repeating units can be linked to the same repeating unit or a different repeating unit by, for example, an amide bond.

The term "electrostatic affinity" is a synonym for the totality of intermolecular forces that may or may not be present, including but not limited to hydrogen-bonding, Van der Waals forces, London dispersion forces, hydrophobic interactions, and hydrophilic interactions, for molecular binding, i.e., the interaction between two molecules that results in a stable, non-covalent association.

The term "oligomer" means a molecular complex that consists of a few monomer units, for example less than about 20 monomer units, in contrast to a polymer, where the number of monomers is, in principle, not limited.

The term "saccharide" means a sugar such as starch, cellulose, or an oligosaccharide which is a saccharide polymer of about less than about 20 monosaccharides.

The term "epitope" means the part of an antigen molecule to which an antibody attaches itself.

The term "mimotope" means a macromolecule, often a peptide or peptidomimetic, but can also be a small molecule (e.g., a hapten which a small molecule that, when combined with a larger carrier such as a protein, can elicit the production of antibodies that bind specifically to it), which mimics the structure of an epitope. This property causes an antibody response similar to the one elicited by the epitope. As the mimic of binding site, mimotope analysis can be used in mapping epitopes, identifying drug target and inferring protein interaction networks. Furthermore, a mimotope has potential in the development of new diagnostics, therapeutics and vaccines.

A "peptidomimetic" means a small protein-like chain designed to mimic a peptide. They typically arise either from modification of an existing peptide, or by designing similar systems that mimic peptides. The altered chemical structure is designed to advantageously adjust the molecular properties such as, stability or biological activity. This can have a role in the development of drug-like compounds from existing peptides. These modifications involve changes to molecules that will not occur naturally (such as altered backbones and the incorporation of nonnatural amino acids).

The term "conjugate" means joining two or more chemical compounds, for example, by foming a covalent bond between two or more compounds.

The term "avidity" means refers to the accumulated strength of multiple affinities of individual non-covalent binding interactions, such as between a protein receptor and its ligand, and is commonly referred to as functional affinity. As such, avidity is distinct from affinity, which describes the strength of a single interaction. However, because individual binding events increase the likelihood of other interactions to occur (i.e. increase the local concentration of each binding partner in proximity to the binding site), avidity is not simply the mere sum of its constituent affinities but is the combined effect of all affinities participating in the biomolecular interaction. Avidity can be applied to antibody interactions in which multiple antigen-binding sites simultaneously interact with the target antigenic epitopes, often in multimerized structures. Individually, each binding interaction may be readily broken; however, when many binding interactions are present at the same time, transient unbinding of a single site does not allow the molecule to diffuse away.

Embodiments of the Invention

Various embodiments of an antibody inhibitor or an antibody ligand are represented by Formula I:

wherein

TM is a targeting moiety for an antigen binding site (ABS) wherein the targeting moiety comprises a) a mimotope of an allergen protein epitope peptide sequence, b) a peptidomimetic, or c) a small molecule hapten, each which have a selective electrostatic affinity for the ABS of an immunoglobulin;

TL is a targeting ligand for a conserved nucleotide binding site (NBS) of the immunoglobulin wherein the targeting ligand has a selective electrostatic affinity for the NBS located proximal to the ABS and between the heavy chain and light chain of the immunoglobulin;

FG is a reactive functional group capable of forming a site-directed covalent bond to the amine moiety of an amino acid proximal to the NBS of an allergen reactive immunoglobulin; and $S^1$ is a variable length spacer comprising oligomers of ethylene glycol, amino acids, saccharides, hydrocarbons, fluorinated hydrocarbons, or combination thereof, wherein the spacer is conjugated by one or more lysine moieties and one or more amide bonds to TM, TL, and FG, wherein when the antibody inhibitor bivalently binds to both the ABS and the NBS, the effective concentration of the reactive functional group (FG) near the amino acid of the immunoglobulin increases to irreversibly inhibit the immunoglobulin by the site-directed covalent bond formed by the inhibitor.

Various other embodiments of TL comprise a conjugate of a ligand which electrostatically binds to NBS with a $K_d$ of less than 5 μM. Further embodiments of TL comprise a conjugate of 2-napthaleneacetic acid, indole-3-butyric acid, or fluorene.

Other embodiments of FG comprise a conjugate of an isothiocyanate, an isocyanate, an alkyne, a bromine, an acrylamide, or a maleimide. Embodiments of $S^1$ can also comprise a conjugate of the formula —($CH_2$—X—

$CH_2CH_2$—X—$CH_2)_y$—, wherein X is O or NR wherein R is H or ($C_1$-$C_4$) alkyl, and y is 1 to 12.

Various embodiments of TM comprise a conjugate of a) a mimotope of an allergen protein, wherein the allergen protein is from the primary sequence of Ara h 1, Ara h 2, Ara h 3, or Ara h 6, b) the peptide sequence of a peptidomimetic, wherein the peptidomimetic electrostatically binds to Rituximab, Trastuzumab or a pharmaceutical antibody, or c) a small molecule hapten, wherein the molecule is dinitrophenol, dansyl, penicilloyl, oxaliplatin or a drug having a molecular weight under 800 Daltons.

Other various embodiments of an antibody inhibitor or antibody ligand are represented by Formula II:

$$S^2\text{—TM—}S^1\text{—FG} \quad \text{(II)}$$
$$\ \ |\qquad\quad\ |$$
$$\ \ TG\qquad\ \ TL$$

wherein

TM is a targeting moiety for an antigen binding site (ABS) wherein the targeting moiety comprises a) a mimotope of an allergen protein epitope peptide sequence, b) a peptidomimetic, or c) a small molecule hapten, each which have a selective electrostatic affinity for the ABS of an immunoglobulin;

TL is a targeting ligand for a conserved nucleotide binding site (NBS) of the immunoglobulin wherein the targeting ligand has a selective electrostatic affinity for the NBS located proximal to the ABS and between the heavy chain and light chain of the immunoglobulin;

FG is a reactive functional group capable of forming a site-directed covalent bond to the amine moiety of an amino acid proximal to the NBS of an allergen reactive immunoglobulin;

$S^1$ is a variable length spacer comprising one or more variable length ethylene glycol ($EG^1$) spacers and one or more lysine ($K^1$) spacers wherein each $EG^1$ spacer and each $K^1$ spacer is linked by one or more amide bonds;

$S^2$ comprises a variable length ethylene glycol ($EG^2$) spacer and a lysine ($K^2$) spacer linked by an amide bond; and TG is a tag comprising a chromophore or a fluorophore, wherein the ABS targeting moiety (TM), the NBS targeting ligand (TL), and the reactive functional group (FG) are conjugated to $S^1$, and TM is further conjugated to a tag (TG) by a second spacer $S^2$, wherein when the antibody inhibitor bivalently binds to both the ABS and the NBS, the effective concentration of the reactive functional group (FG) near the amino acid of the immunoglobulin increases to irreversibly inhibit the immunoglobulin by the site-directed covalent bond formed by the inhibitor, and the irreversibly inhibited immunoglobulin is tagged by the chromophore or the fluorophore.

In several embodiments, the tag (TG) is fluorescein, dansyl, dinitrophenol, a rhodamine, a coumarin, a xanthene, a cyanine, or an Alexa Fluor. In some embodiments of the inhibitor or ligand of Formula II:

TL is a conjugate of 2-napthaleneacetic acid, indole-3-butyric acid, or fluorene;
FG is a conjugate of isothiocyanate;
$EG^1$ and $EG^2$ are conjugates of the formula —($CH_2$—X—$CH_2CH_2$—X—$CH_2)_y$—;
X is O or NR wherein R is H or ($C_1$-$C_4$) alkyl;
y is 1 to 12; and
TM is a conjugate of a) a mimotope of an allergen protein, wherein the allergen protein is from the primary sequence of Ara h 1, Ara h 2, Ara h 3, or Ara h 6, b) the peptide sequence of a peptidomimetic, wherein the peptidomimetic binds to Rituximab, Trastuzumab or a pharmaceutical antibody, or c) a small molecule hapten, wherein the molecule is dinitrophenol, dansyl, penicilloyl, oxaliplatin or a drug having a molecular weight under 800 Daltons.

In various other embodiments, FG is reactive to the amino moiety of lysine proximal to the NBS of an allergen reactive immunoglobulin.

In yet other various embodiments, the antibody inhibitor or antibody ligand is represented by Formula III:

$$\quad\qquad\qquad\quad FG \qquad\qquad\text{(III)}$$
$$\qquad\qquad\qquad\ |$$
$$\qquad\quad\ K^2\quad\ EG^1\quad\ EG^1$$
$$EG^2\ \diagdown\ TM\diagup\quad\diagdown\ K^1\diagup$$
$$\ |\qquad\qquad\qquad\quad\ |$$
$$TG\qquad\qquad\qquad\ EG^2$$
$$\qquad\qquad\qquad\qquad\ \diagdown TL$$

wherein

TM is a targeting moiety for an antigen binding site (ABS) wherein the targeting moiety comprises a) a mimotope of an allergen protein epitope peptide sequence, b) a peptidomimetic, or c) a small molecule hapten, each which have a selective electrostatic affinity for the ABS of an immunoglobulin;

TL is an optional targeting ligand for a conserved nucleotide binding site (NBS) of the immunoglobulin wherein the targeting ligand has a selective electrostatic affinity for the NBS located proximal to the ABS and between the heavy chain and light chain of the immunoglobulin;

FG is an optional reactive functional group capable of forming a site-directed covalent bond to the amine moiety of an amino acid proximal to the NBS of an allergen reactive immunoglobulin; wherein the inhibitor comprises at least one of TL or FG;

$EG^1$ is a variable length spacer comprising one or more spacers of the formula —($CH_2$—X—$CH_2CH_2$—X—$CH_2)_y$— wherein the —($CH_2$—X—$CH_2CH_2$—X—$CH_2)_y$— spacer is linked to one or more $K^1$ spacers; y is 1 to 12; X is O or NR wherein R is H or ($C_1$-$C_4$) alkyl;

$K^1$ is a spacer comprising one or more lysine moieties;

$EG^2$ is an optional variable length spacer comprising the formula —($CH_2$—X—$CH_2CH_2$—X—$CH_2)_y$—;

$K^2$ is an optional spacer comprising a lysine moiety; wherein the spacers $EG^1$, $EG^2$, $K^2$, and —($CH_2$—X—$CH_2CH_2$—X—$CH_2)_y$— are linked by one or more amide bonds; and TG is an optional tag comprising a chromophore or a fluorophore; wherein the ABS targeting moiety (TM), the NBS targeting ligand (TL), and the reactive functional group (FG) are conjugated to $K^1$, $EG^1$ and $EG^2$, and TM is further conjugated to an optional tag (TG) by $K^2$ and $EG^2$, wherein when the antibody inhibitor bivalently binds to both the ABS and the NBS, the effective concentration of the reactive functional group (FG) near the amino acid of the immunoglobulin increases to irreversibly inhibit the immunoglobulin by the site-directed covalent bond formed by the inhibitor, and the irreversibly inhibited immunoglobulin is tagged by the chromophore or the fluorophore when the inhibitor contains TG.

In various embodiments of the antibody inhibitors of antibody ligands, bivalent binding of TM and TL to the immunoglobulin synergistically enhance the avidity of the inhibitor. In other embodiments, FG is reactive to the amino moiety of lysine proximal to the NBS of an allergen reactive immunoglobulin. In yet other embodiments, TL comprises a conjugate of 2-napthaleneacetic acid, indole-3-butyric acid, or fluorene. In various other embodiments, FG comprises a conjugate of isothiocyanate.

Embodiments of the antibody inhibitor or antibody ligand are represented by the compounds:

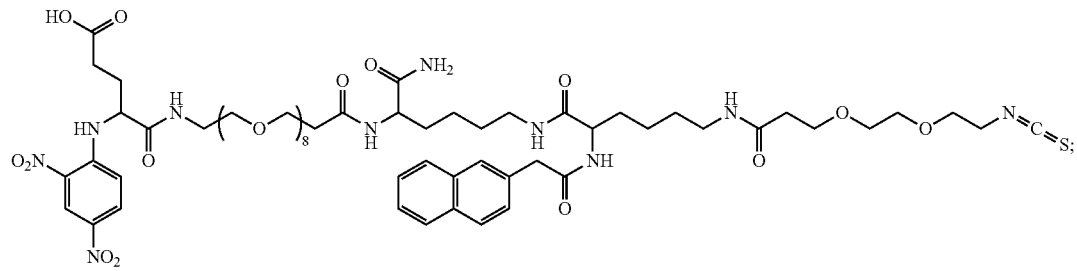

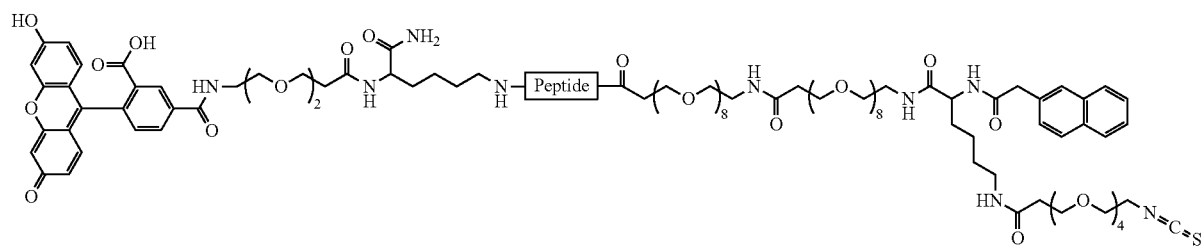

wherein Peptide is a targeting peptide to Trastuzumab;

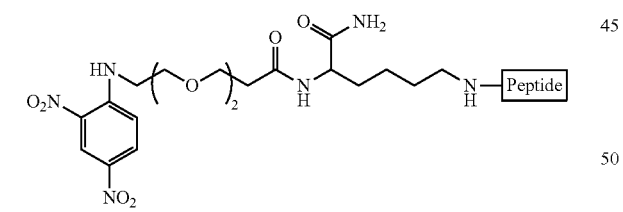

wherein Peptide is a targeting peptide to Trastuzumab;

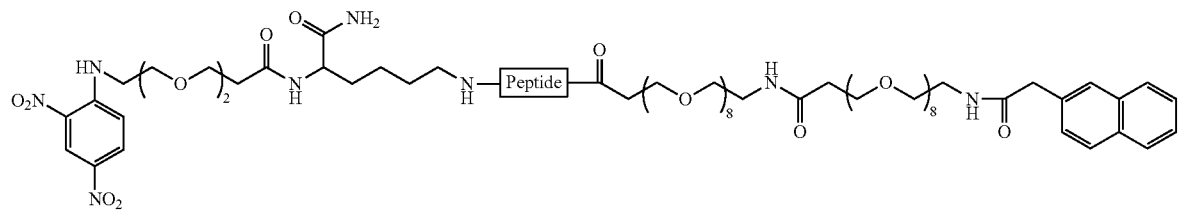

w

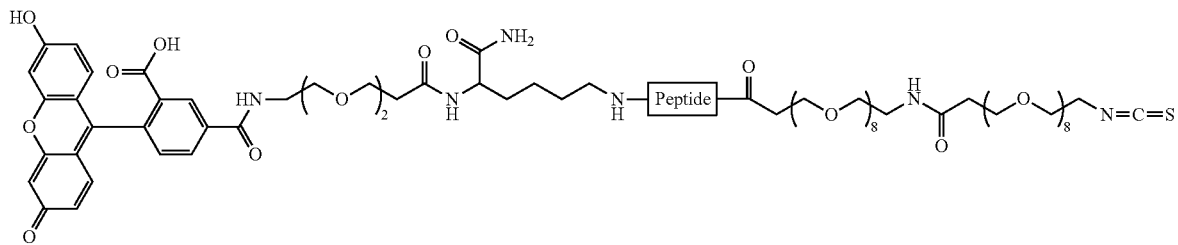
wherein Peptide targeting peptide to Trastuzumab;
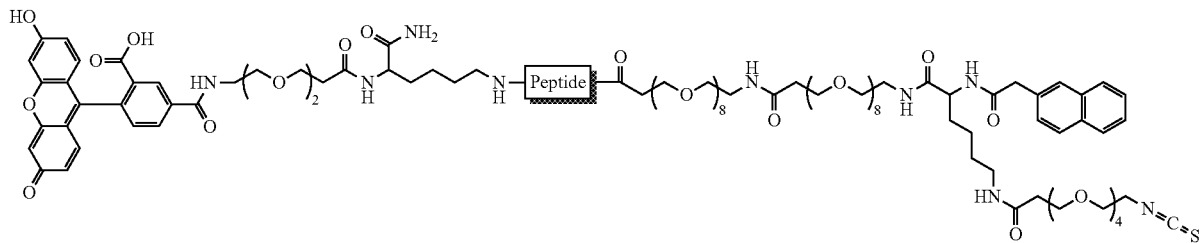
wherein Peptide targeting peptide to Rituximab;
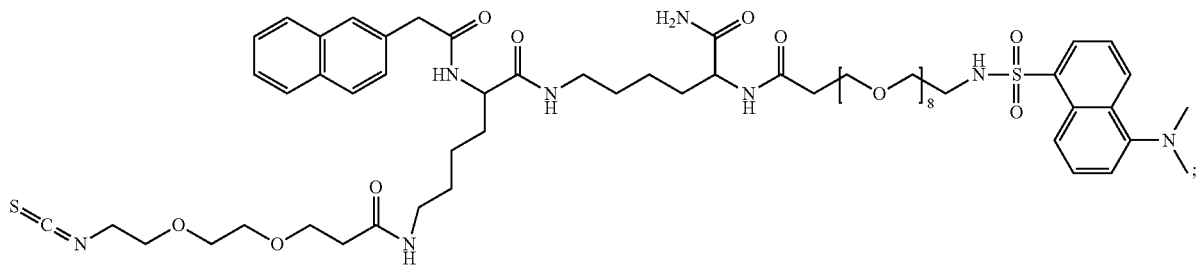
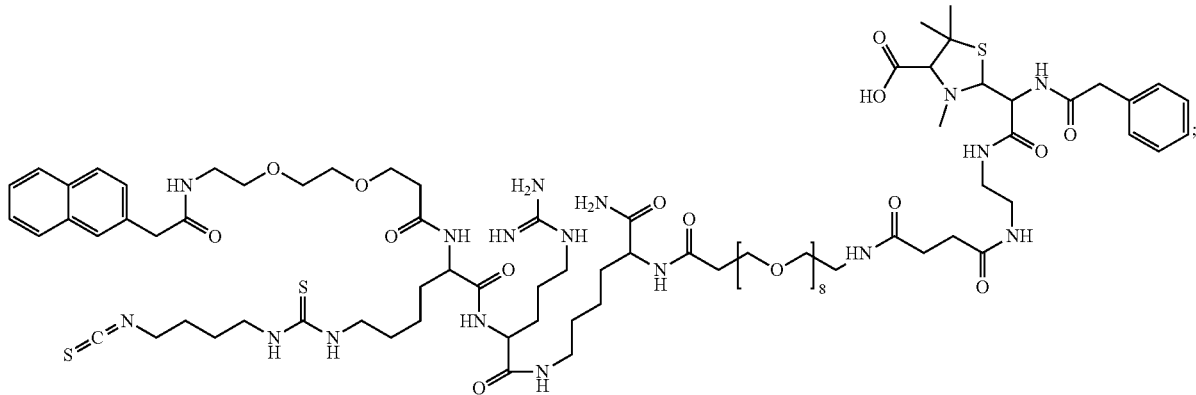
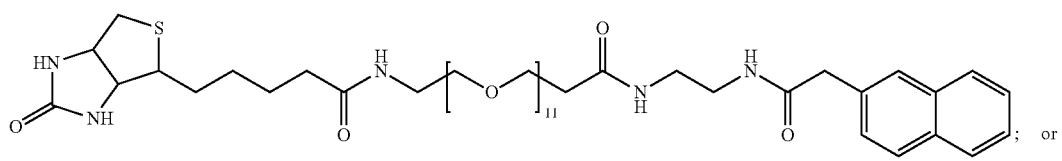 or -continued

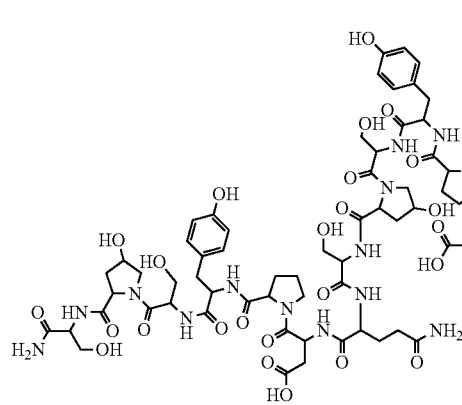
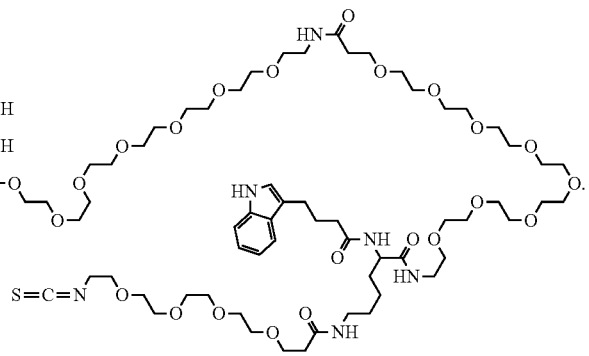

Various embodiments of methods for the forgoing antibody inhibitors or antibody ligands include inhibiting or reducing the severity of an allergic reaction comprising administering an effective amount of the inhibitor to a subject a) prior to exposure of the subject to an allergen, b) after exposure of the subject to an allergen, c) during an allergic response of the subject to an allergen, or d) prior to immunotherapy desensitization of a subject requiring immunotherapy desensitization, wherein inhibition of the immunoglobulin antibody to the allergen prevents degranulation of mast cells and basophils thereby substantially lowering the allergic response of the subject to the allergen. Other embodiments include methods of measuring the reaction kinetics of degranulation in an assay comprising adding a measured aliquot or a series of measured aliquots of the inhibitor or ligand to a) a monoclonal antibody in-vitro assay, or b) a blood serum in-vitro assay, to determine the rate of degranulation.

Additional embodiments include methods of modulating immunological expression of T-cell receptors, B-cell receptors, or a combination thereof, by a) administering an effective amount of the inhibitor or ligand to a subject, or b) adding a measured amount of the inhibitor or ligand to an immunological in-vitro assay, to determine a dose-response relationship of the inhibitor or ligand and an immune response. Yet other various embodiments include methods for analyzing antibodies comprising tagging an antibody in an in-vitro assay with the inhibitor or ligand and analyzing the assay by flow-cytometry or ELISA to quantitate inhibition and provide feedback to a) the design of an inhibitor or ligand, b) the structure and function of an immunoglobulin, or c) the concentration of an immunoglobulin in a sample.

In other various embodiments, the inhibitor or ligand is co-administered with epinephrine to mitigate an anaphylaxis response in a subject exposed to an allergen.

Figure 18:
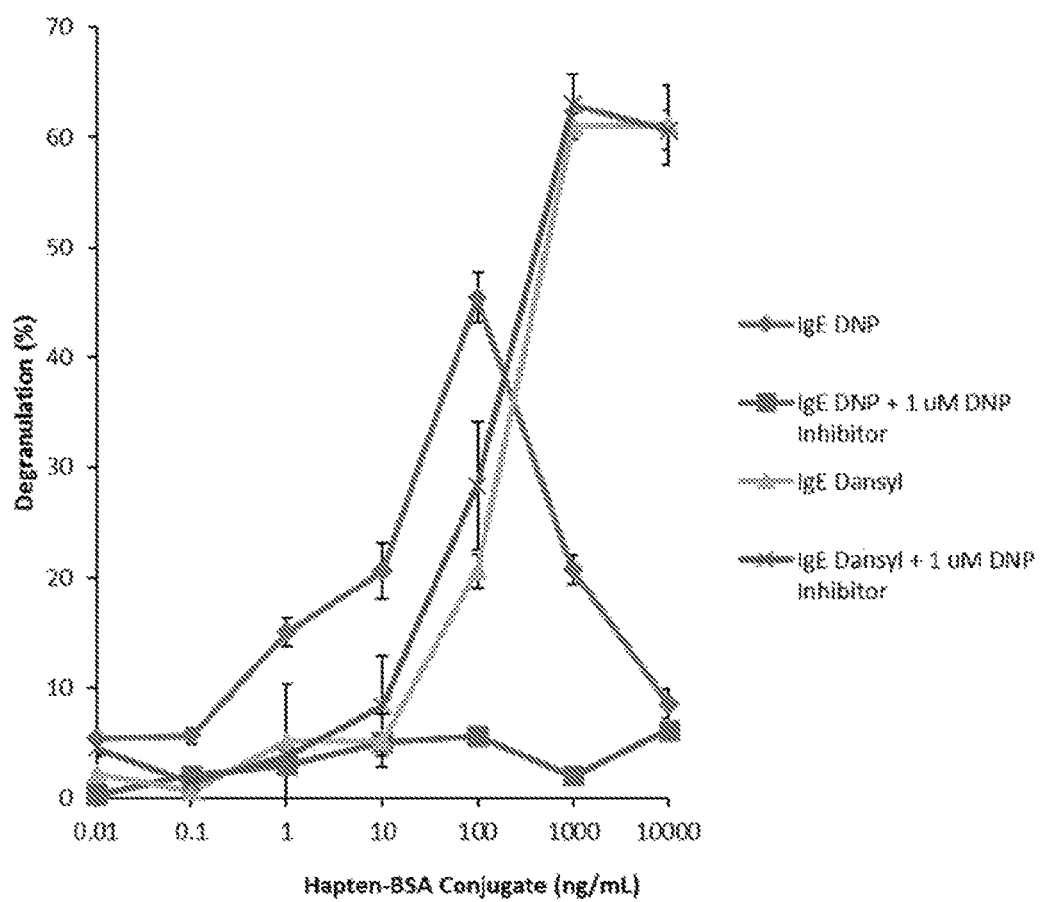
FIG. 18. Inhibition of degranulation caused by DNP-BSA or Dansyl-BSA. Cells were primed with $IgE^{DNP}$ or $IgE^{dansyl}$ and then incubated overnight with either 1 µM DNP cHBI with no inhibitor. Degranulation was triggered using DNP-BSA for red or blue lines or dansyl-BSA for green or purple lines.

The allergy inhibitors described in this patent have a wide range of potential usages. The ideal usage would be as a preemptive treatment to prevent severe allergic reactions. The cHBI molecules would be formulated into a drug either for oral or injection delivery that would be taken regularly (daily, weekly, etc.) to prevent mast cell degranulation. The formulation could be altered to be specific to any allergen (food, drug, environmental, etc.). Allergy inhibitors could also be administered after allergen exposure to mitigate allergy symptoms or co-administered with epinephrine during an anaphylaxis response to prevent further proliferation of the degranulation reactions. cHBI treatment could also be used as an important component of the common immunosuppressive therapies. In many cases when the patient is extremely sensitive for the allergen, it is not possible to apply allergy immunotherapy because even the lowest dose of the allergen can trigger systemic anaphylaxis. cHBI, through inhibiting such a response, can be used in such treatments to make it possible for the patient to be exposed to low doses of the allergen for desensitization.

The cHBIs also have other immunological uses. The NBS may also exist in T-cell receptors (TCRs) and B-cell receptors (BCRs). Therefore, given that T-cells and B-cells bind similar peptide epitopes, it would be possible to synthesize similar cHBIs to target specific T cells or B cell clones and modulate immunological expression. This could be purely scientific, where the cHBIs are tagged with fluorophores and then used for labeling purposes of immunological cells or proteins. However, this could also be therapeutic; cHBIs could be used to treat autoimmune diseases and inhibit T cell, B cell and/or antibody mediated autoimmune diseases.

We have synthesized several cHBIs to prevent mast cell degranulation in vitro. We have also synthesized several cHBIs to characterize the covalent bond formation and the kinetics of reaction. The cHBI utilizes avidity enhancement from bivalent binding at both the NBS and ABS to improve both the selectivity and potency. This bivalent binding then improves the kinetics of a chemical reaction at an amino acid side chain near the NBS. We synthesized several cHBIs with ABS ligands targeting either the monoclonal antibody Rituximab or Trastuzumab. These cHBIs had slight variations in linker lengths and configurations, demonstrating the versatility in the design. We tagged these cHBIs with a fluorophore (fluorescein) and then performed several experiments to confirm cHBI binding to Ig molecules, the competitive inhibition of NBS ligand binding, and western blots to specify which chain (light or heavy) the cHBI attached (FIGS. 4-9). These experiments confirm the specificity of the covalent interaction on Ig molecules.

We performed similar experiments using a small molecule, DNP, as the ABS ligand and an anti-DNP IgE molecule as the Ig (FIG. 10). We used the DNP/anti-DNP IgE system to demonstrate the potential usage of cHBI design against drug allergies. We confirmed that a cHBI molecule with a DNP moiety binds to anti-DNP IgE, and competitively inhibits its interaction with NBS ligands (FIG. 11). Finally, we demonstrated that the same cHBI inhibited cellular degranulation in vitro when the stimulant was DNP-BSA, while did not show inhibition when the activation of degranulation was stimulated by molecules that targeted IgE antibodies that were specific for molecules other than DNP (FIG. 18).

Figure 13:
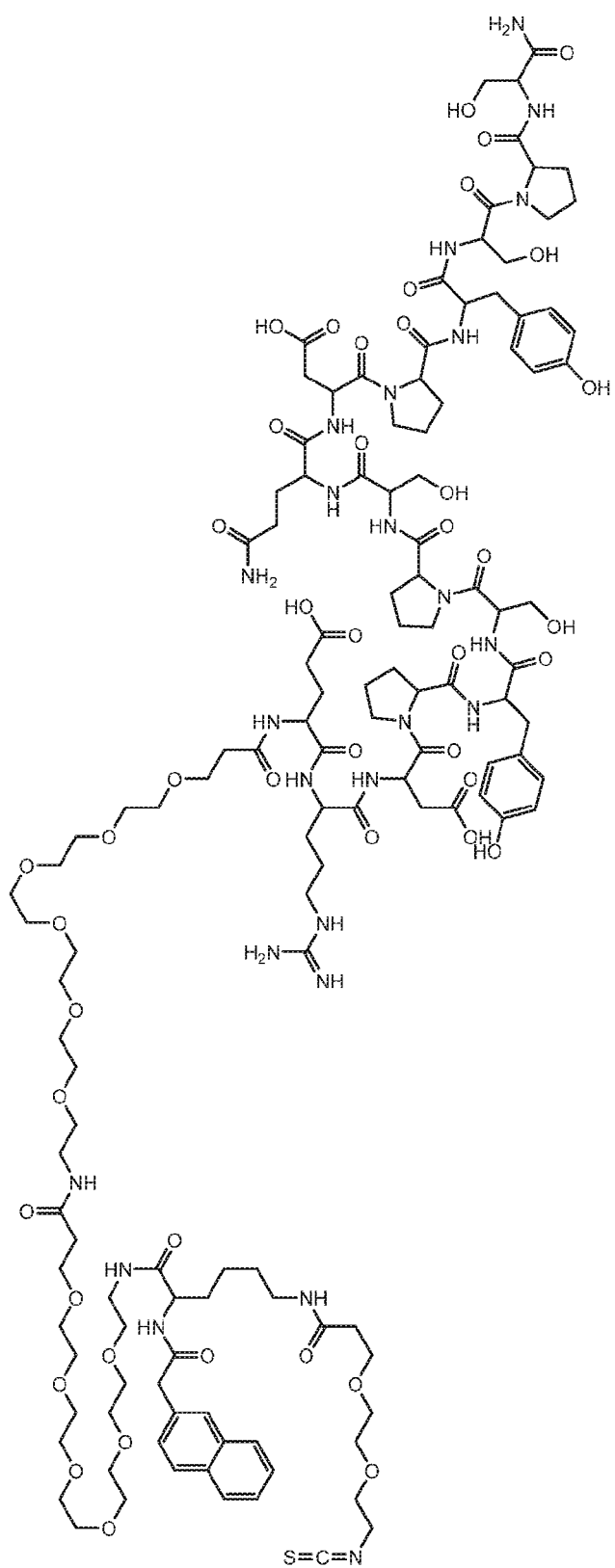
FIG. 13. Ara h 2 cHBI molecule with epitope number 2 from Ara h 2.
Figure 14A:
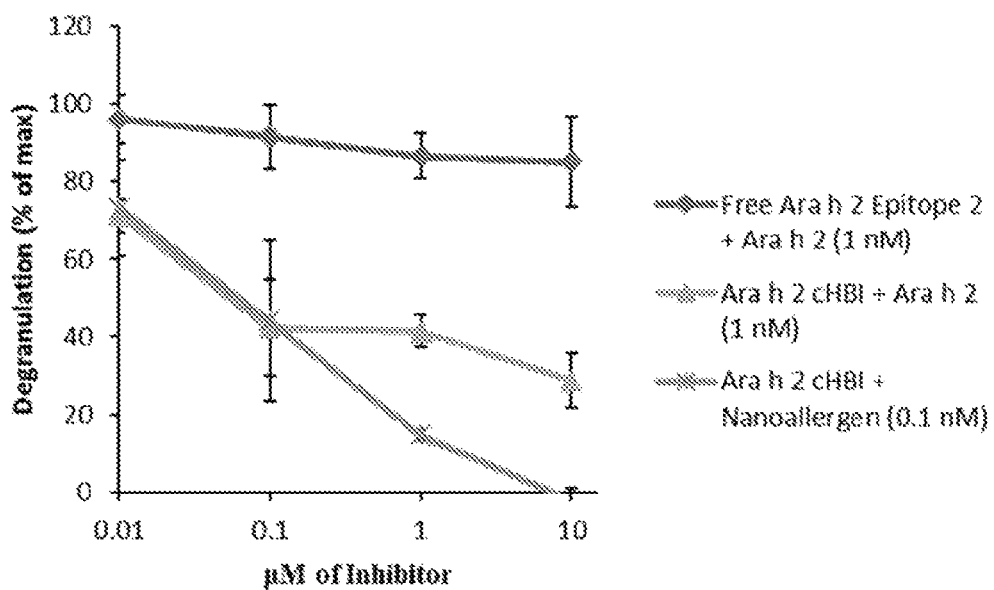
FIG. 14A-14B. Ara h 2 cHBI was incubated for three hours prior to degranulation with either Ara h 2 or a 2% loaded epitope 2 Nanoallergen in (A). As a control, degranulation with DNP-BSA was not effected by incubation with Ara h 2 cHBI's (B).
Figure 14B:
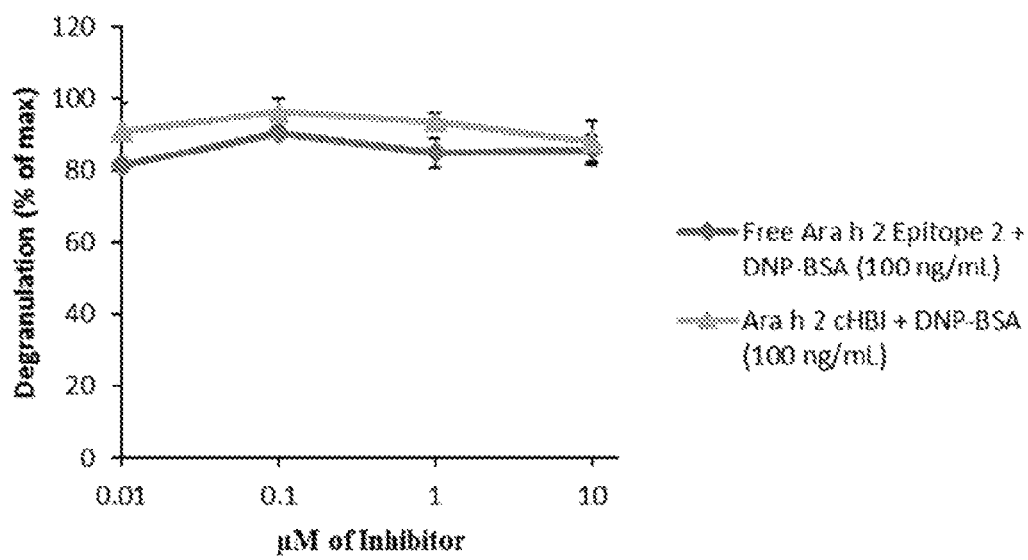
Figure 15:
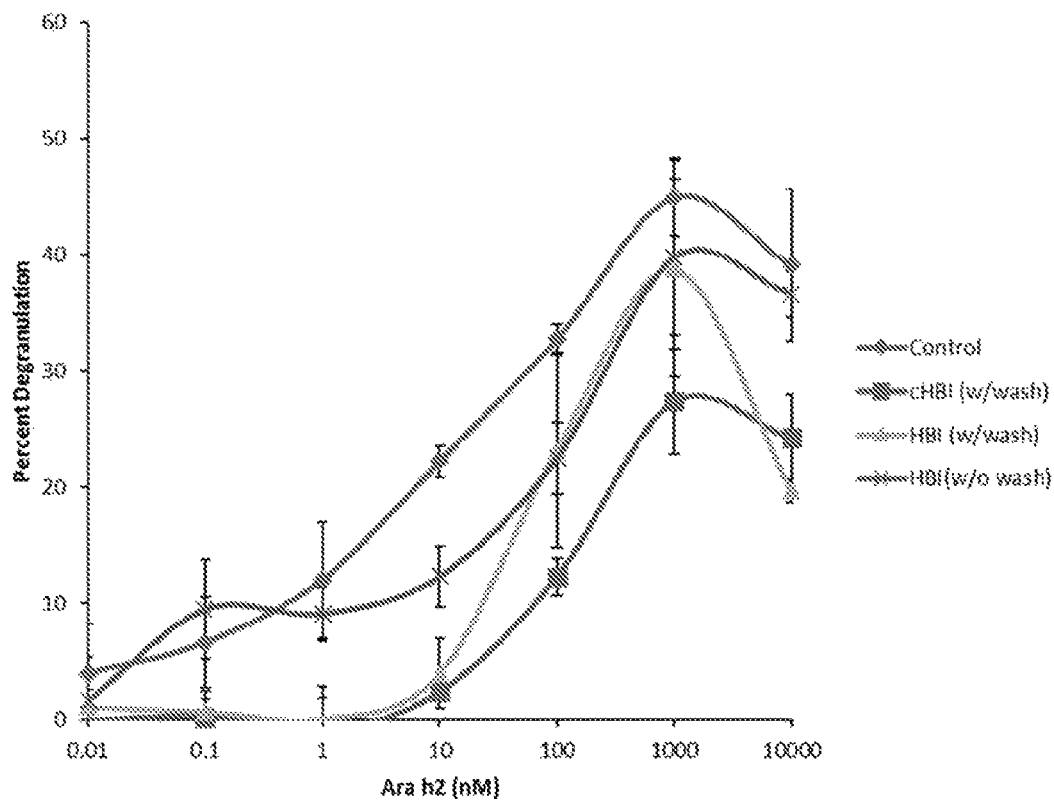
FIG. 15. A degranulation inhibition experiment was performed with a three-hour incubation of either cHBI's or HBI's (without isothiolcynate).
Figure 16A:
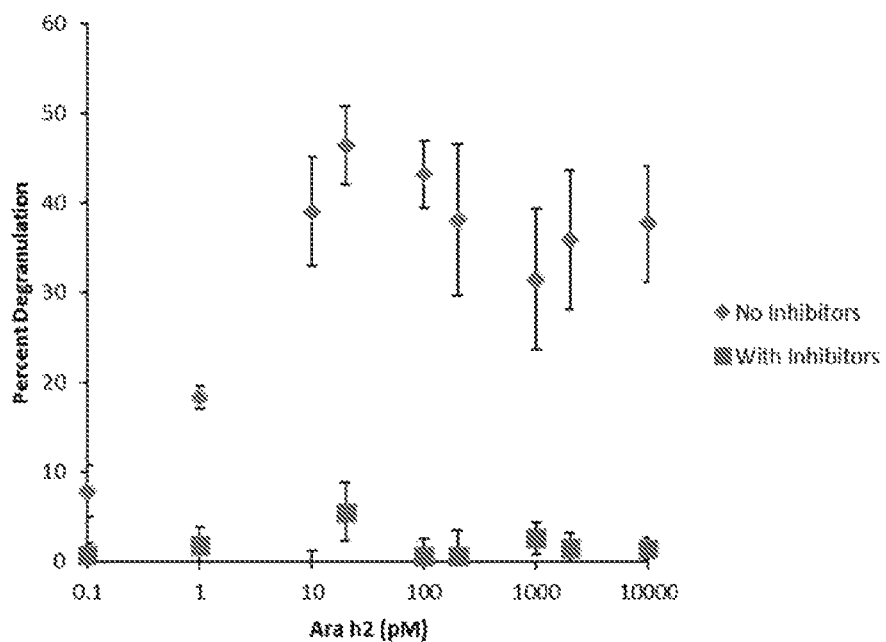
FIG. 16A-16B. Combination of other Ara 2 cHBI's with other epitope targeting peptides improves inhibition. An optimal mixture of 50 nM Ara h 2 cHBI-2, 500 nM cHBI-3, 500 nM cHBI-6 was incubated for 16 hours prior to degranulation with either Ara h 2 (A) or crude peanut extract (B).
Figure 16B:
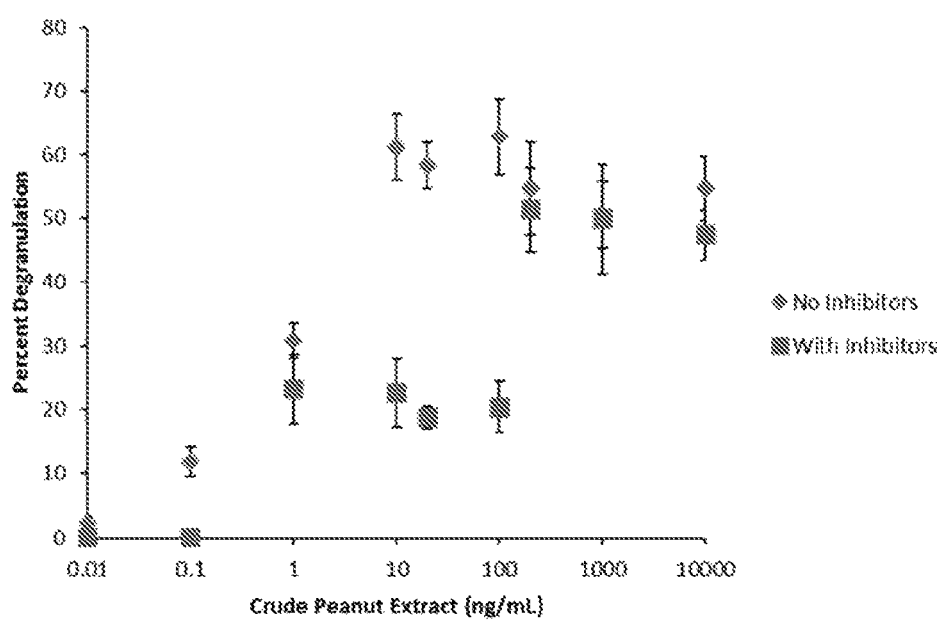
Figure 17:
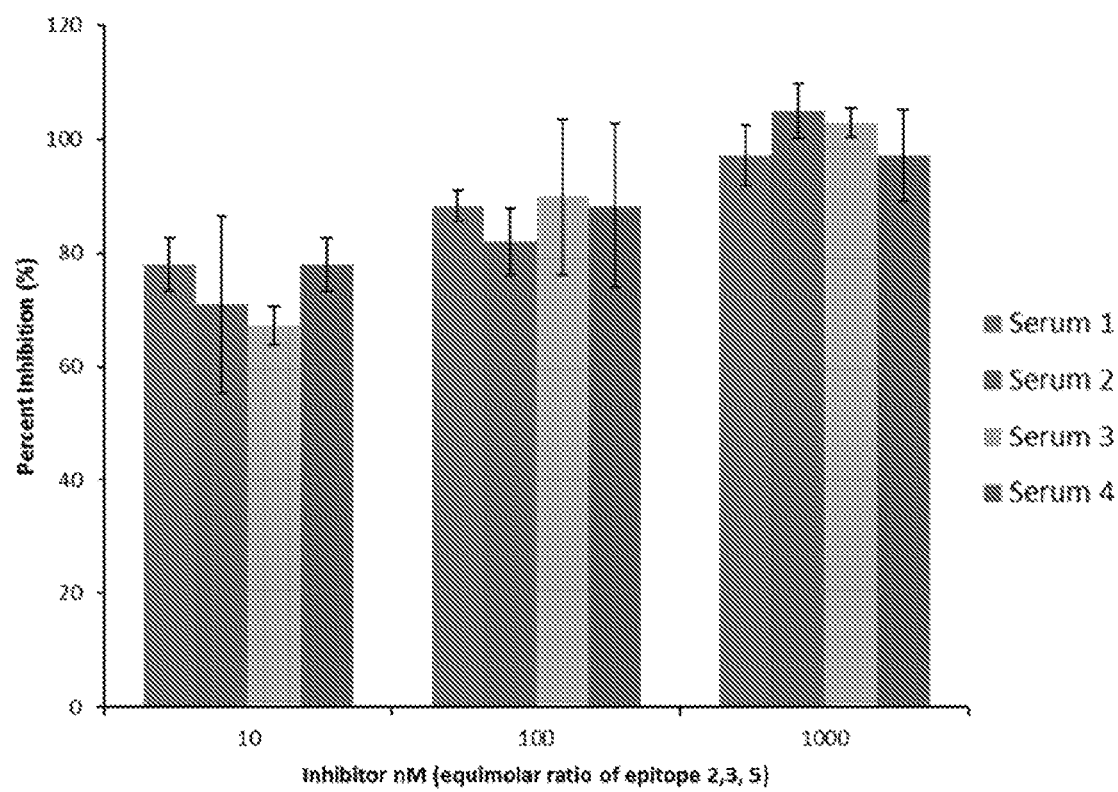
FIG. 17. An eqimolar ratio of Ara h 2 cHBI-2, 3, and 5 were incubated overnight with cells primed with 4 different seras and degranulated with 1 nM Ara h 2. The percent degranulation inhibition is recorded.
Figure 45:
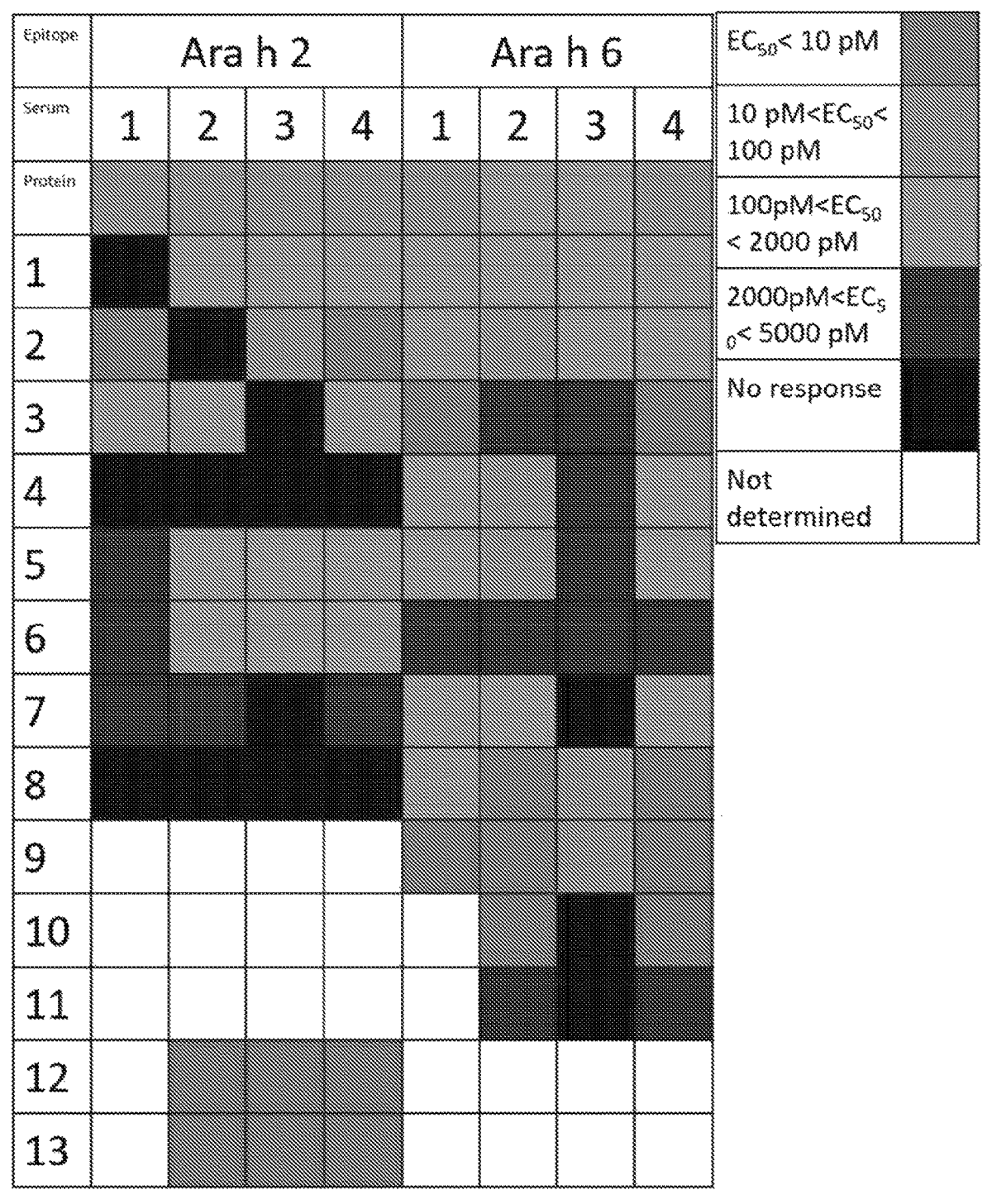

We can also synthesize cHBIs to inhibit allergic reactions caused by allergen proteins such as peanuts. We sought to inhibit allergic reactions from the major peanut protein, Ara h 2 and determined eight potential ABS ligands that could be used in cHBI design (Table 1, and FIG. 45). Then, using the same cHBI scheme as Rituximab or Trastuzumab cHBIs, we designed several Ara h 2 specific cHBI molecules (FIG. 13). We demonstrate in vitro cellular degranulation inhibition using these cHBI molecules in combination and demonstrate their effectiveness in preventing cellular degranulation over several patient seras (FIG. 14-17).

TABLE 1

A. Ara h 2 epitopes.

| Epitope# | Sequence | Number | Notes | References |
|---|---|---|---|---|
| 1 | NLRPCEQHLMQKIQRD (SEQ ID NO: 5) | 38-53 | this is alpha helix 2, also shown homology to walnut epitope | Mueller et al., 2011. Maleki et al, 2011. |
| 2 | ERDPYSPSQDPYSPS (SEQ ID NO: 6) | 79-91 | shown homology to walnut epitope | Mueller et al., 2011. Stanley, JS, 1997. McDermott et al., 2007. Maleki et al, 2011. Albrecht, M, 2009. |
| 3 | SDRLQGRQQ (SEQ ID NO: 7) | 114-123 | | Mueller et al., 2011, |
| 4 | RRCQSQLER (SEQ ID NO: 8) | 28-35 | alpha helix 1 | Mueller et al., 2011, Stanley, JS, 1997. Albrecht, M, 2009. |
| 5 | HASARQQWEL (SEQ ID NO: 9) | 15-24 | | Albrecht, M, 2009. |
| 6 | RQQEQQFKRELRNLPQQ (SEQ ID NO: 10) | 120-136 | this is alpha helix 5, homology with ara h 6 | Mueller et al., 2011, |
| 7 | PQRCDLE (SEQ ID NO: 11) | 142-148 | | Mueller et al., 2011, |
| 8 | CDLEVESGGRDRY (SEQ ID NO: 12) | 145-157 | C terminus of protein | McDermott et al., 2007. |
| 9 | CEALQQIMENQSD (SEQ ID NO: 13) | 97-109 | | Otsu et al, 2014 |
| 10 | CNELNEFENNQR (SEQ ID NO: 14) | | | Otsu et al, 2014 |
| 11 | PRPCEQHLMQKI (SEQ ID NO: 15) | | | Otsu et al, 2014 |
| 12 | ELQGDRRRCQSQLERA (SEQ ID NO: 16) | | Homology to Ara h 3 epitopes | Bublin et al. |
| 13 | DPYSPSDRRGAGSS (SEQ ID NO: 17) | | Homology to Ara h 1 and ara h 3 epitopes | Bublin et al. |

Note:
Epitope 2 has two hydroxyproline post-translational modifications that were incorporated into the epitope-lipid conjugate.

B. Ara h 6 epitopes.

| Epitope# | Sequence | Number | Notes | References |
|---|---|---|---|---|
| 1 | MRRERGRGQDSSSS (SEQ ID NO: 18) | 24-37 | | K Otsu, Dreskin, 2014. |
| 2 | KPCEQHIMQRI (SEQ ID NO: 19) | 45-55 | Homology to ara h2 epitope 11 | K Otsu, Dreskin, 2014. |
| 3 | YDSYDIR (SEQ ID NO: 20) | 35-68 | similar to ara h2 epitope 2 | K Otsu, Dreskin, 2014. |

TABLE 1-continued

| | | | | |
|---|---|---|---|---|
| 4 | CDELNEMENTQR (SEQ ID NO: 21) | 82-93 | Homology to ara h2 epitope 10 | K Otsu, Dreskin, 2014. |
| 5 | CEALQQIMENQCD (SEQ ID NO: 22) | 97-109 | Homology to ara h2 epitope 7 | K Otsu, Dreskin, 2014. |
| 6 | KRELRMLPQQ (SEQ ID NO: 23) | 120-129 | Homology to ara h2 epitope 6, most common? | K Otsu, Dreskin, 2014. |
| 7 | CNFRAPQRCDLDV (SEQ ID NO: 24) | 130-142 | Homology to ara h2 epitope 8 | K Otsu, Dreskin, 2014. |
| 8 | GEQEQYDSYNFGSTRSSDQ (SEQ ID NO: 25) | 38-56 | | Mishra et al. 2014 |
| 9 | QDRQ (SEQ ID NO: 26) | 90-93 | | Mishra et al. 2014 |
| 10 | SCERQVD (SEQ ID NO: 27) | | | Bublin et al., 2015 |
| 11 | IRSTRSSDQQQR (SEQ ID NO: 28) | | | Bublin et al., 2015 |
| 12 | QDRQMV (SEQ ID NO: 29) | | | Bublin et al., 2015 |

Figures 19A, 19B, 19C:
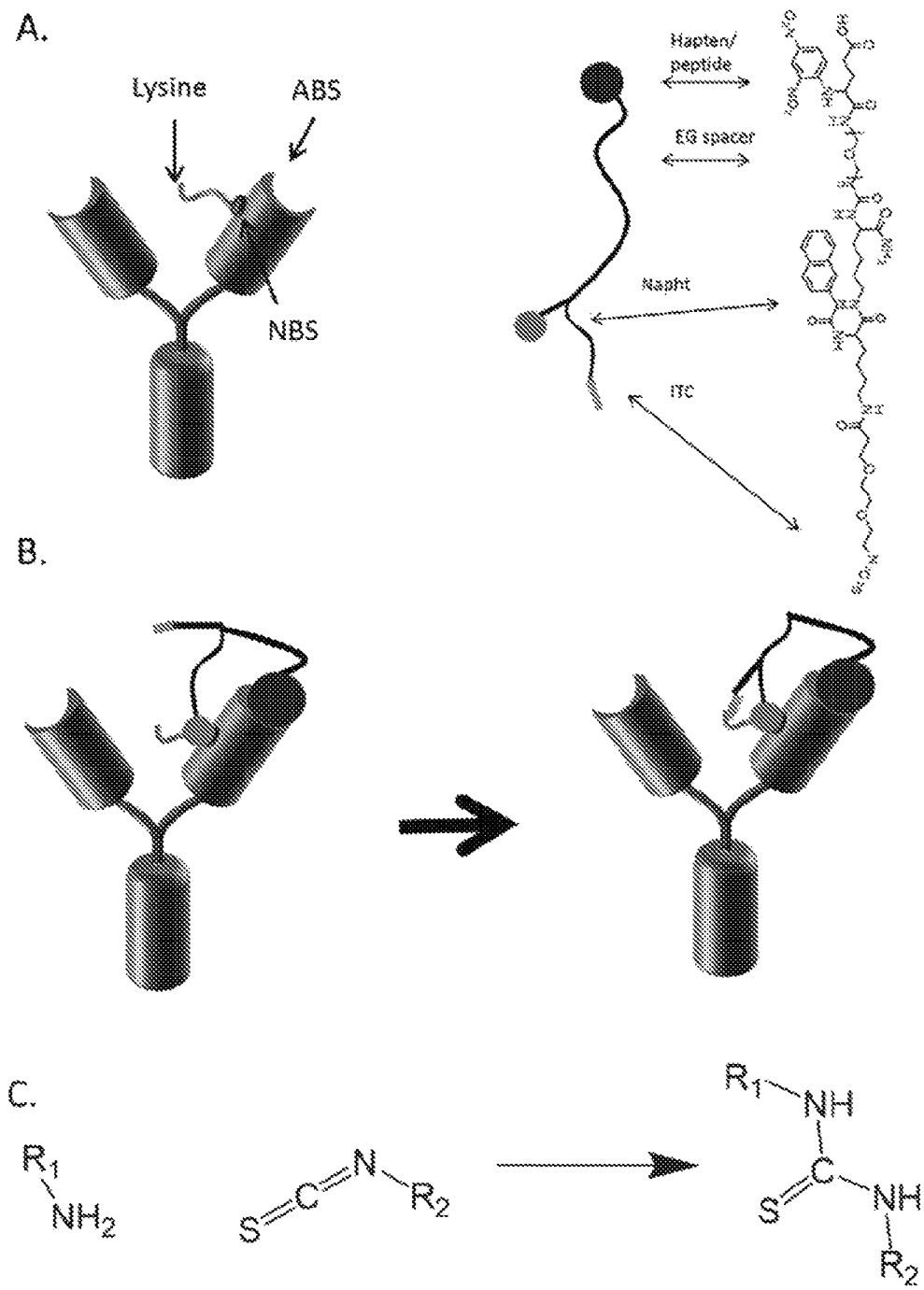
FIG. 19A-19C. (A) A cartoon of an IgE and cartoon and chemical structure of hapten cHBL's, using DNP-HBL as an example. (B) Cartoon demonstrating cHBL bivalent binding to NBS and ABS and subsequent covalent reaction with primary amines. (C) Chemical reaction between ITC group and primary amines to form thiourea bonds.

Covalent Heterobivalent Compounds for Site Specific Covalent Modification of Antibodies and for Inhibition of Allergies to Drugs and Small Molecules Ligand and Inhibitor Design To accommodate both chemical reactivity and specificity of bivalent molecules using both NBS and ABS targeting moieties, we chose the isothiocyanate (ITC) moiety to facilitate chemical conjugation to primary amines on lysine side chains near the NBS. ITC's react slowly with primary amines at physiological pH's, reducing the potential for off target conjugation. We analyzed the crystal structures of several antibodies and compared them, revealing the presence of a lysine side chain available for binding located under 20 nm of the central tryptophan of the NBS on each antibody (FIG. 2). When combined with the ABS and NBS moieties, a cHBL molecule binds to its target antibody bivalently, thereby increasing the effective concentration of the ITC moiety to lysines near the NBS pocket facilitating covalent bond formation with only these amines (FIG. 19). If either ligand does not bind, the half-life of the binding interaction is reduced and as a result of the slow reaction kinetics of ITC, the conjugation is also reduced. Therefore, these three chemical functionalities provide a specific means for covalent modification of antibodies.

The cHBI design consists of three unique chemical moieties that function in concert to provide specific and potent inhibition of IgE mediated degranulation reactions to a specific allergen. The NBS is a underutilized conserved binding site located proximal to the ABS between the heavy and light chain of all immunoglobulins (FIG. 1A). In our laboratory, we have identified a few small molecules with low micromolar affinities for the NBS with a wide range of applications. In this study, NBS ligands are used to increase the overall avidity of the inhibitor molecule with the target IgE to improve specificity and potency of the inhibitors. We selected a NBS ligand, 2-naphteleneacetic acid, which we demonstrated to have a 1.8±0.3 µM. $K_d$ for IgEs (FIGS. 1B, 1C). Likewise, we also selected two ABS ligands to demonstrate the versatility of these inhibitors, penicillin G and dansyl (FIG. 1D). It is important to note while frequently described as an allergy to penicillin G, the actual ABS ligand is the conjugate of penicillin G with a lysine side chain, forming a penicilloyl group and all ABS ligands for penicillin were synthesized with the penicilloyl group (see methods for further details on cHBI synthesis). Additionally, although the goal of our study is the prevention of allergic reactions to drugs, such as penicillin G, given the lack of commercially available IgEs specific to any penicillin drugs, we used another hapten, dansyl, to establish our experimental in vitro model.

Figures 20A, 20B, 20C:
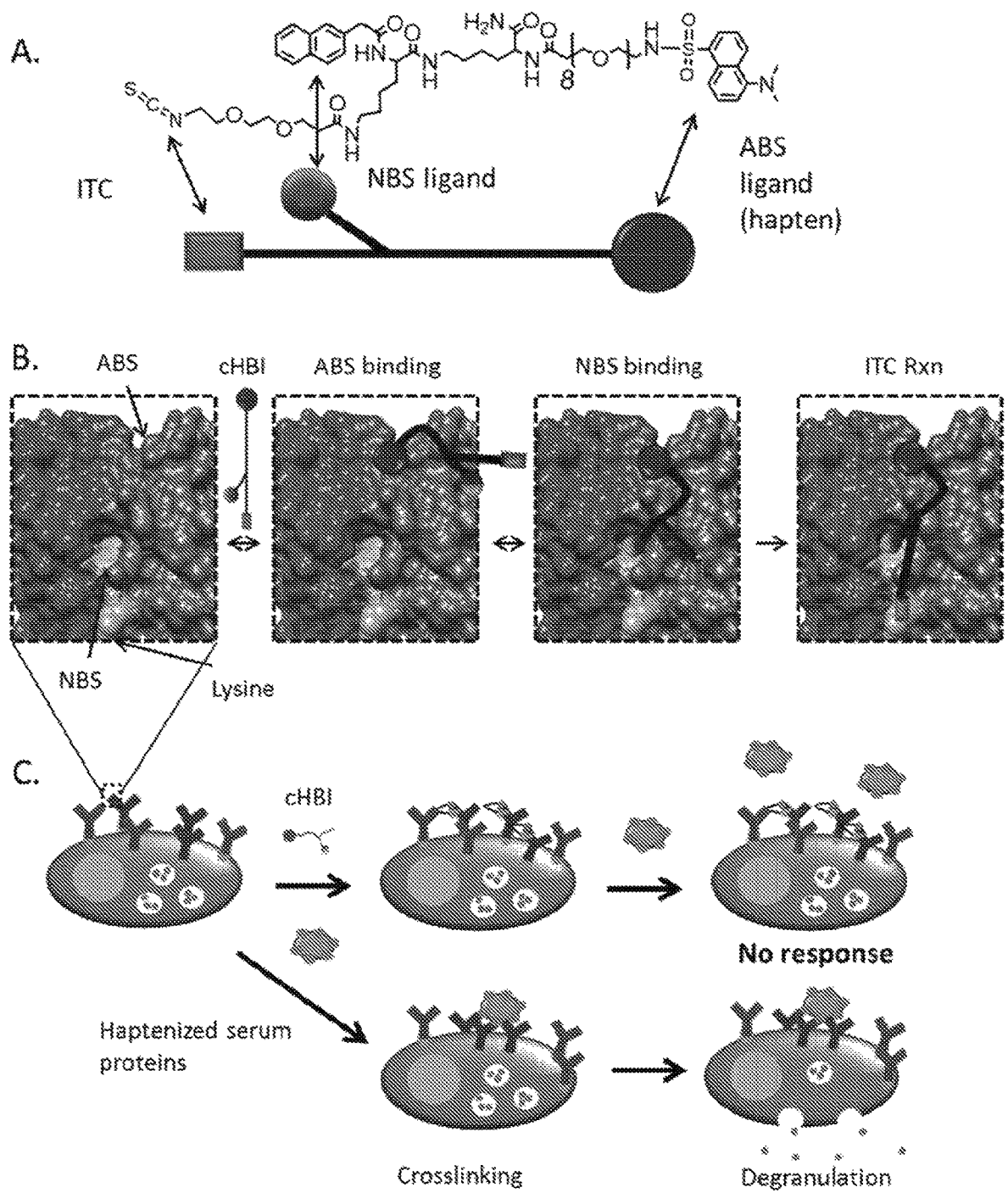
FIG. 20A-20C. Schematic of cHBI molecule with cartoon seen in (A). Crystal structure of typical antibody binding pocket with cartoon depicting cHBI covalent binding in (B). Cartoon demonstrating cHBI degranulation inhibition shown in (C).
Figure 21:
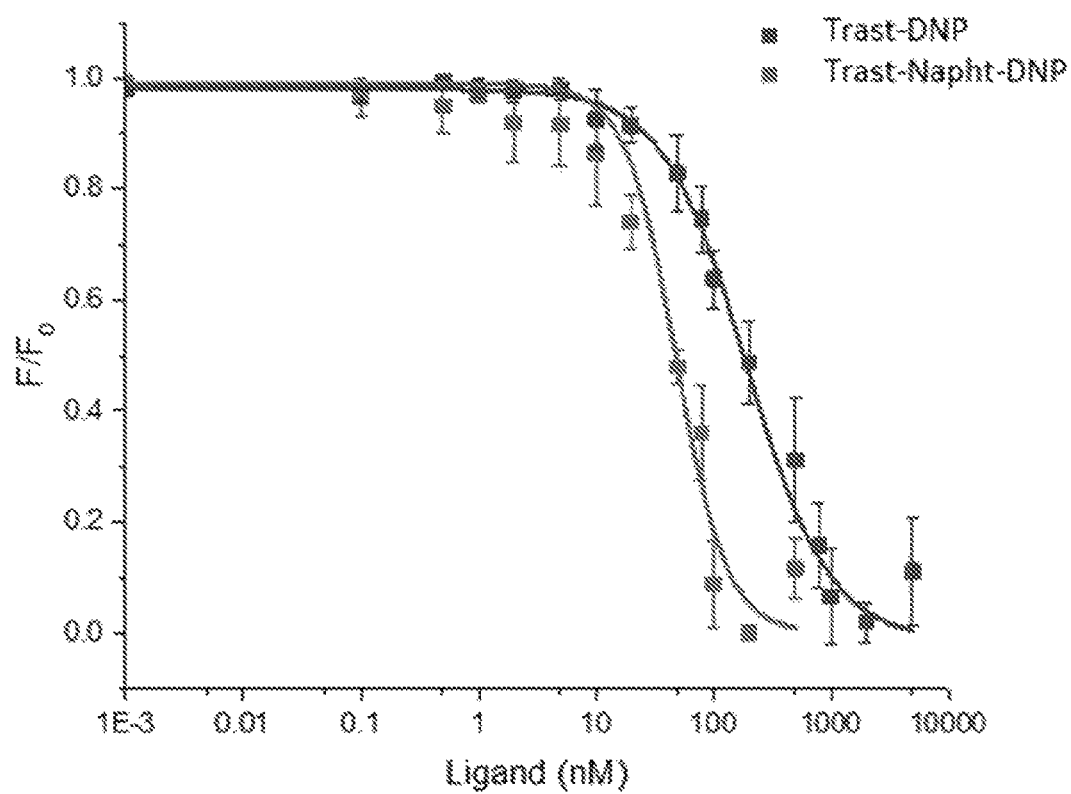
FIG. 21

The most crucial aspect of the cHBI design is a reactive group that can form covalent bonds with bound IgE molecules, essentially permanently inhibiting them, in contrast to HBIs which only form reversible interactions (FIG. 20A). In other words, cHBIs are a type of "suicide inhibitor" that irreversibly binds to a target IgE molecule. However, cHBIs have increased specificity due to their heterobivalent targeting of only antibodies that target drug molecules, making them particularly specific. One of the major challenges of suicide inhibitors is to form covalent bonds quickly with intended targets without unacceptable levels of off target conjugation. Therefore, the reactivity of these types of inhibitors needs to be carefully selected to provide optimal specific binding of these molecules to amino acid side chains of proteins of interest, such as allergy reactive IgEs without conjugating off target proteins. Our cHBI design uses an isothiocynate (ITC) reactive moiety to form covalent bonds with specific allergy reactive IgEs. ITC compounds are frequently found in nature and have been shown to have anti-cancer and anti-microbial qualities. ITC groups form thiourea bonds with primary amines rapidly in elevated pH solutions (>9) but react rather slowly under physiological pH (7.4). This means that under normal physiological conditions, ITC inhibitors will react very slowly to form off target bonds. However, when selectively bound to a protein of interest, the increased effective concentration of primary amines from lysine side chains dramatically increases the reaction kinetics of thiourea bond formation. Using this design, we synthesized two cHBI molecules using two different ABS ligands, a dansyl cHBI and a penicilloyl cHBI (Table 2). Due to complexities of penicilloyl group, additional design considerations were required to synthesize penicilloyl-cHBI's but the same basic molecule design was used for both cHBI's, see methods for further details.

TABLE 2

Disassociation constants for hapten-Napht conjugates.

| Molecule | $K_d$ | Fold Change | |
|---|---|---|---|
| Dansyl | 29.9 ± 10 nM | 4.7 | $P < 0.05$ |
| Dansyl HBI | 6.4 ± 2.5 nM | | |
| Penicilloyl | 20 ± 4 µM | 21 | $P < 0.01$ |
| Penicilloyl-DNP HBI | 0.96 ± 0.11 µM | | |

As demonstrated in FIG. 20B, allergy reactive IgE inhibition is a three-step process. First, either the ABS or NBS ligand will bind to the IgE of interest depending on the relative affinities of the two moieties. Next, bivalent binding will occur, further increasing the stability of the overall inhibitor-IgE bond. Finally, due to increased effective concentration of the inhibitor molecule near the IgE of interest, the inhibitor will form a covalent bond with a lysine side chain near the NBS. We have assessed the crystal structures of several IgE molecules and observed a lysine within 10 nm of the central tryptophan of the NBS in each case (FIG. 2). By permanently binding a competitive inhibitor (the ABS ligand) to the IgE of interest, the resulting increase in effective concentration can overcome the multivalent effects and increased monovalent affinities of natural allergens to their respective IgEs. By preventing this allergen-IgE binding interaction and respective crosslinking, we can prevent degranulation and the consequences of IgE mediated allergic reactions (FIG. 20C). Thus, we have demonstrated that cHBI molecules bivalently bind drug allergy reactive antibodies, specifically form covalent interactions and can prevent antigen binding and therefore degranulation in biological systems.

Antibody Selection and Antigen Binding Moiety Analysis

We developed a model system to evaluate the specificity and selectivity of a cHBL and chose two antibodies to target with the cHBL design: $IgE^{DNP}$ (SPE-7) and trastuzumab. $IgE^{DNP}$ is a well-established monoclonal mouse IgE that has a 20-50 nM affinity for DNP conjugates, which in previous publications we have targeted with bivalent binder. The DNP/$IgE^{DNP}$ system offers several advantages to test the cHBL design. Namely, DNP is a frequently used labeling compound for proteins, so it can be readily detected by an absorbance at 350 nm, and $IgE^{DNP}$ has a resolved antibody crystal structure. However, DNP-$IgE^{DNP}$ system has usually high affinity for its hapten, rendering bivalent approaches less useful, and does not allow for peptide mimetics of protein epitopes. To remedy this, we also chose trastuzumab and a trastuzumab targeting peptide, LLGPYELWELSH (SEQ ID NO: 2), which binds to trastuzumab with a $K_d$ of 200±14 nM as the ABS targeting moiety to demonstrate the effectiveness of this system for typical pharmaceutical antibodies (FIG. 21). This peptide showed enhancement in observed affinity when conjugated to napht with an ethylene glycol spacer, demonstrating a 46±6 nM apparent $K_d$, an over 4 fold increase (FIG. 21). Given the presence of a well-defined ABS targeting moieties, $IgE^{DNP}$ and trastuzumab are excellent candidates to evaluate the cHBL design. We then synthesized two cHBL molecules specific for trastuzumab (trast-cHBL) and $IgE^{DNP}$ (DNP-cHBL) using solid phase peptide synthesis (see methods, FIGS. 22, 23). Note that for the trast-cHBL a fluorescein group was added to the molecule and separated by an $EG_2$ to allow for detection without disrupting peptide binding.

cHBL Compounds Demonstrate Attachment to Antibodies through ITC Moiety

The first objective of this study was to demonstrate that cHBL ligands can form covalent bonds and can selectively bind specific antibodies. In order to test this, we utilized the DNP/$IgE^{DNP}$ hapten/antibody pair because DNP is a molecule that can be readily detected through optical absorbance measurements. To demonstrate the reactivity of the ITC moiety on cHBL molecules and the stability of these molecules, we first incubated the DNP-cHBL molecule at 37° C. in either phosphate buffered saline (pH 7.4) or bicarbonate buffer (pH 10) and monitored the reaction with water using analytical HPLC. ITC moieties undergo a hydrolysis reaction slowly under physiological pHs and rapidly under elevated pHs, so this increased pH serves as a positive control. We observed this reaction through a shift in chromatogram elution and quantified a percent hydrolysis that was considerably more rapid at elevated pH values, reaching >80% in 24 hours but only reached 15% over the same time period at pH 7.4 (FIG. 24A). This result confirms the presence of reactive ITC moieties on cHBL molecules and that these molecules will likely be stable in physiological conditions for at least 24 hours. Next, we incubated 1 μM DNP-cHBL with either 0.1 μM $IgE^{DNP}$ or an IgE specific to an orthogonal molecule, dansyl, ($IgE^{dansyl}$) at pH 7.4. After reaction, the excess cHBL was removed with membrane filtration and the percent conjugation was assessed using analytical HPLC as before. As demonstrated by FIG. 24B, DNP-cHBL molecules selectively conjugated to $IgE^{DNP}$ when compared to the orthogonal IgE over a period of 24 hours, reaching a saturating conjugation after 8 hours. To further confirm the specificity of cHBL molecules, we performed a western blot analysis on the same samples with a gel under reducing conditions, causing the light and heavy chain to separate. We demonstrate highly specific attachment to the heavy chain of $IgE^{DNP}$ under physiological pH and only small attachment to orthogonal IgEs after 24 hours of reaction time (FIG. 24C). This further reinforces the antibody specificity of cHBLs and the optimal reaction time of 8 hours. Finally, it is interesting to note that $IgE^{DNP}$ conjugation was specific to only the heavy chain, seen as a band at 75 kDa. The positive control under elevated pHs demonstrated non-specific attachment to both heavy and light chain, while reactions under pH 7.4 only conjugated to the heavy chain. This suggests that cHBL molecules bind to a specific region of their target antibody only.

Trast-cHBL Selectively and Site-Specifically Binds to Trastuzumab

After demonstrating the cHBLs can selectively bind targets using the DNP-cHBL, we wanted to demonstrate the effectiveness of the cHBL design using targeting peptides as the ABS moiety and further evaluate the site-specific nature of this conjugation. Therefore, we selected a pharmaceutical IgG, trastuzumab as the target for cHBL compounds. Given the identified ABS binding peptide sequence and the presence of the lysines only on the light chain near NBS, trastuzumab is an ideal candidate for demonstrating the effectiveness of the cHBL design. Trast-cHBL selectively binds to trastuzumab through a site-specific attachment of ε-amines of active lysines adjacent to NBS due to the enhanced avidity from bivalent binding of both ABS and NBS targeting ligands. To demonstrate that trast-cHBL selectively and site-specifically binds to trastuzumab, we incubated cHBL compounds (or control compounds) with trastuzumab, removed unreacted ligands with membrane filtration and then characterized the selective and site specificity with enzyme-linked immunosorbent assays (ELISA) and western blot assay.

First, we used direct ELISA to demonstrate the selective binding of trast-cHBL. As stated before, the kinetics of the amine-ITC reaction is highly correlated to pH, with higher pH's vastly improving the kinetics. Therefore, we incubated fluorescein-ITC (FITC) at either pH 7.4 or 10 to serve as a negative and positive control respectively. The data demonstrates that trast-cHBL bound more to trastuzumab with increasing concentration when compared to FITC at either pH value at all concentrations (FIG. 25). A cHBL molecule with an orthogonal ABS binding domain to another pharmaceutical antibody (rituximab) was used to demonstrate selectivity of cHBL binding. It was clearly shown that orthogonal cHBL (rituximab-cHBL) was not selective to trastuzumab up to 20 μM (Table 3). However, it is notable small rituximab-cHBL conjugation to trastuzumab was observed at 20 μM, likely due to NBS ligand facilitating monovalent binding and therefore conjugation. To demonstrate the effects of the NBS targeting ligand (and therefore bivalent enhancement) to cHBL binding, we synthesized similar trast-cHBL molecules where the napht moiety was omitted (Trast-ITC, see Table 3). The trast-cHBL had a significant increase in binding over trastuzumab-ITC at 1 μM but trast-ITC had similar binding with trast-cHBL at higher concentrations (10 and 20 μM). This was likely because the avidity enhancement achieved by trast-cHBL was rendered redundant at high concentrations given that $K_d$ of the binding peptide was approximately 0.2 μM. Additionally, it is important to note that at these higher concentrations, non-specific binding of FITC also occurred, likely indicating that both trast-cHBL and trastuzumab-ITC had similar non-specific interactions at higher concentrations. These results, however, do demonstrate that ABS targeting moieties are critical for selective conjugation to antibodies of interest and that selective conjugation to a specific antibody can be achieved using peptide ABS targeting moieties.

TABLE 3A

Structures and molecular weights of compounds used in this study.

| Compound | MW (Da) | Structure |
|---|---|---|
| DNP-cHBL | 1360.61 | |
| Trast-cHBL (Peptide-LLGPYELWELSH) (SEQ ID NO: 2) | 3477.96 | |

TABLE 3A-continued
Structures and molecular weights of compounds used in this study.
| Compound | MW (Da) | Structure |
|---|---|---|
| Trast-DNP | 1895.1 | 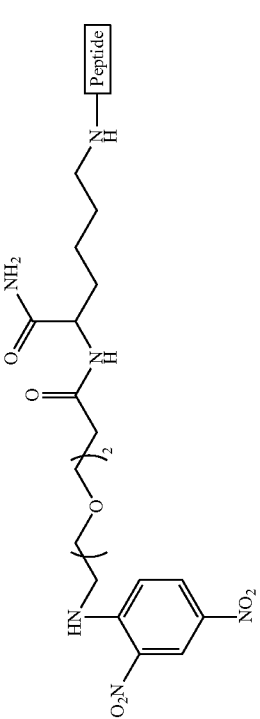 |
| Trast-Napht-DNP | 2882.25 | 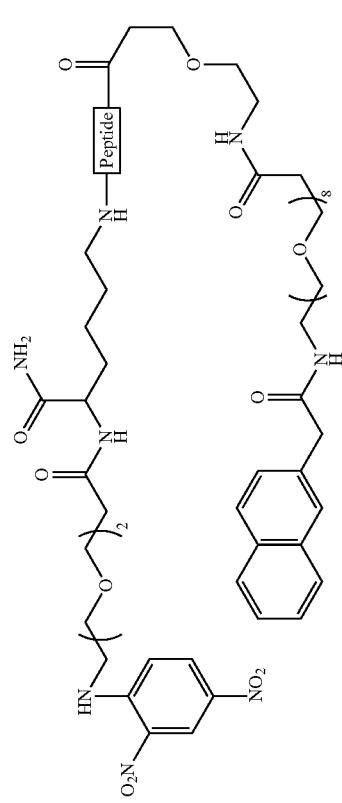 |

TABLE 3A-continued
Structures and molecular weights of compounds used in this study.
| Compound | MW (Da) | |
|---|---|---|
| Trast-ITC | 2948.33 | 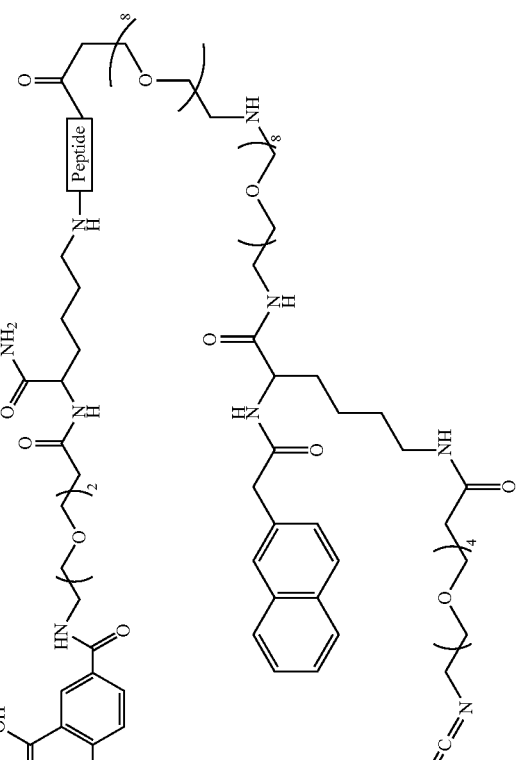 |

TABLE 3A-continued
Structures and molecular weights of compounds used in this study.
| Compound | MW (Da) | Structure |
|---|---|---|
| Rituximab-cHBL (Peptide-WPRWLEN) (SEQ ID NO: 1) | 3021.42 | 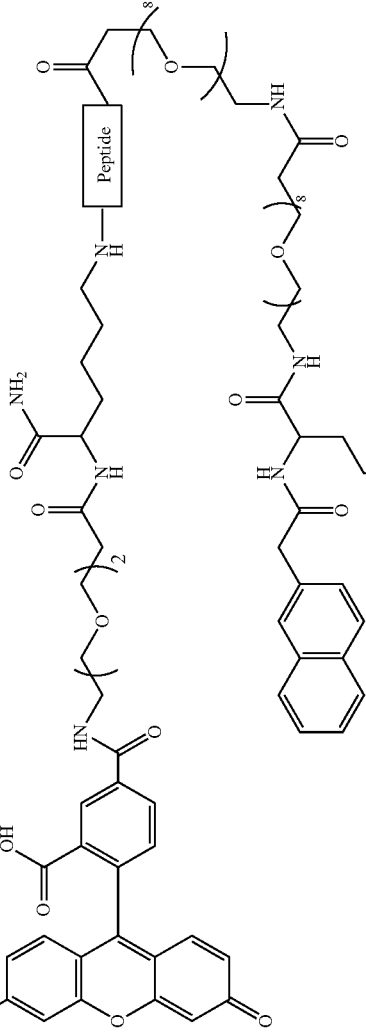 |
| Biotin-Napth | 1010.25 | 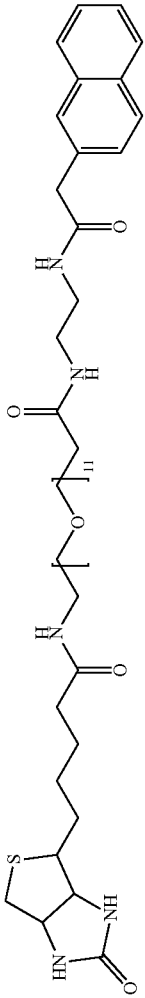 |

Figures 25A, 25B, 25C:
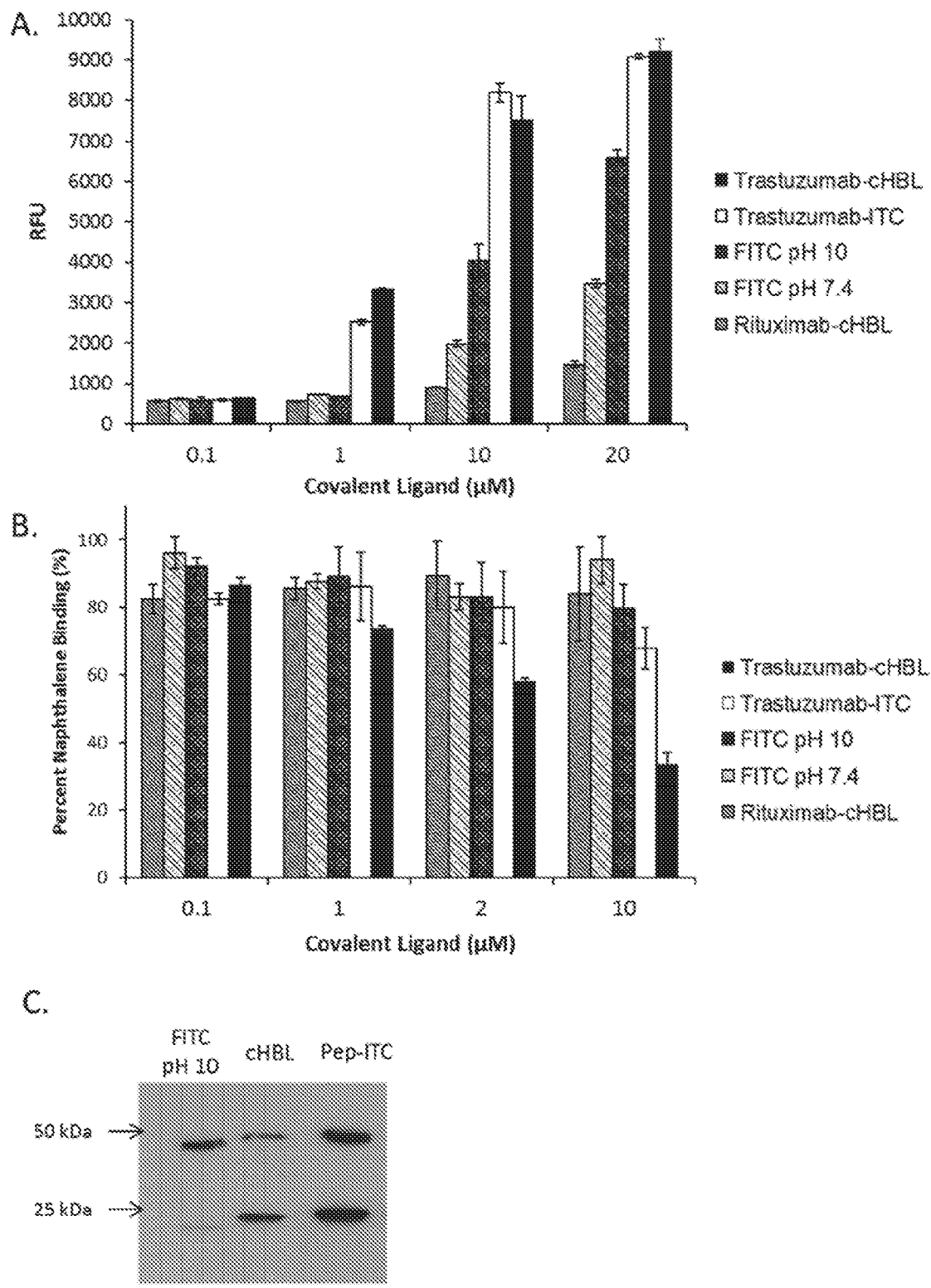

After demonstrating selective binding, we demonstrated that the NBS moiety was crucial for site specific conjugation to lysines near the NBS site. To prove specific conjugation of the cHBL to the lysines near the NBS pocket, we performed a competitive ELISA where naphthalene-biotin conjugates compete against the binding of cHBL to unoccupied NBS pockets. Naphthalene-biotin conjugate was added to trastuzumab previously incubated with cHBL molecules and then exposed to UV light to photocrosslink any bound naphthalene compounds into the NBS pocket. After UV exposure, a direct ELISA was performed using streptavidin-HRP to detect the presence of biotin. However, if the NBS site is already occupied with cHBL ligands or disrupted from binding by the presence of another ligand, the napht-biotin conjugate will not bind and the fluorescence signal should drop. In our assay, a percent conjugation was calculated between a positive control (trastuzumab without covalent ligands) and a negative control (PBS). The data shows that that trast-cHBL conjugated antibodies had significantly less naphthalene binding when compared with other ligand bound antibodies at 2 and 10 µM (p<0.01), demonstrating that trast-cHBL is specific to a lysine near the NBS (FIG. 25B). It is important to note that because a streptavidin signal would be observed at the same amount if one or both Fab arms are bound, any drop-in signal would require both Fab arms to be occupied with cHBLs, explaining why a complete inhibition of signal was not observed and only a very small of inhibition was observed below 2 µM, while the previous ELISA demonstrated binding at 1 µM. This result suggests that at 1 there is a 1:1 cHBL/antibody ratio. Overall, this data demonstrates that trast-cHBL specifically binds to a lysine near NBS pocket due to the specific bivalent binding of NBS and ABS targeting ligands in a concentration dependent manner.

Figure 26:
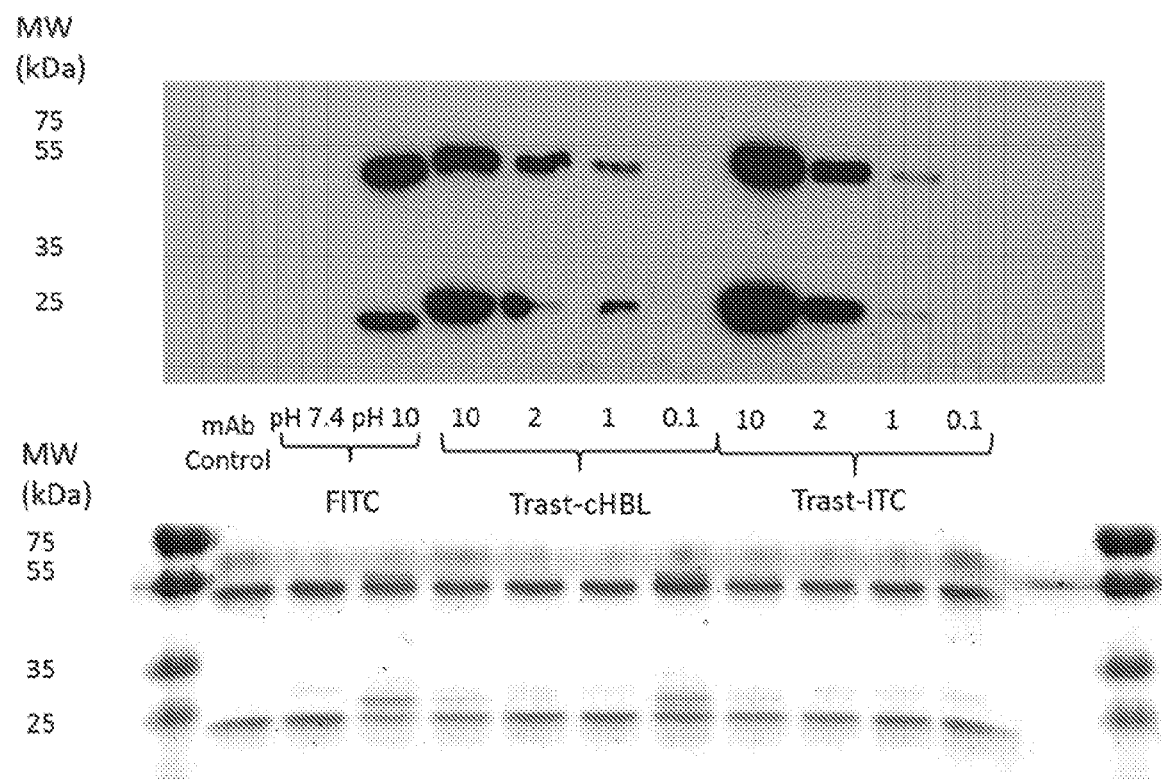

After demonstrating that this conjugation is occurring preferentially to lysines near the NBS, we further evaluated the specificity of this conjugation by demonstrating which chain on the IgGs cHBLs are conjugated by western blot. Since lysines near the NBS are only present on the light chain of trastuzumab, cHBLs should be selectively observed binding to the light chain, which is in contrast to non-specific conjugation, given that the heavy chain is both larger and contains more available lysines for conjugation. We observed that trast-cHBLs were preferentially conjugated to light chain (25 kDa) while trast-ITC was conjugated nearly equally to either heavy (50 kDa) or light chain on trastuzumab (FIG. 25C). Additionally, this conjugation was concentration dependent, although preferential binding to the light chain was not observed at higher (10 µM) concentrations (FIG. 26). Overall, the data demonstrates that trast-cHBLs, due to their innovative design, site-specifically conjugate to a lysine on the light chain of trastuzumab and using appropriate concentrations can form covalent interactions preferentially to a specific lysine.

Site Specific Attachment of cHBL Molecules Observed with LC-MS/MS

Figure 27:
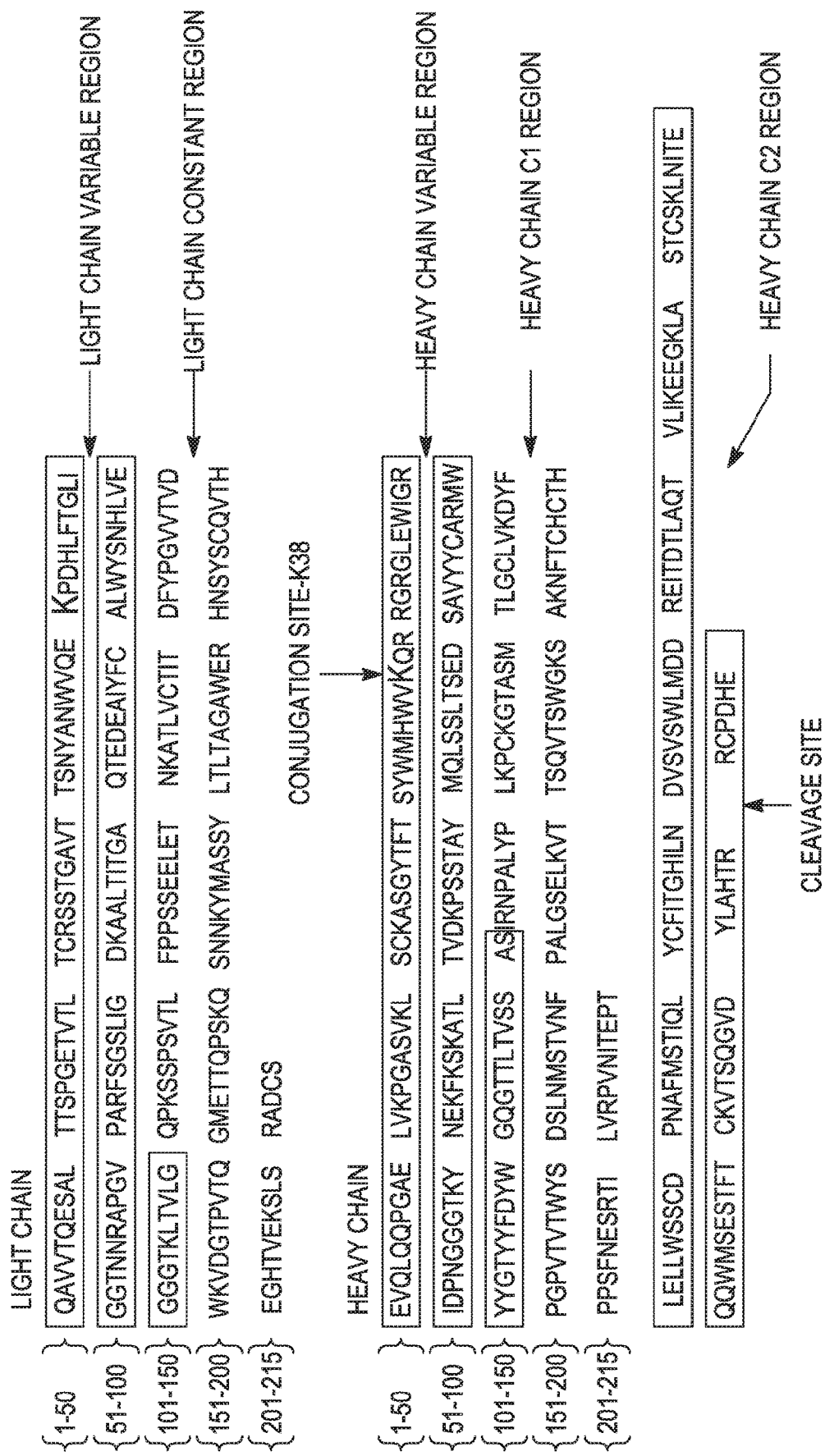
Figure 28:
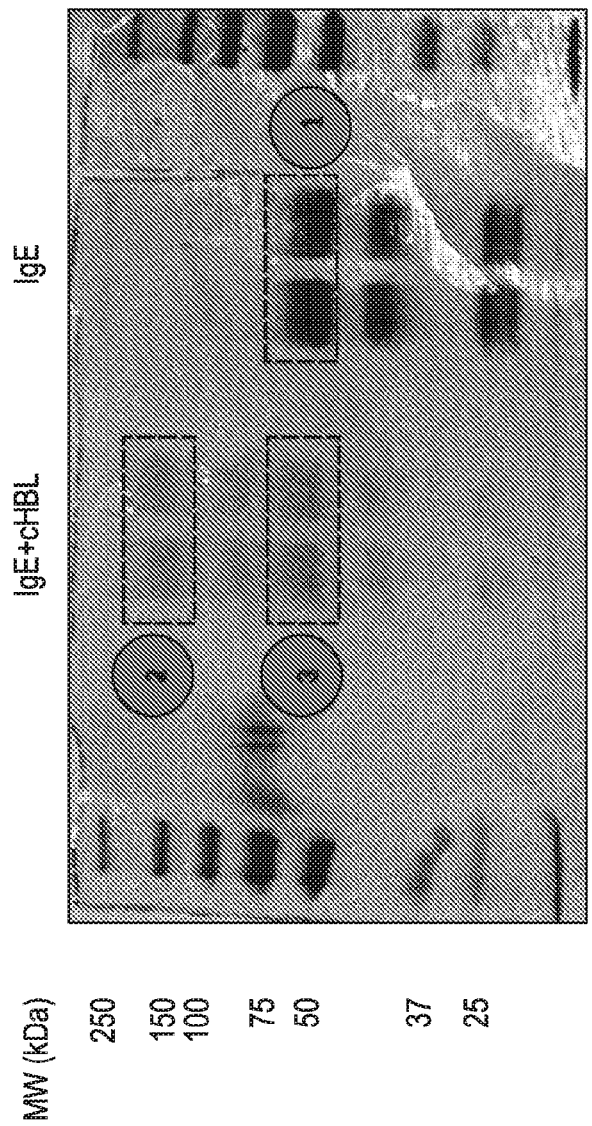
Figure 29:
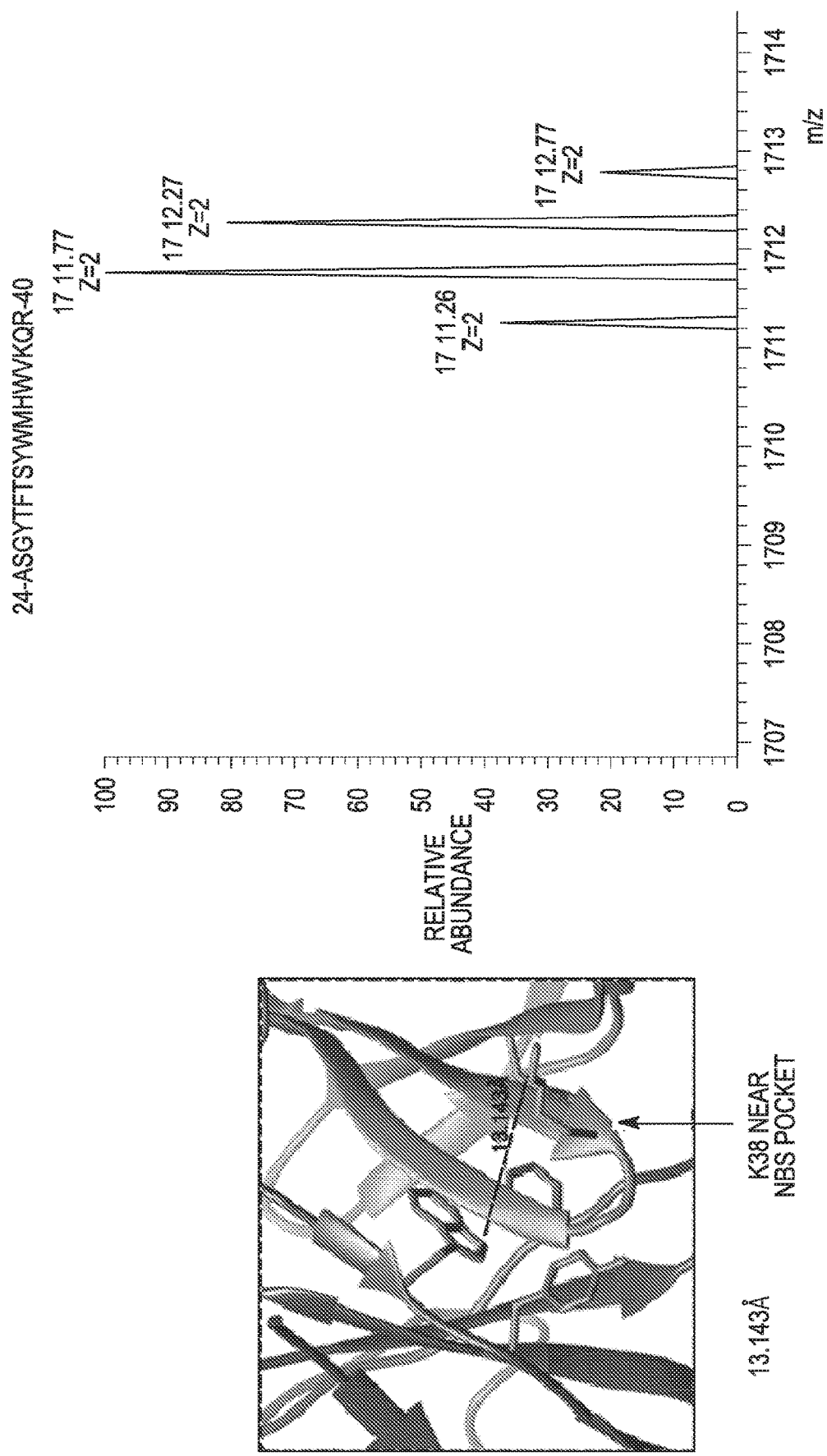

To determine the exact lysine side chain that is preferentially conjugated by a cHBL molecule, we performed liquid chromatography-tandem mass spectrometry (LC-MS/MS) on antibodies after incubating with cHBL molecules. We chose the DNP-cHBL to analyze extensively due the small number of lysines located proximal to the NBS on IgE$^{DNP}$ and the inherent optical properties of DNP facilitating sample preparation. We analyzed the crystal structures and primary sequence of IgE$^{DNP}$ and determined the locations of likely reactive lysine side chains located proximal to the NBS (FIG. 2D, FIG. 27). IgE$^{DNP}$ was conjugated with DNP-cHBL as before at 1 µM, purified, cleaved with papian, the Fab fragments isolated using SDS-PAGE gel extraction, and the bands trypanized for analysis with LC-MS/MS (FIG. 28, Table 7). We correlated these lysines with potential typsin peptide fragments for IgE$^{DNP}$ and using LC-MS/MS determined which peptide fragment was modified with cHBL molecules (FIGS. 35-38 Table 4). We observed two peaks in our analysis of cHBL conjugated IgE$^{DNP}$ that represent modified peptide fragments of the same peptide sequence, implying that K38 is covalently modified by DNP-cHBL molecules (FIG. 29 and Table 5). In particular, the presence of the modified peptide fragment (24-40) strongly suggests that K38 in the IgE$^{DNP}$ sequence is modified because addition to this lysine would prevent a typical trypsin cleavage site located next to K38. If this site were not modified, normal cleavage would occur and, as is seen in the control, only the fragment (24-38) would be observed, not (24-40). For further analysis of LC-MS/MS data see the Methods section. This data conclusively shows that DNP-cHBL site specifically conjugates a lysine side chain near the NBS.

TABLE 4

Peptide sequences of all possible trypsin fragments of IgE$^{DNP}$ Fab that contain a lysine. Note that some peptide sequences were expanded to next possible cleavage site to consider the possibility of DNP-cHBL modification preventing trypsin cleavage at reactive lysine.

| Reside | Peptide | MW (Da) | MW+ DNP-cHBL |
| --- | --- | --- | --- |
| 24-38 | ASGYTFTSYWMHWVK | 1862.85 | 3135.41 |
| 24-39 | ASGYTFTSYWMHWVKQ | 1990.9 | 3263.46 |
| 24-40 | ASGYTFTSYWMHWVKQR | 2147 | 3419.56 |
| 24-41 | ASGYTFTSYWMHWVKQRR | 2303.11 | 3575.67 |
| 24-43 | ASGYTFTSYWMHWVKQRRGR | 2516.23 | 3788.79 |
| 1-13 | EVQLQQPGAELVK | 1437.78 | 2710.34 |
| 1-19 | EVQLQQPGAELVKPGASVK | 1977.09 | 3249.65 |
| 1-23 | EVQLQQPGAELVKPGASVKLSCK | 2408.31 | 3680.87 |

TABLE 4-continued

Peptide sequences of all possible trypsin fragments of IgE$^{DNP}$ Fab that contain a lysine.
Note that some peptide sequences were expanded to next possible cleavage site to consider the
possibility of DNP-cHBL modification preventing trypsin cleavage at reactive lysine.

| Reside | Peptide | MW (Da) | MW+ DNP-cHBL |
|---|---|---|---|
| 20-23 | LSCK | 449.23 | 1721.79 |
| 20-37 | LSCKASGYTFTSYWMHWV | 2165.97 | 3438.53 |
| 51-59 | IDPNGGGTK | 857.42 | 2129.98 |
| 51-63 | IDPNGGGTKYNEK | 1391.67 | 2664.23 |

TABLE 5

MS-MS confirm specific conjugation of cHBL to specific lysine reside. Sequence for potential conjugation sites for both SPE-7 and Trastuzumab are given. For each potential peptide with and without cHBL conjugation m/z for two charge states are given. M/z values that were observed are given in parentheses. * Indicates that unconjugated mass was not observed due to conjugation blocking a trypsin cleavage site.

Figures 30A, 30B:
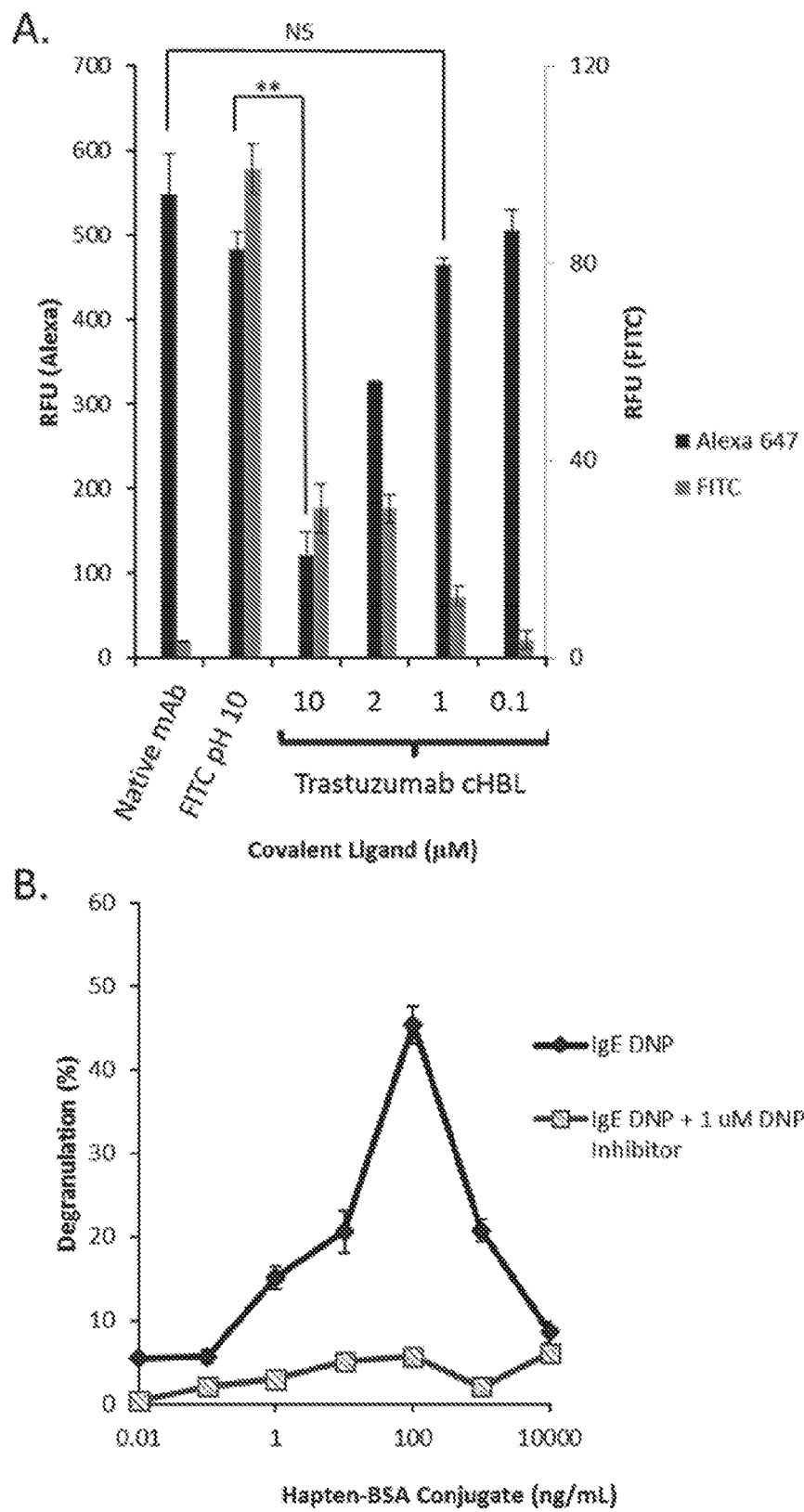

| Ig | Seq # | Sequence | cHBL? | MW(Da) | [M + 2]/2 | [M + 3]/3 |
|---|---|---|---|---|---|---|
| SPE-7 | 24-38 | ASGYTFTSYWMHWVK (SEQ ID NO: 3) | No | 1862.85 | 932.94 (932.94) | 622.29 |
|  |  |  | Yes | 3135.41 | 1569.22 | 1046.48 (1046.47) |
| SPE-7 | 24-40 | ASGYTFTSYWMHWVKQR (SEQ ID NO: 4) | No* | 2147.00 | 1075.01 | 717.01 |
|  |  |  | Yes | 3421.58 | 1711.77 (1711.77) | 1141.50 (1141.51) | cHBL Molecules Demonstrate Concentration Dependent Biological Activity for Both Antibody Tagging and Binding Inhibition The previous studies have demonstrated that cHBL's can specifically and selectively tag antibodies of interest under laboratory conditions. However, these cHBL molecules were designed to both tag and/or inhibit specific antibodies under physiological conditions, so in order to test this, we set up two different cellular experiments to observe how cHBL's interact in vitro. First, we incubated trast-cHBL molecules with trastuzumab at several concentrations in PBS, purified with membrane filtration and incubated the tagged antibodies at a constant concentration with a cell line that express the HER2/neu receptor on their surfaces, BT474. These cells were then washed and incubated with a secondary anti-human IgG tagged with an Alexa 647 fluorophore, washed and analyzed via flow cytometry for both Alexa 647 and FITC signals. Because the trastuzumab concentration is constant, any differences in the Alexa 647 signal would be due to cHBL molecules disrupting HER2-trastuzumab binding. Likewise, FITC signals demonstrate cHBL tagged trastuzumab binding HER2, meaning that these antibodies are tagged while not preventing HER2 binding, likely indicating either cHBL attachment specifically to one of the two Fab arms or a non-specific conjugation that does not alter ABS binding. The data demonstrates a predictable decrease in binding with increasing cHBL concentrations, as seen by a drop-in Alexa 647 signal when compared to native trastuzumab (FIG. 30). This drop at 10 μM was significant when compared to a 10 μM FITC control incubated at pH of 10 for the maximum non-specific attachment. This means that this drop-in signal is due to cHBL binding acting as a competitive inhibitor when bound near the ABS and not due to non-specific attachment disrupting antibody affinity for HER2.

The data also shows significant FITC signal for the 1, 2 and 10 μM data points, saturating at 2 μM (FIG. 30A, $p<0.05$). FITC signal suggests that trastuzumab has been conjugated with cHBL molecules on a single Fab region, while the other ABS site is free to bind HER2, tagging HER2 while not disrupting antigen binding at certain concentrations. In particular, it appears that FITC signal saturates at 2 μM, while retaining approximately 75% of HER2 binding. Additionally, there is approximately 50% of maximum FITC signal at 1 μM cHBL with no significant reduction in HER2 binding, as demonstrated by Alexa 647 signal (FIG. 30A, $p<0.05$). This is consistent with our previous results that at 1 μM there is 1:1 binding of cHBL/antibody for some of the antibodies, which would result in a FITC signal without disrupting trastuzumab binding. When the cHBL concentration is increased to 10 μM, however, HER2 binding drops drastically, while retaining similar FITC signal. This result indicates that cHBL molecules can tag antibodies of interest under physiological conditions and retain their antigen binding or can inhibit antigen binding with higher cHBL concentrations. This means that cHBL molecules can be used to either inhibit or tag antibodies specifically simply by varying cHBL concentration.

We further explored the inhibitory capabilities of these cHBL molecules in a more biologically relevant system using the DNP-$IgE^{DNP}$ system. This system models the IgE-dependent degranulation reaction that occurs on the surfaces of mast cells when allergy specific IgEs multivalently bind an allergen protein. To demonstrate the ability of cHBL molecules to inhibit antibody binding in physiologically relevant conditions, DNP-cHBL molecules were incubated with rat basophil leukemia 2H3 cells (RBL) that had bound IgE$^{DNP}$ on their cell surfaces for 24 hours at 1 µM in cell culture media (FIG. 30B). Cells were then washed to remove unbound cHBL's and degranulation was triggered with bovine serum albumin that had been covalently modified with several DNP molecules (DNP-BSA) at varying concentrations. At all allergen concentrations, the cHBL incubated cells demonstrated near base levels of degranulation. This result is significant for two reasons. First, because these molecules were incubated in cell culture media containing various proteins and cytokines and washed thoroughly after incubation with a washing buffer, the decrease in degranulation demonstrates covalent attachment to IgE molecules in crude, biologically relevant mixtures. Second, cHBL molecules can be used as effective inhibitors for antibody interactions at proper concentrations. Taken together, these cHBL studies revealed the potential use these molecules could have both for site specific antibody tagging and inhibition.

HBI Molecule Design Increases Avidity

To demonstrate the importance of a bivalent system for binding, we performed fluorescence quenching binding assays on HBI molecules (e.g. cHBI molecules synthesized without an ITC moiety). To observe quenching, we tagged penicilloyl molecules with a dinitrophenol (DNP) group; the dansyl molecules required no DNP addition, as dansyl itself quenches fluorescence from tryptophan residues. We synthesized four molecules, a dansyl control, a dansyl-napht HBI, a penicilloyl-DNP control, and a penicilloyl-DNP HBI and tested them for binding with a monoclonal antibody for either penicillin or dansyl (Table 6, Table 2). The results demonstrate a nearly fivefold and 20-fold increase respectively in observed $K_d$ for the dansyl and penicilloyl molecules when the NBS ligand is added. This increase in avidity for the HBI indicates bivalent binding is occurring. It is important to note that due to the lack of commercially produced penicilloyl specific antibodies, we used a penicillin G specific antibody (e.g. specific to the penicillin molecule with an intact beta lactam ring) to test binding of the penicilloyl molecules. This explains why the monovalent affinity was measured in the micromolar range and why a bivalent approach more drastically increased apparent affinity.

TABLE 6

Dansyl and penicillin cHBI molecules.

| Compound | Structure | MW (Da) |
|---|---|---|
| Dansyl cHBI | 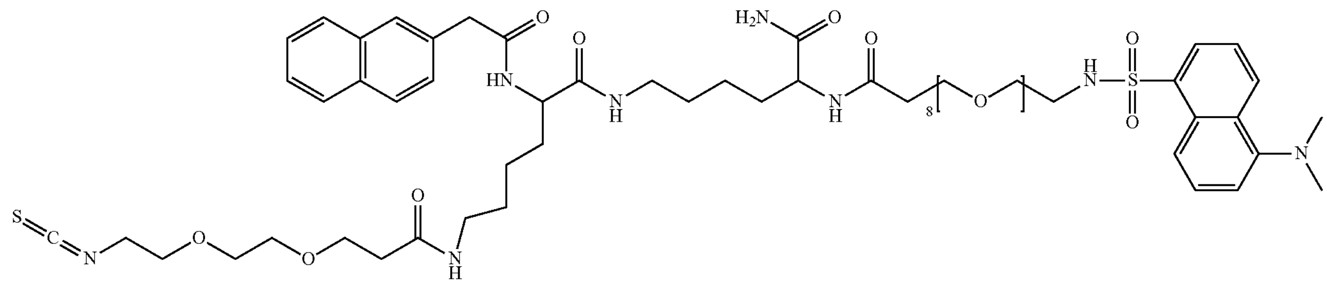 | 1298.62 |
| Penicillioyl cHBI | 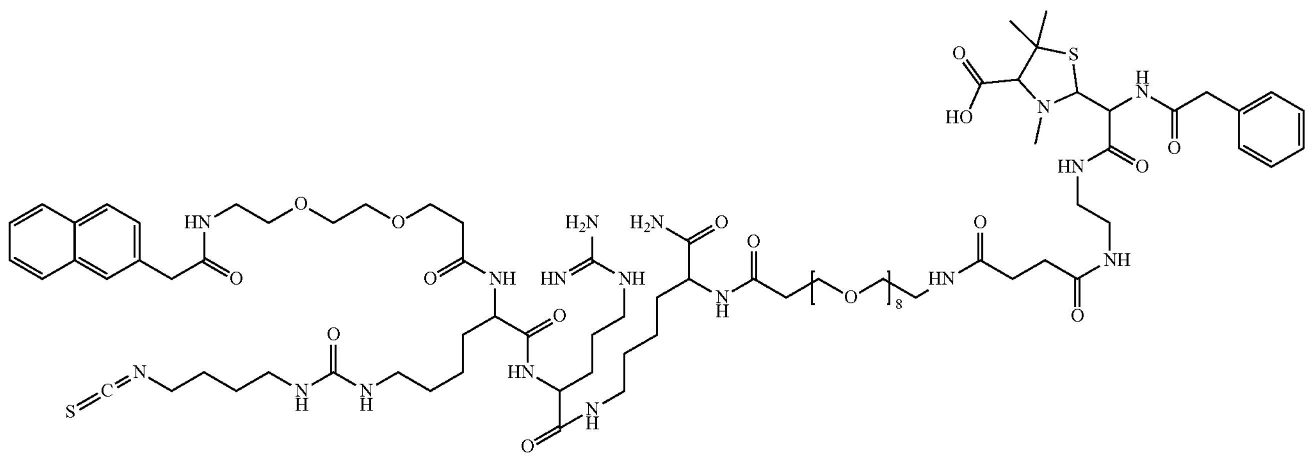 | 1841.91 |

TABLE 7

Molecular weights of IgE Fab fragments using both SDS-PAGE and MALDI. Note apparent increase in molecular weight for band 3, indicating DNP attachment, while band 1 and 2 were unconjugated full length IgE and Fab.

| Band | MW, Da (SDS-PAGE) | MW, Da (MALDI) |
|---|---|---|
| 1 | ≈55000 | ≈58000 |
| 2 | ≈150000 | ≈60000 |
| 3 | ≈55000 | ≈58000 | cHBIs Specifically Bind Target IgEs

Figures 31A, 31B, 31C:
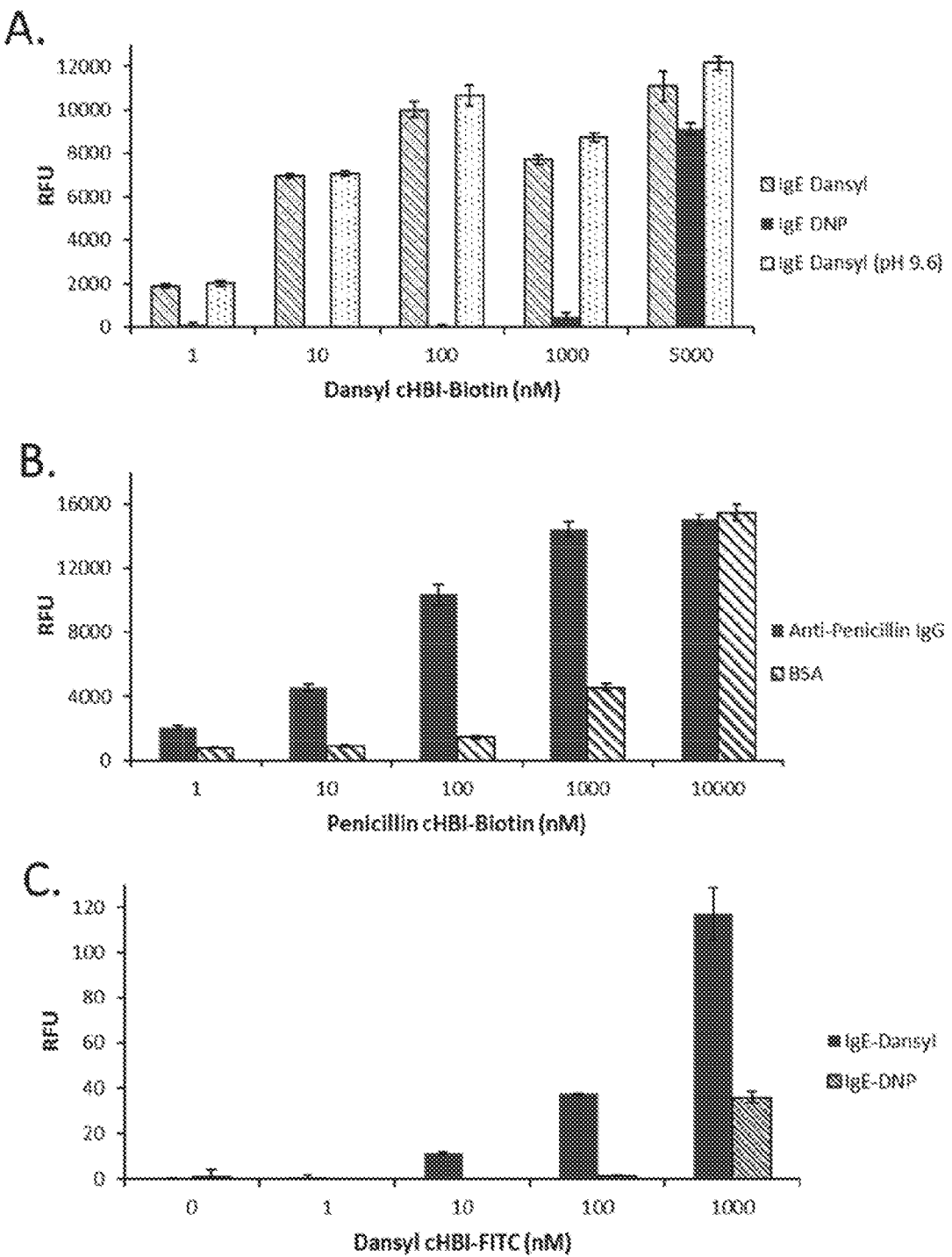

To assert that any degranulation inhibition from cHBIs is due to the proposed IgE binding mechanism rather than a non-specific cellular disruption or another phenomenon, we assessed the level of specific conjugation of cHBI molecules to a target antibody using both ELISA and flow cytometry. To quantify conjugation of cHBI molecules, both penicilloyl and dansyl cHBI were synthesized with biotin tags and incubated with specific antibodies, purified with membrane filtration and characterized for cHBI binding using ELISA (Table 2). Dansyl-biotin cHBIs demonstrated a near saturated level of conjugation at concentrations as low as 10 nM at pH 7.4 (FIG. 31A). We also assessed conjugation at an increased pH of 9.6 as a positive control as well as conjugation to an orthogonal IgE specific to the small molecule DNP as a negative control. This demonstrates that specific conjugation occurs up to 5000 nm when a predictable level of non-specific conjugation occurs, likely due to the napht interaction with the conserved NBS. Additionally, there was no significant difference between pH 7.4 and pH 9.6 for the cHBI molecules, indicating a high level of specific binding. We also performed a similar ELISA with a penicilloyl cHBI that was tagged with a biotin using a monoclonal anti-Penicillin IgG (Table 2, FIG. 31B). Even though the monovalent affinity of penicilloyl for the anti-penicillin IgG was 20 μM, we observed maximum conjugation at 1 μM and little conjugation to a bovine serum albumin control, likely due to bivalent effects (FIG. 31B). Finally, to confirm that this specific conjugation can occur on IgEs when bound to FcεRI, rat basophil leukemia (RBL) cells were primed with either $IgE^{dansyl}$ or $IgE^{DNP}$ and then incubated with $cHBI^{dansyl}$ with fluorescein (FITC) tags then analyzed with flow cytometry (Table 2, FIG. 31C). The data indicates that cHBI molecules bind significantly more to $IgE^{dansyl}$ rather than $IgE^{DNP}$ on the surfaces of RBL cells at for concentration 10, 100 and 1000 nM, indicating selective binding (FIG. 31C, p<0.01). These results indicate specific attachment of cHBI molecules in the nanomolar range.

cHBIs Demonstrate Degranulation Inhibition In Vitro with monoclonal antibodies

Figures 32A, 32B, 32C:
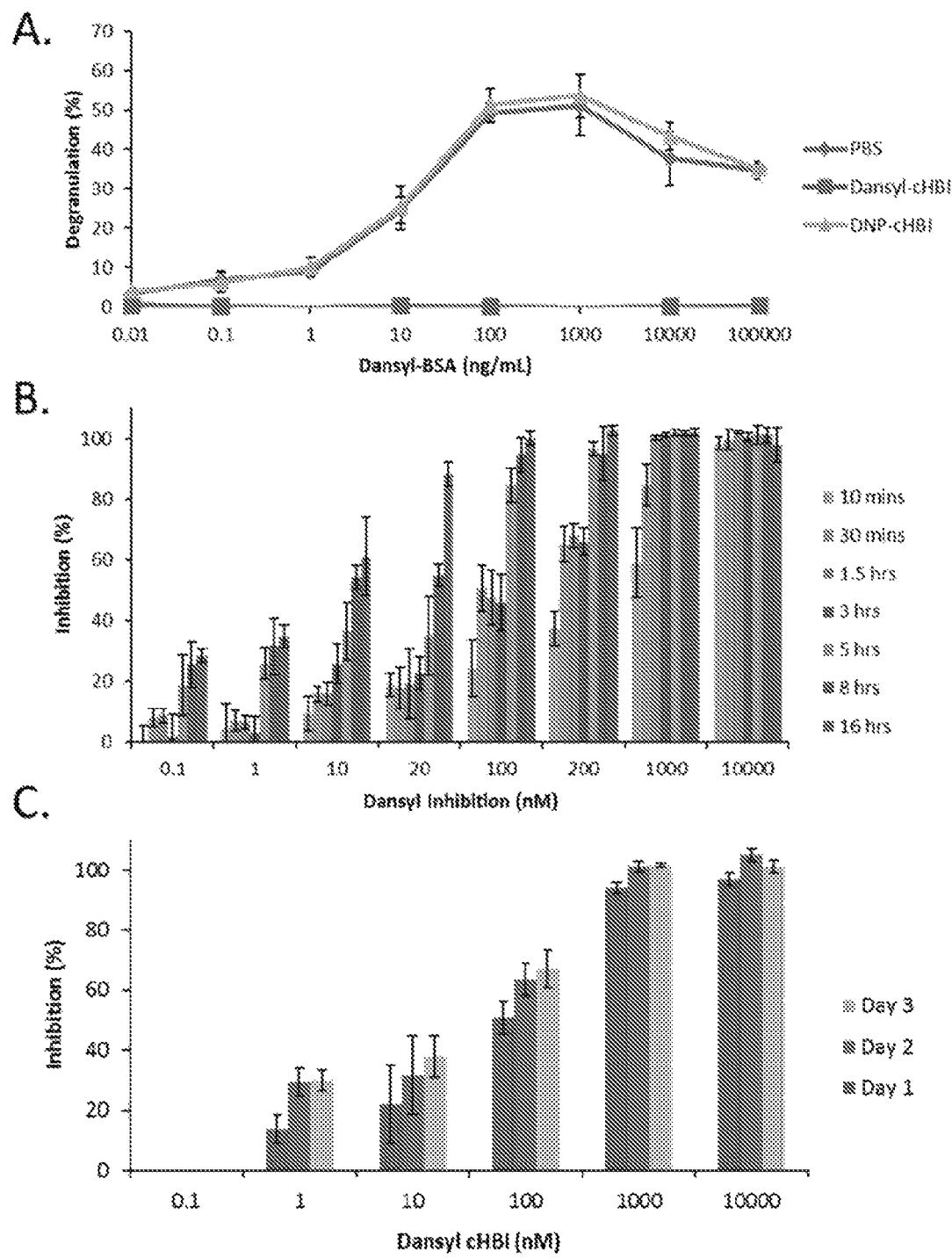
FIG. 32A-32C. Dansyl cHBIs inhibit degranulation in vitro using RBL-2H3 cells. Degranulation assay results from RBL cells sensitized with IgE$^{dansyl}$, incubated for 5 hours with 1 µM of either DNP or dansyl cHBI or a PBS control, then challenged with varying concentrations of danysl-BSA (A). Percent degranulation inhibition for dansyl cHBI at various incubation times and concentrations when challenged with 100 ng/mL dansyl-BSA. (B). RBL cells were sensitized and then incubated with dansyl cHBI's at varying concentrations overnight, washed with buffer and then challenged on consecutive days with 100 ng/mL dansyl-BSA (C).

After confirming the specific covalent attachment of cHBI molecules to allergy reactive IgE's, we next sought to demonstrate inhibition of allergy reactions using an in vitro system. We tested cHBIs with a well-established degranulation assay using rat basophil leukemia (RBL) cells with monoclonal IgEs and haptenized bovine serum albumin (BSA) as the IgE/allergen. As demonstrated by FIG. 32A, when dansyl cHBI was incubated with $IgE^{dansyl}$ primed RBL cells at a constant concentration of 1 μM, there was a complete inhibition of degranulation responses over a wide range of dansyl-BSA allergen stimulation. A cHBI molecule specific to an orthogonal molecule, dinitrophenol (DNP), did not inhibit degranulation responses to dansyl-BSA, demonstrating the specificity of these inhibitors (FIG. 32A). To further confirm degranulation inhibition, we observed a marked decrease in phosphorylation of Bruton's tyrosine kinase, a well-established marker for RBL and mast cell degranulation activation. Likewise, cHBI molecules inhibited degranulation much more effectively than HBIs or hapten-ITC conjugates likely due to washing steps prior to allergen incubation causing most unconjugated molecules to be removed, demonstrating the necessity of all three moieties for proper cHBI design. Furthermore, these molecules inhibit degranulation over a wide number of experimental conditions, demonstrating their potential clinical versatility. The dansyl cHBI was able to effectively inhibit degranulation at concentrations as low as 20 nM and in as rapidly as 10 minutes (with a dose of 1000 nM, FIG. 32B). The cHBI molecules have long lasting inhibitory effects as well. As demonstrated by FIG. 32C, even after washing away the initial cHBI dose, there was no significant effect in the inhibitory effect of dansyl-cHBI's even after a 72-hour incubation in cell culture media. This indicates that cHBI molecules could provide long lasting inhibition of IgE mediated degranulation to drugs with only a single dose.

cHBIs Inhibit Degranulation to Mouse Sera Primed RBL Cells

Figure 33:
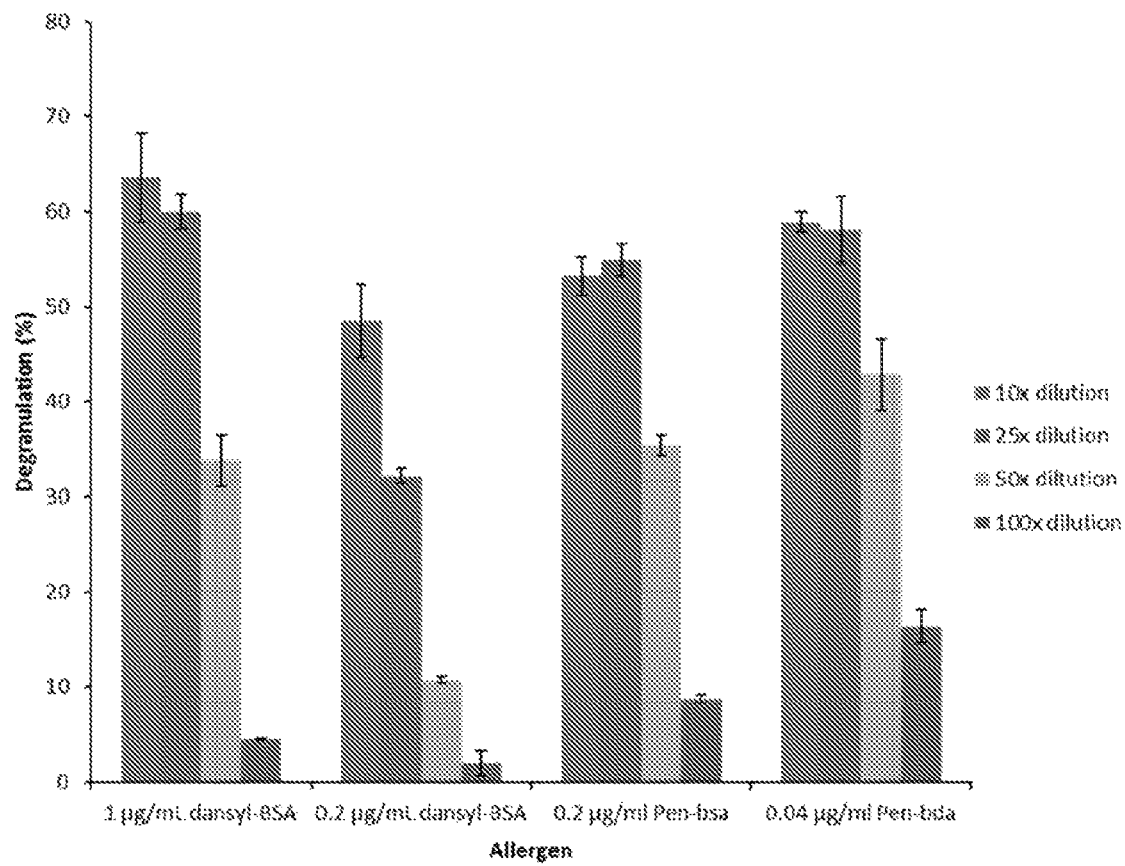
FIG. 33. Pooled mouse sera from 5 mice sensitized to either dansyl-OVA or Pen-OVA were used to sensitize RBL cells at various dilutions of sera. Degranulation was observed to hapten-BSA conjugates.

To further examine the cHBIs inhibitory characteristics in a more physiologically relevant in vitro system, we primed RBL cells with serum taken from mice sensitized to ovalbumin (OVA) that had been haptenized with either dansyl or penicillin G (see Methods section). After incubating RBL cells with the reactive sera, degranulation was triggered with either dansyl-BSA or penicilloyl-BSA conjugates confirming the presence of hapten specific IgEs in the sera (FIG. 33). Both the dansyl and penicilloyl cHBI demonstrated significant inhibition of degranulation when exposed to various concentrations of their respective hapten-BSA allergen ($p<10^{-4}$, FIG. 34A). We also varied inhibitor concentrations of both cHBI and HBI molecules to dansyl and penicilloyl to determine optimal concentration ranges. As demonstrated by FIG. 34B, cHBI molecules to both haptens inhibited degranulation in a significant fashion down to 100 nM (p<0.01). The optimal inhibition occurred between 1 and 10 μM for both dansyl and penicilloyl, with a >95% and >80% maximum inhibition respectively (FIG. 34B). Finally, the cHBI's demonstrated a significantly higher inhibition than HBI's at every inhibitor concentration except for the lowest concentration point for dansyl and the lowest two points for penicilloyl, demonstrating the importance of the ITC domain (p<0.05, FIG. 34B). This result demonstrates that cHBI molecules can prevent degranulation to a clinically relevant drug, penicillin, and that cHBI molecules maintain inhibitory characteristics even to a more physiologically relevant polyclonal IgE mixture. Finally, to further evaluate cHBIs as a potential clinical tool, these molecules were administered to mice that had been previously sensitized to either dansyl or penicillin to demonstrate in-vivo inhibition of degranulation.

Pharmaceutical Formulations

The compounds described herein can be used to prepare therapeutic pharmaceutical compositions, for example, by combining the compounds with a pharmaceutically acceptable diluent, excipient, or carrier. The compounds may be added to a carrier in the form of a salt or solvate. For example, in cases where compounds are sufficiently basic or acidic to form stable nontoxic acid or base salts, administration of the compounds as salts may be appropriate. Examples of pharmaceutically acceptable salts are organic acid addition salts formed with acids that form a physiologically acceptable anion, for example, tosylate, methanesulfonate, acetate, citrate, malonate, tartrate, succinate, benzoate, ascorbate, α-ketoglutarate, and b-glycerophosphate. Suitable inorganic salts may also be formed, including hydrochloride, halide, sulfate, nitrate, bicarbonate, and carbonate salts.

Pharmaceutically acceptable salts may be obtained using standard procedures well known in the art, for example by reacting a sufficiently basic compound such as an amine with a suitable acid to provide a physiologically acceptable ionic compound. Alkali metal (for example, sodium, potassium or lithium) or alkaline earth metal (for example, calcium) salts of carboxylic acids can also be prepared by analogous methods.

The compounds of the formulas described herein can be formulated as pharmaceutical compositions and administered to a mammalian host, such as a human patient, in a variety of forms. The forms can be specifically adapted to a chosen route of administration, e.g., oral or parenteral administration, by intravenous, intramuscular, topical or subcutaneous routes.

The compounds described herein may be systemically administered in combination with a pharmaceutically acceptable vehicle, such as an inert diluent or an assimilable edible carrier. For oral administration, compounds can be enclosed in hard or soft shell gelatin capsules, compressed into tablets, or incorporated directly into the food of a patient's diet. Compounds may also be combined with one or more excipients and used in the form of ingestible tablets, buccal tablets, troches, capsules, elixirs, suspensions, syrups, wafers, and the like. Such compositions and preparations typically contain at least 0.1% of active compound. The percentage of the compositions and preparations can vary and may conveniently be from about 0.5% to about 60%, about 1% to about 25%, or about 2% to about 10%, of the weight of a given unit dosage form. The amount of active compound in such therapeutically useful compositions can be such that an effective dosage level can be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid and the like; and a lubricant such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propyl parabens as preservatives, a dye and flavoring such as cherry or orange flavor. Any material used in preparing any unit dosage form should be pharmaceutically acceptable and substantially non-toxic in the amounts employed. In addition, the active compound may be incorporated into sustained-release preparations and devices.

The active compound may be administered intravenously or intraperitoneally by infusion or injection. Solutions of the active compound or its salts can be prepared in water, optionally mixed with a nontoxic surfactant. Dispersions can be prepared in glycerol, liquid polyethylene glycols, triacetin, or mixtures thereof, or in a pharmaceutically acceptable oil. Under ordinary conditions of storage and use, preparations may contain a preservative to prevent the growth of microorganisms.

Pharmaceutical dosage forms suitable for injection or infusion can include sterile aqueous solutions, dispersions, or sterile powders comprising the active ingredient adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions, or by the use of surfactants. The prevention of the action of microorganisms can be brought about by various antibacterial and/or antifungal agents, for example, parabens, chlorobutanol, phenol, sorbic acid, thimerosal, and the like. In many cases, it will be preferable to include isotonic agents, for example, sugars, buffers, or sodium chloride. Prolonged absorption of the injectable compositions can be brought about by agents delaying absorption, for example, aluminum monostearate and/or gelatin.

Sterile injectable solutions can be prepared by incorporating the active compound in the required amount in the appropriate solvent with various other ingredients enumerated above, as required, optionally followed by filter sterilization. In the case of sterile powders for the preparation of sterile injectable solutions, methods of preparation can include vacuum drying and freeze drying techniques, which yield a powder of the active ingredient plus any additional desired ingredient present in the solution.

For topical administration, compounds may be applied in pure form, e.g., when they are liquids. However, it will generally be desirable to administer the active agent to the skin as a composition or formulation, for example, in combination with a dermatologically acceptable carrier, which may be a solid, a liquid, a gel, or the like.

Useful solid carriers include finely divided solids such as talc, clay, microcrystalline cellulose, silica, alumina, and the like. Useful liquid carriers include water, dimethyl sulfoxide (DMSO), alcohols, glycols, or water-alcohol/glycol blends, in which a compound can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using a pump-type or aerosol sprayer.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user.

Examples of dermatological compositions for delivering active agents to the skin are known to the art; for example, see U.S. Pat. No. 4,992,478 (Geria), U.S. Pat. No. 4,820,508 (Wortzman), U.S. Pat. No. 4,608,392 (Jacquet et al.), and U.S. Pat. No. 4,559,157 (Smith et al.). Such dermatological compositions can be used in combinations with the compounds described herein where an ingredient of such compositions can optionally be replaced by a compound described herein, or a compound described herein can be added to the composition.

Useful dosages of the compounds described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.). The amount of a compound, or an active salt or derivative thereof, required for use in treatment will vary not only with the particular compound or salt selected but also with the route of administration, the nature of the condition being treated, and the age and condition of the patient, and will be ultimately at the discretion of an attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently formulated in unit dosage form; for example, containing 5 to 1000 mg, conveniently 10 to 750 mg, most conveniently, 50 to 500 mg of active ingredient per unit dosage form. In one embodiment, the invention provides a composition comprising a compound of the invention formulated in such a unit dosage form.

The compound can be conveniently administered in a unit dosage form, for example, containing 5 to 1000 mg/m$^2$, conveniently 10 to 750 mg/m$^2$, most conveniently, 50 to 500 mg/m$^2$ of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The compounds described herein can be effective anti-tumor agents and have higher potency and/or reduced toxicity as compared to XK 469. Preferably, compounds of the invention are more potent and less toxic than (R) XK 469, and/or avoid a potential site of catabolic metabolism encountered with XK469, i.e., have a different metabolic profile than XK469.

The invention provides therapeutic methods of treating cancer in a mammal, which involve administering to a mammal having cancer an effective amount of a compound or composition described herein. A mammal includes a primate, human, rodent, canine, feline, bovine, ovine, equine, swine, caprine, bovine and the like. Cancer refers to any various type of malignant neoplasm, for example, colon cancer, breast cancer, melanoma and leukemia, and in general is characterized by an undesirable cellular proliferation, e.g., unregulated growth, lack of differentiation, local tissue invasion, and metastasis.

The ability of a compound of the invention to treat cancer may be determined by using assays well known to the art. For example, the design of treatment protocols, toxicity evaluation, data analysis, quantification of tumor cell kill, and the biological significance of the use of transplantable tumor screens are known. In addition, ability of a compound to treat cancer may be determined using the Tests as described below.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Figure 3A:
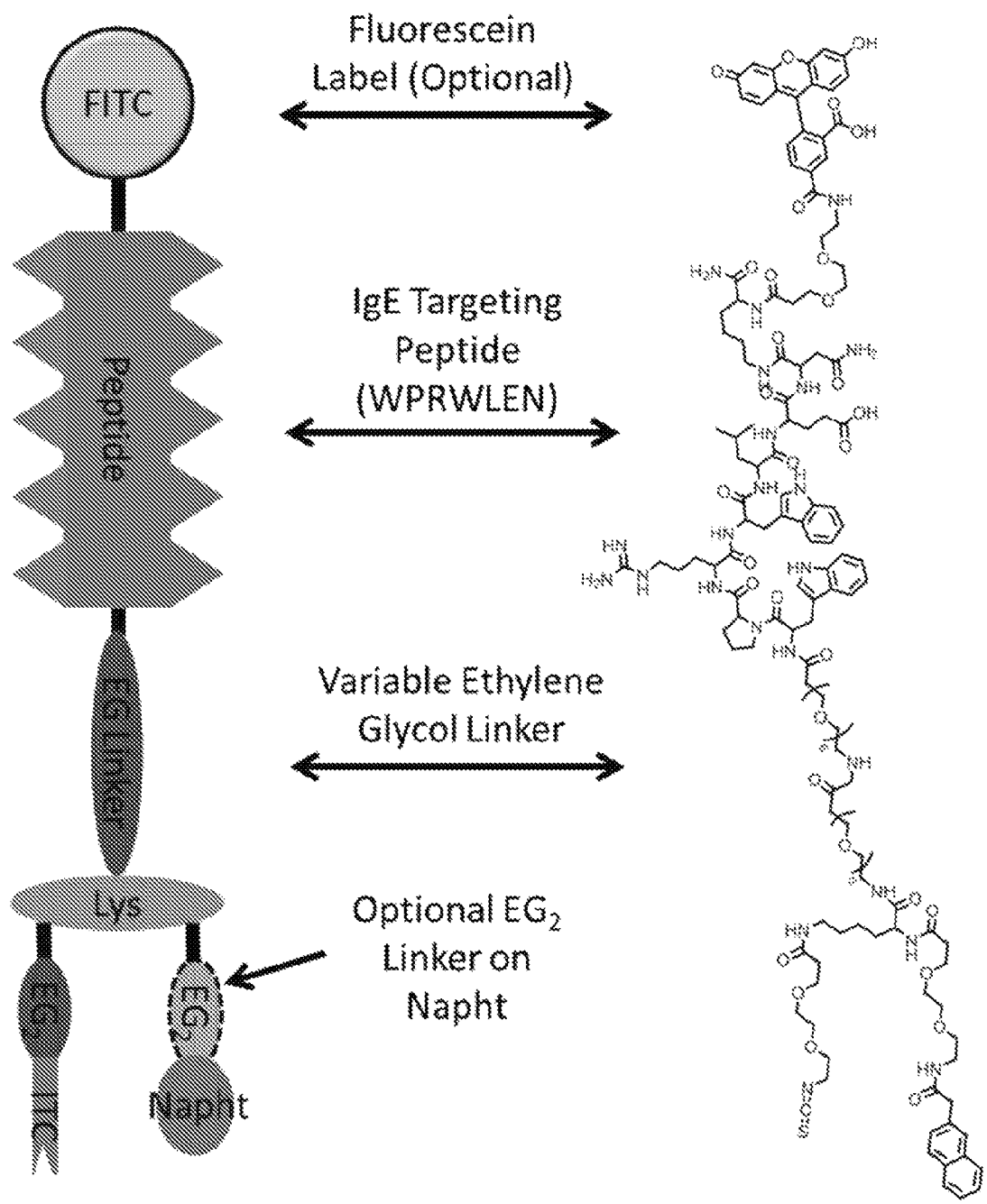
FIG. 3A-3C. Design of Covalent Heterobivalent Inhibitor (cHBI) demonstrating IgE targeting peptide (targeting sequence (WPRWLEN; SEQ ID NO: 1) that binds to Rituximab is shown as an example), EG linkers, Napht NBS targeting element and ITC covalent binder in A. Bivalent binding of cHBI to Ig molecule shown in B., and the covalent conjugation to lysine side chain near NBS site shown in C.
Figures 3B, 3C:
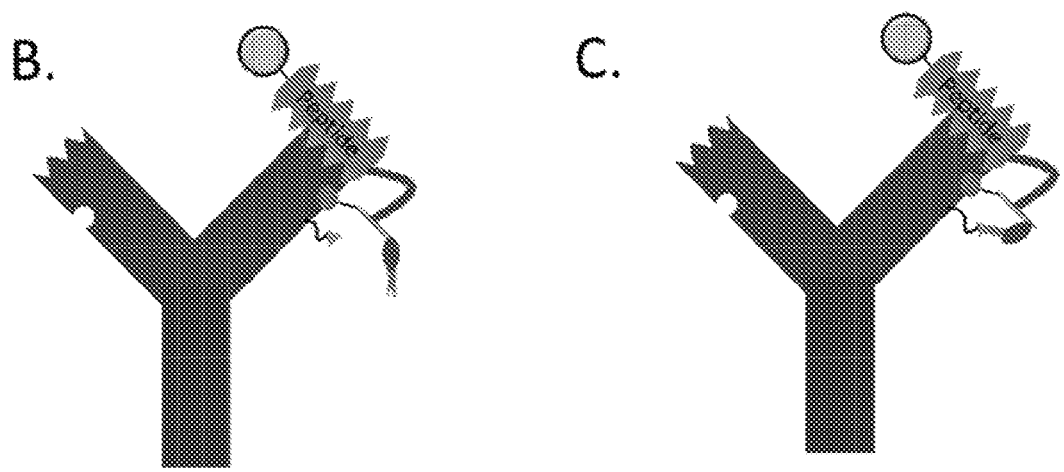
Figures 4A, 4B:
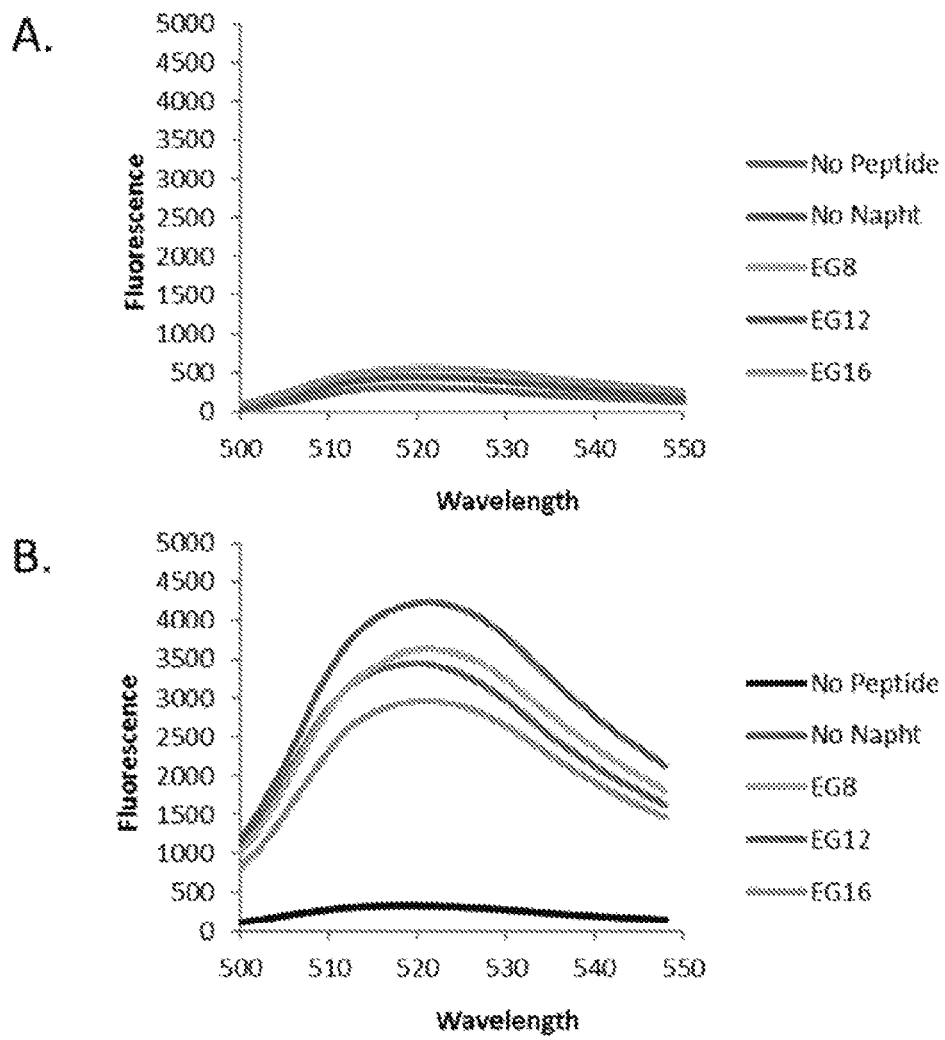
FIG. 4A-4B. Attachment of various Trastuzumab cHBI's with fluorescein tags and Trastuzumab binding peptide (LLGPYELWELSH (SEQ ID NO: 2), $K_d$=1.2 µM) with different linker lengths to either Rituximab (A) or Trastuzumab (B).
Figures 5A, 5B:
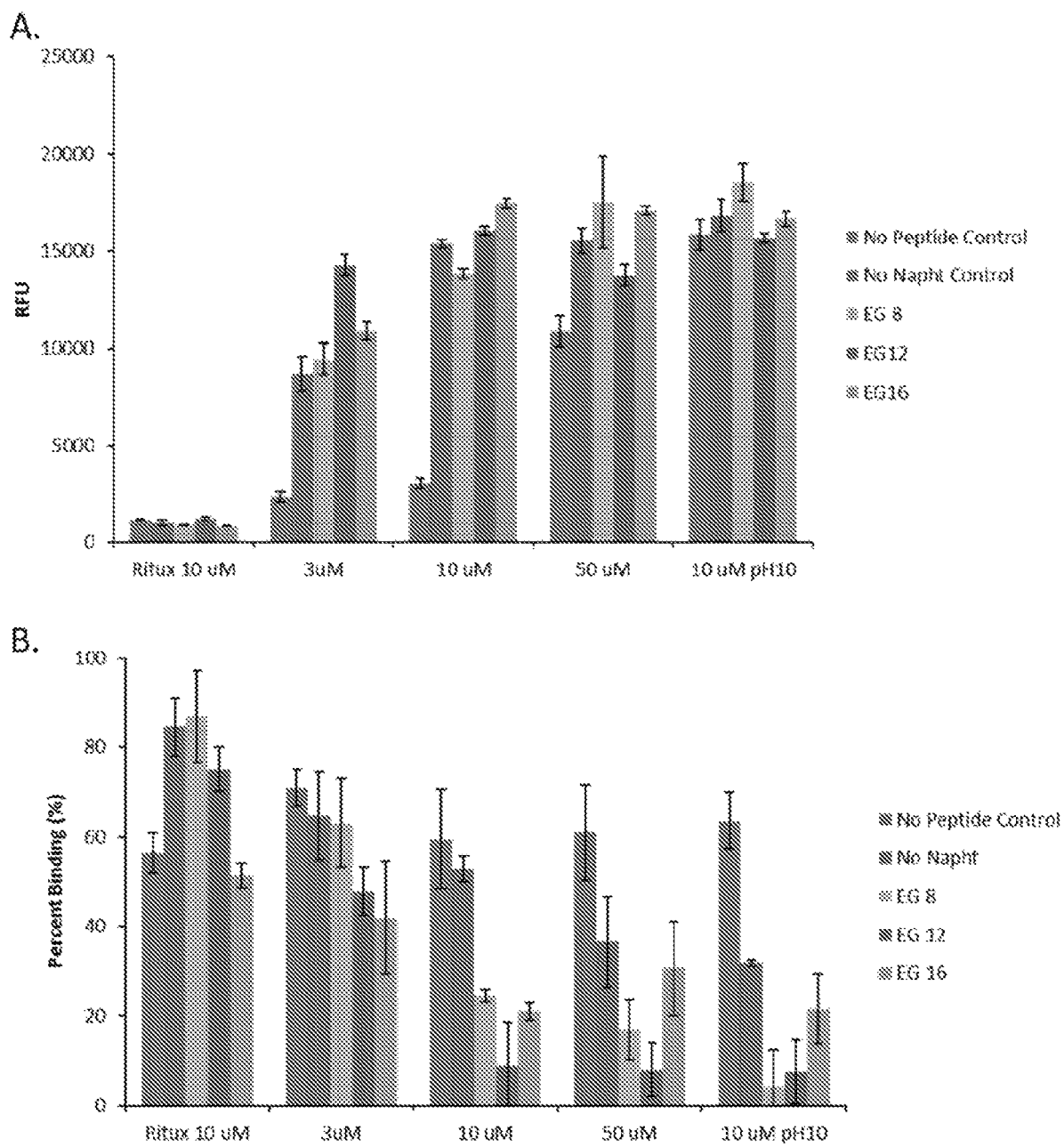
FIG. 5A-5B. Trastuzumab cHBI's demonstrate specific attachment to Trastuzumab at varying concentrations using ELISA (A). Competitive inhibition of Napht binding was demonstrated after incubation with cHBI's using ELISA (B).
Figure 6:
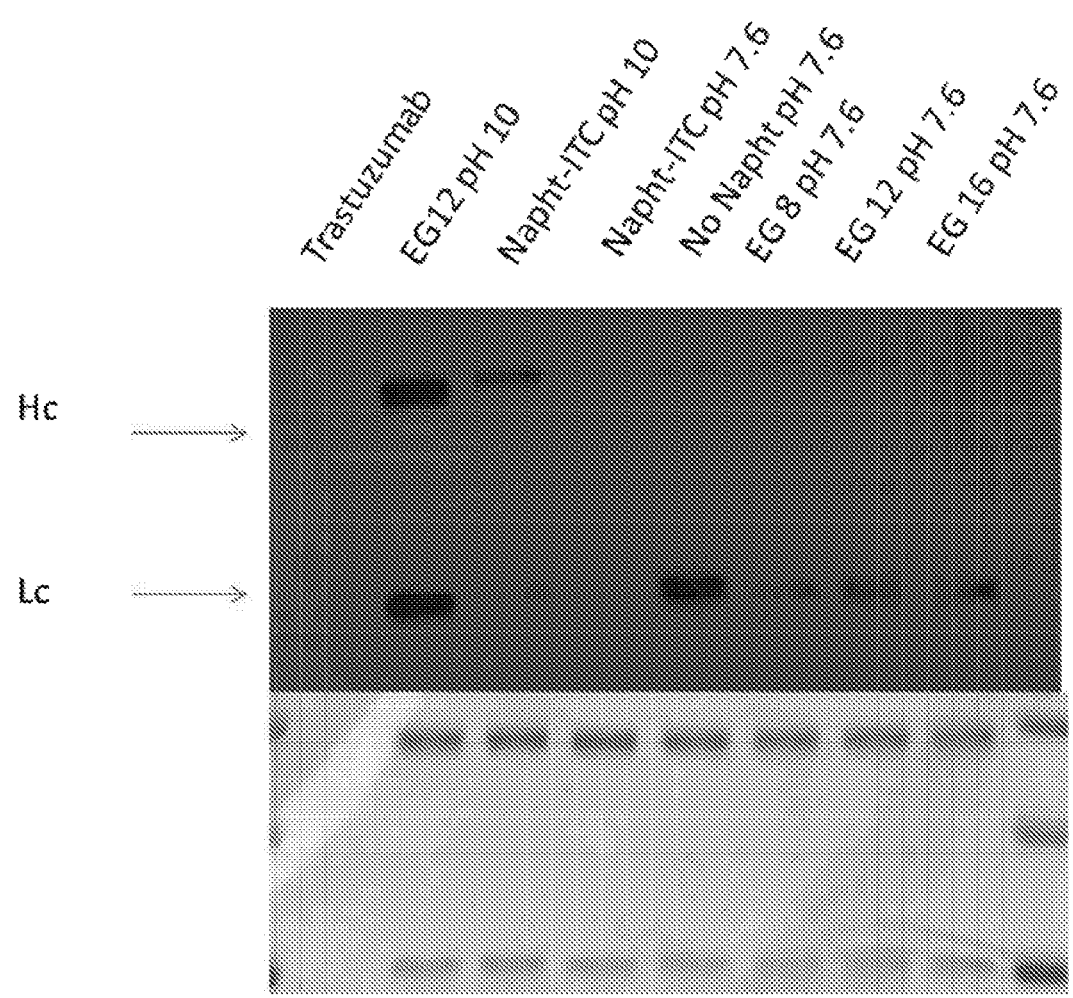
FIG. 6. Western blot demonstrates selective attachment of Trastuzumab cHBI's to light chain of Trastuzumab. SDS PAGE gel shown below as control.
Figure 7:
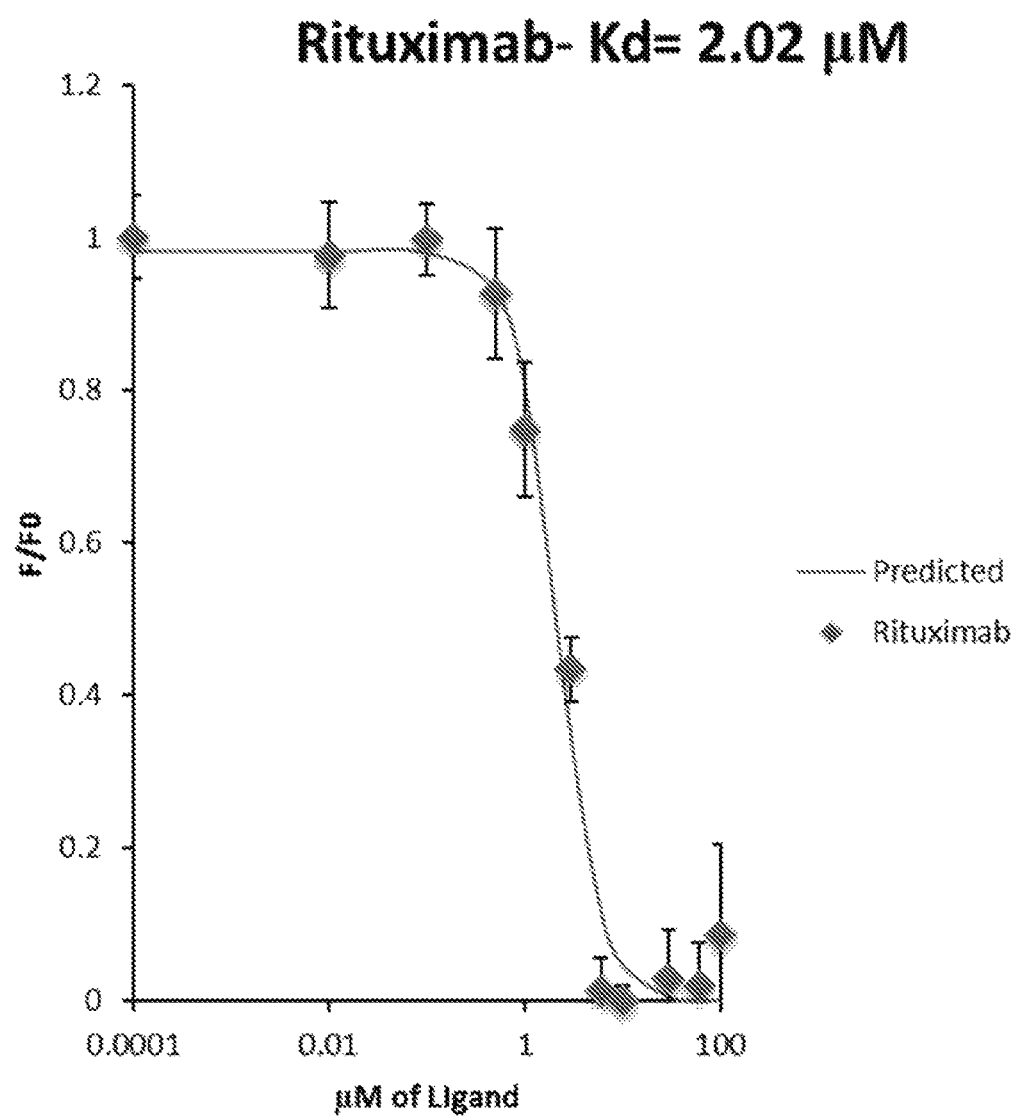
FIG. 7. Fluorescence quenching of Rituximab binding peptide (WPRWLEN (SEQ ID NO: 1)) with Rituximab. $K_d$=2.02 µM.
Figure 8:
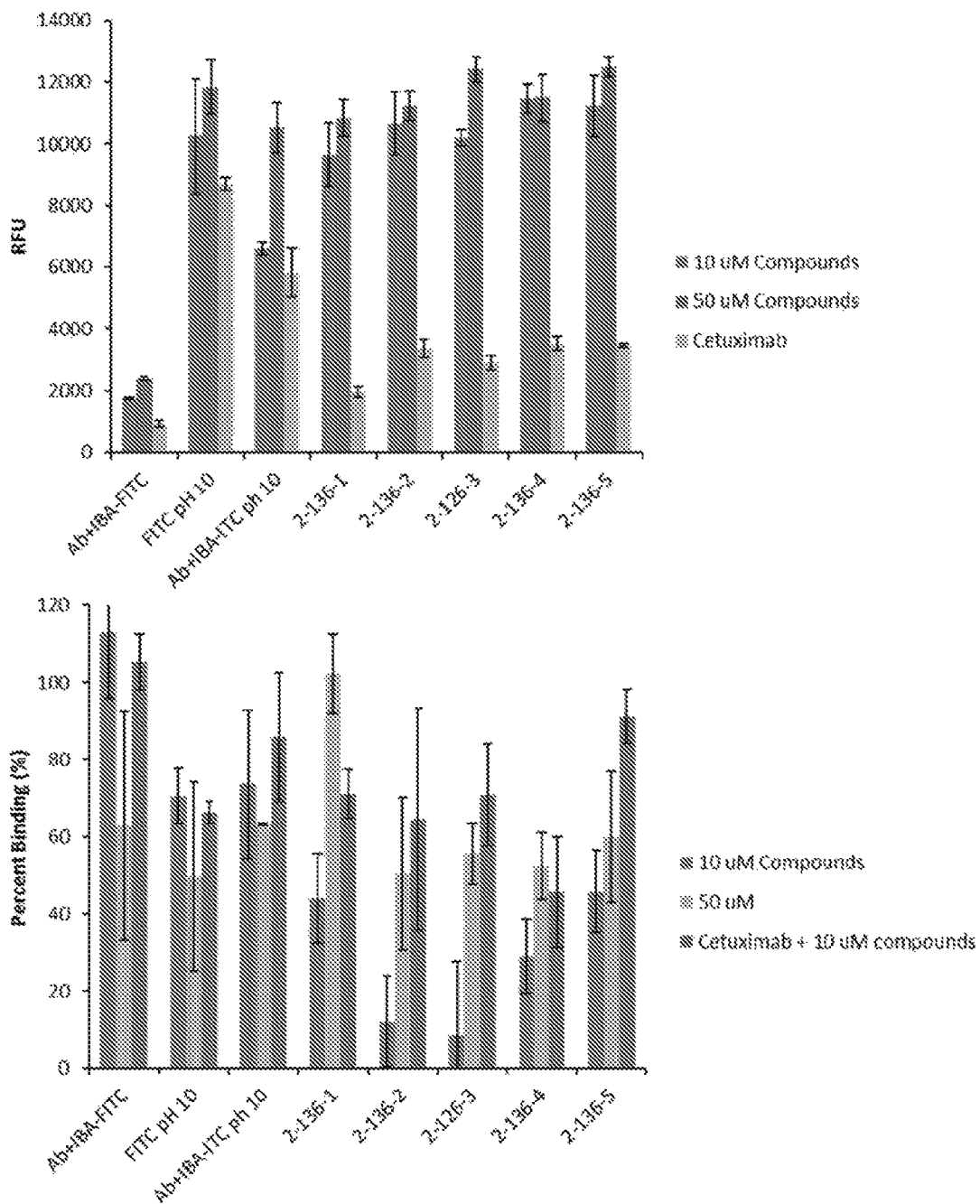
FIG. 8. Rituximab cHBI's demonstrate specific attachment to Rituximab at varying concentrations using ELISA (top graph). Competitive inhibition of Napht binding was demonstrated after incubation with cHBI's using ELISA (bottom graph).
Figure 9:
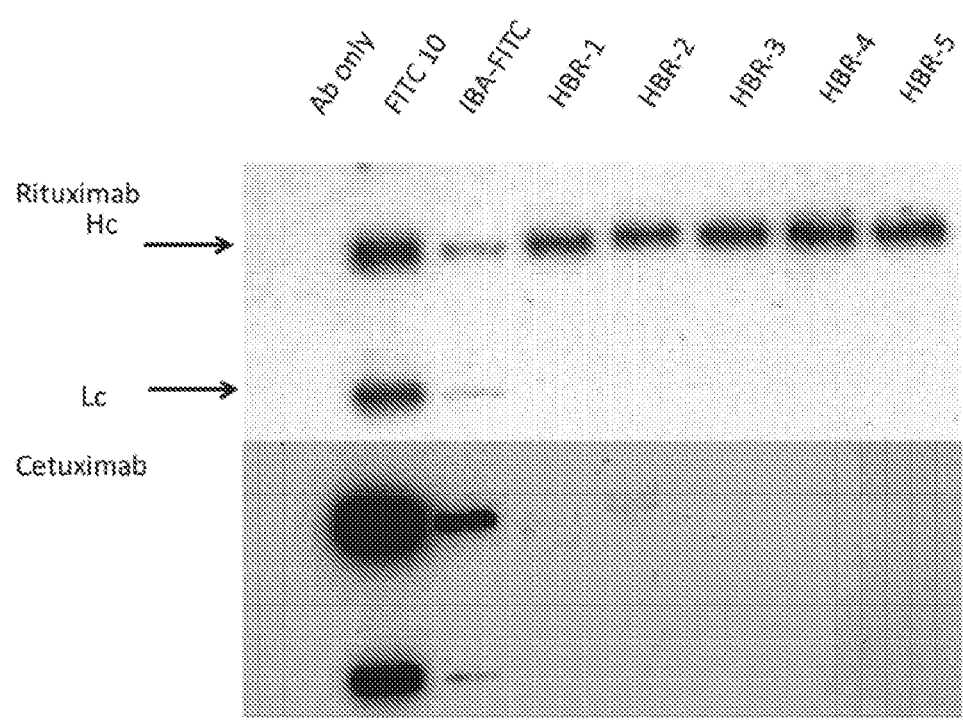
FIG. 9. Western blot demonstrates selective attachment of Rituximab cHBI's to heavy chain of Rituximab. Cetuximab was used as a control.
Figure 11A:
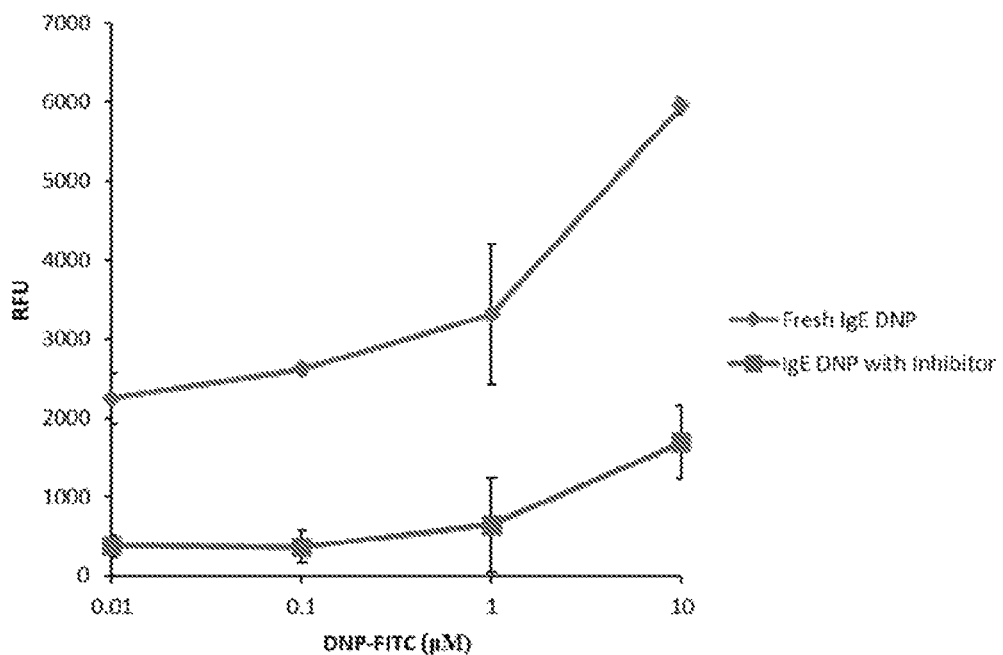
FIG. 11A-11B. Competitive ELISA showing DNP binding inhibition using SPE-7 antibodies incubated for 24 hrs prior with 5 µM DNP cHBI's. (A) Napht binding inhibition demonstrated with ELISA with same preincubated SPE-7 antibodies. (B)
Figure 11B:
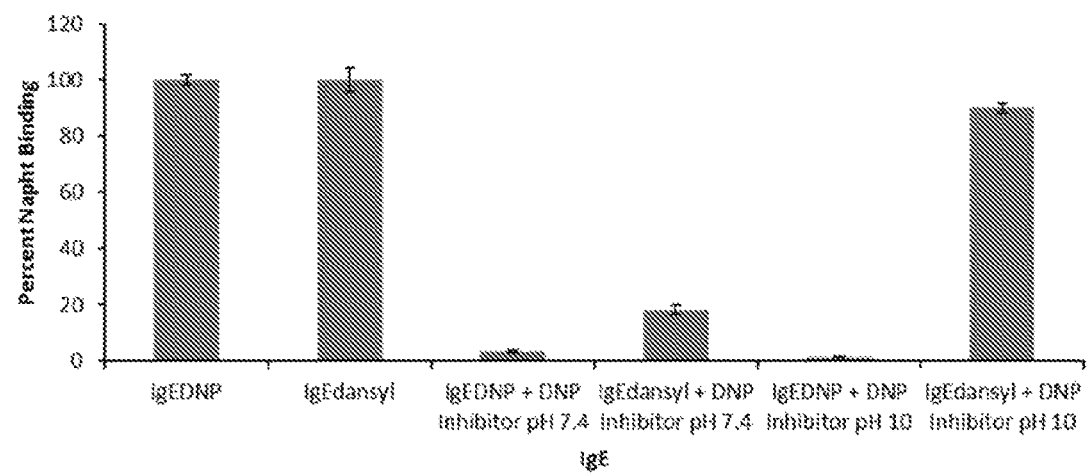
Figure 12:
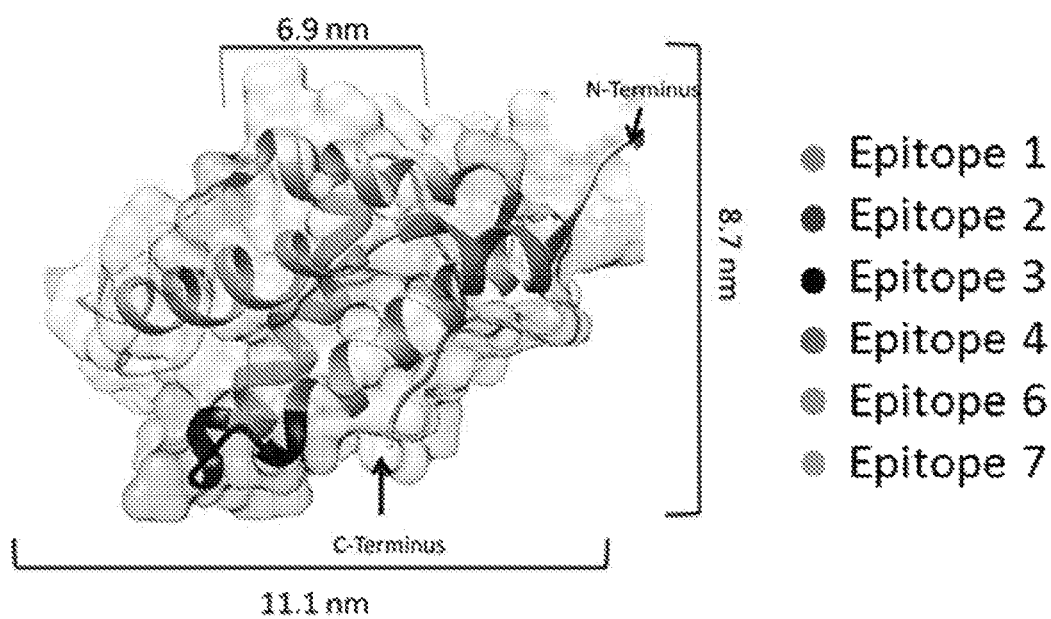
FIG. 12. Protein structure of major peanut protein Ara h 2 with labeled IgE binding epitopes.

The cHBL design consists of four components which function together to provide site specific modification of antibodies: (1) an antigen binding site (ABS) targeting moiety, (2) a NBS targeting ligand to provide bivalent binding of these molecules and (3) a covalent functionality to react with amino acid side chains located proximal to the NBS. These components are linked by a fourth component, an ethylene glycol spacer (EG) to provide appropriate distances between the moieties. The ABS targeting moiety functions to provide specificity for an antibody of interest. These targeting moieties can be targeting peptides, haptens (small molecules with strong affinities for an antibody of interest) or any other antigen mimetic. We used both a hapten molecule and a targeting peptide to provide specificity for two different monoclonal antibodies: a trastuzumab targeting peptide to target trastuzumab (anti-HER2/neu IgG) and the hapten, dinitrophenol (DNP), to target an anti-DNP IgE (SPE-7). We selected a NBS targeting ligand to bind the well conserved NBS shown in FIG. 1A to facilitate bivalent binding to the same antibody. Through in silico screening and experimental confirmation with a fluorescence quenching assay, we identified 2-naphthaleneacetic acid (napht) that has a 2 μM monovalent affinity for the NBS (FIGS. 1B, 1C). These two moieties will combine for bivalent binding on the same antibody, allowing increased specificity of antibody tagging.

These four components are chemically linked together using Fmoc protocols for Solid Phase Peptide Synthesis (SPPS), cleaved from the resin and purified using reverse phase high performance liquid chromatography (RP-HPLC). Nevertheless, many other synthetic methods that can be used to achieve the desired products exist, including but not limited to in solution synthetic methods as well as other solid phase synthetic methodologies such as Boc chemistry. The ABS ligand is typically linear peptide sequences (but could be cyclic peptides and/or mimotopes of the epitope sequences or small molecules such as DNP or penicillin) taken from either current literature or from the peptide sequence of a given allergen protein and then synthesized using SPPS methods. This ABS binder is synthesized first, followed by the linker (in this case an ethylene glycol linker with a variable size depending on the ABS ligand). Next, a molecule that provides heterogeneous chemical modification is added (in our case a Fmoc-Lys (ivDdE)-OH molecule). Then off of this lysine, a NBS ligand (either IBA or Napht) is added off the primary amine and then an additional two ethylene glycol units are added off the epsilon amine. Finally, from the amine terminus of the ethylene glycol spacer, an isothiocyanate moiety is formed using a chemistry adapted from Munch et al. (*Tetrahedron Lett.* 2008; 49(19): 3117-3119). Two example molecules for a DNP inhibitor (FIG. 10) and an Ara h 2 inhibitor (FIG. 13) are provided. These cHBIs can be further optimized by varying the number, type and size of linker molecules between the NBS ligand and the reactive group (FIG. 3).

Materials

NovaPEG Rink Amide resin, 5(6)-carboxy-fluorescein, HBTU (2-(1H-Benzotriazole-1-yl)-1,1,3,3-tetramethyluroniumhexafluorophosphate), carbon disulfide, Fmoc-Lys (IvDde)-OH, Fmoc-His(Trt)-OH, Fmoc-Ser(tBu)-OH, Fmoc-Leu-OH, Fmoc-Glu(OtBu)-OH, Fmoc-Trp(Boc)-OH, Fmoc-Tyr(tBu)-OH, Fmoc-Pro-OH, Fmoc-Gly-OH, Fmoc-Arg(pfb)-OH, 10 kDa 0.5 mL centrifugal filters, and BSA were purchased from EMD Millipore. DMF (N,N-Dimethylformamide) (>99.8%), DCM (dichloromethane) chloromethane) (>99.8%), DIEA (N,N-Diisopropylethylamine), hydrazine, piperidine, TFA (trifluoroacetic acid), TIS (triisopropylsilane), 2-Naphthaleneacetic Acid, $BOC_2O$ (Di-tert-butyl carbonate), DMAP (4-(Dimethylamino)pyridine), DNFB (2,4-Dinitro-1-fluorobenzene), acetonitrile, acetic acid, methanol, carbonate-bicarbonate buffer, Tween 20, IBA (Indole-3-butyric acid), PBS (phosphate buffered saline), Tryptamine, 2-Naphthaleneacetic Acid, ethylene diamine, biotin, $BOC_2O$ (Di-tert-butyl carbonate), Succinic anhydride, $CS_2$ (Carbon disulfide), BDI (butane diisthiolcyanate), THF (Tetrahydrafuran), TPP (triphenylphosphine), DIAD (diisopropylazocarboxylate), MeI (methyl iodine), Bicarbonate-carbonate buffer (Bicarb), OVA (ovalbumin), Step-HRP (streptavidin conjugated to HRP), and PCMB (p-chloromercuribenzoic acid) were purchased from Sigma Aldrich. $EG_4$ (Fmoc-N-amido-$dPEG_4$-acid) and $EG_6$ (Fmoc-N-amido-$dPEG_6$-acid) were purchased from Quanta biodesign. FITC (Fluorescein Isothiocyanate) was purchased from Toronto Research Chemistry. Tris-Glycine buffer was purchased from VWR. Non-Fat Powdered Milk, transfer buffer (10×), and SDS-Sample Buffer (4×, reducing) were purchased from Boston BioProducts. Tris buffered Saline with 0.05% Tween 20 was purchased from KPL. Chemiluminescence substrate was purchased from Thermo scientific. Alexa Fluor 647-conjugated goal anti-human IgG was purchased from Jackson ImmunoResearch Laboratories, Inc. Anti-dansyl TgE (clone 27-74) and anti-human cyclinA TgE (clone BF683) were purchased from BD Biosciences. Anti-DNP IgE (clone SPE-7) was purchased from Sigma Aldrich. Trastuzumab was a generous gift from Dr. Alex Starodub at Goshen Cancer Center (Goshen, Ind.).

High Binding and Non-Binding 96-well plates were purchased from Corning. Minimum Essential Media, Penicillin-Strep solution, L-glutamine, and Amplex Red ELISA kits were purchased from Life Technologies. Bovine Serum Albumin was purchased from Gemini Biosciences. 96-well Tissue Culture plates were purchased from Falcon.

$EG_2$ (Fmoc-N-amido-$dPEG_2$-acid) and $EG_8$ (Fmoc-N-amido-$dPEG_8$-acid) were purchased from Quanta biodesign.

FITC (Fluorescein Isothiocyanate) was purchased from Toronto Research Chemistry.

Tris-Glycine buffer was purchased from VWR.

Non-Fat Powdered Milk, transfer buffer (10×), and SDS-Sample Buffer (4×, reducing) were purchased from Boston BioProducts.

Tris buffered Saline with 0.05% Tween 20 was purchased from KPL.

Chemiluminescence substrate was purchased from Thermo scientific.

Anti-dansyl IgE (clone 27-74) and anti-human cyclinA IgE (clone BF683) were purchased from BD Biosciences.

Mouse $IgG^{Penicillin}$ (monoclonal antibody clone P2B9) was purchased from Abcam Anti-DNP IgE (clone SPE-7) was purchased from Sigma Aldrich.

Example 1 cHBI Synthesis

All hapten conjugated molecules (cHBI, HBI or Hapten-ITC's) were synthesized using Fmoc solid phase peptide synthesis (SPPS) with several modifications. The basic peptide synthesis procedure is described briefly: molecules were conjugated to Rink Amide Low Loading Resin (Millipore), Fmoc-amino acids and Fmoc protected ethylene glycol spacers and Napht were dissolved at 4-fold excess in DMF, activated with a 3.6-fold excess of HBTU with 20-fold DIEA for five minutes prior to addition. DNP was added as DNFB and dansyl was added as dansyl chloride at 4-fold excesses in DMF with 20-fold DIEA. Activated Fmoc protected amino acids, haptens and Napht were reacted with amines on resin for 30 minutes for each step. After addition, resin was washed three times with DMF, and deprotected with 20% piperidine in DMF for 3 minutes three times. Following deprotection, resin was washed with DMF and DCM. Following Napht addition, the IvDdE group of lysine was deprotected using 2% hydrazine in DMF in the same fashion.

ITC domains were always added just prior to cleavage from resin. For dansyl and DNP cHBI molecules primary amines were chemically modified into ITC moieties using a modified procedure from Munch et al. (*Tetrahedron Lett.* 2008; 49(19): 3117-3119). Briefly, resins with deprotected primary amines were washed in anhydrous DMF three times. A tenfold excess $CS_2$ with a 20-fold excess of DIEA was added in DMF and allowed to react for 30 minutes. Resin was then drained and washed once with anhydrous DMF. One mL of DMF with a 20-fold excess of DIEA was added to resin and cooled to approximately 0° C. in –20° C. freezer. Then, a 2-fold excess of $Boc_2O$ and 0.2-fold of DMAP was added to vessel and allowed to react for 20 minutes at –20° C. Vessel was removed, allowed to warm to room temperature for thirty minutes and then washed with DMF, DCM and diethyl ether and allowed to dry in vacuum chamber.

Penicillin cHBI molecules had two different chemistries to maintain proper ITC functionality. Prior to penicillin addition, penicillin in solution was reacted with ethylene diamine to open beta lactam ring and purified, forming a penicilloyl-$NH_2$. Then resins with deprotected amines were reacted with succinic anhydride to leave a terminal carboxylic acid group. This group was then activated with an equimolar amount of HBTU in 5-fold excess of DIEA in DMF for 10 minutes. Resin was washed with DMF and then a 4-fold excess of penicilloyl-$NH_2$ was added with 20-fold excess of DIEA in DMF and allowed to react for 30 minutes. The penicilloyl conjugate contains a secondary amine which is reactive to ITC. So, to prevent HBI cyclization, this secondary amine was methylated into a tertiary amine following a procedure by Kurosu et al. (*Tetrahedron Lett.* 2006; 47(28): 4871-4875). Following reaction, the resin was washed several times with DMF and synthesis continued following IvDdE deprotection. Additionally, to improve overall cHBI yields, ITC was conjugated by addition of bifunctional ITC molecules, BDI. BDI was added to free amines in a 10-fold excess in DMF with DIEA and allowed to react for two hours. This was the final step prior to cHBI cleavage.

Molecules were cleaved from the resin using a 95/2.5/2.5 TFA/water/TIS mixture for two cycles for 45 minutes each.

The resulting solution was rotovapped to remove TFA, rehydrated in 50/50 ACN/water and purified by RP-HPLC using an Agilent 1200 series HPLC with a Zorbax C18 semi prep column using a ACN/water gradient between 20-60% ACN in 10 minutes with a flow rate of 4 mL/min. Product was collected, rotovapped, lyophilized and re-dissolved in DMSO. Concentration was determined by absorbance at 280 nm or 335 nm. All molecules were characterized using high resolution MicroTOF MS analysis. Purity was determined by analytical RP-HPLC using Zorbax Eclipse XBD-C18 with a 20-60% ACN gradient.

Molecules used in ELISA and flow cytometry contained either a biotin or fluorescein (FITC) tag that was incorporated onto resin prior to molecule synthesis. In each case, Fmoc-Lys(IvDdE)-OH was attached first to the resin, deprotected on Fmoc amine, conjugated to Fmoc-EG$_2$-OH, deprotected again and conjugated to either Biotin activated with HBTU or FITC. Then, IvDdE group is deprotected and synthesis is continued for either penicillin or dansyl cHBIs.

Synthesis and Purification of DNP, Rituximab, and Trastuzumab cHBL

Figure 22:
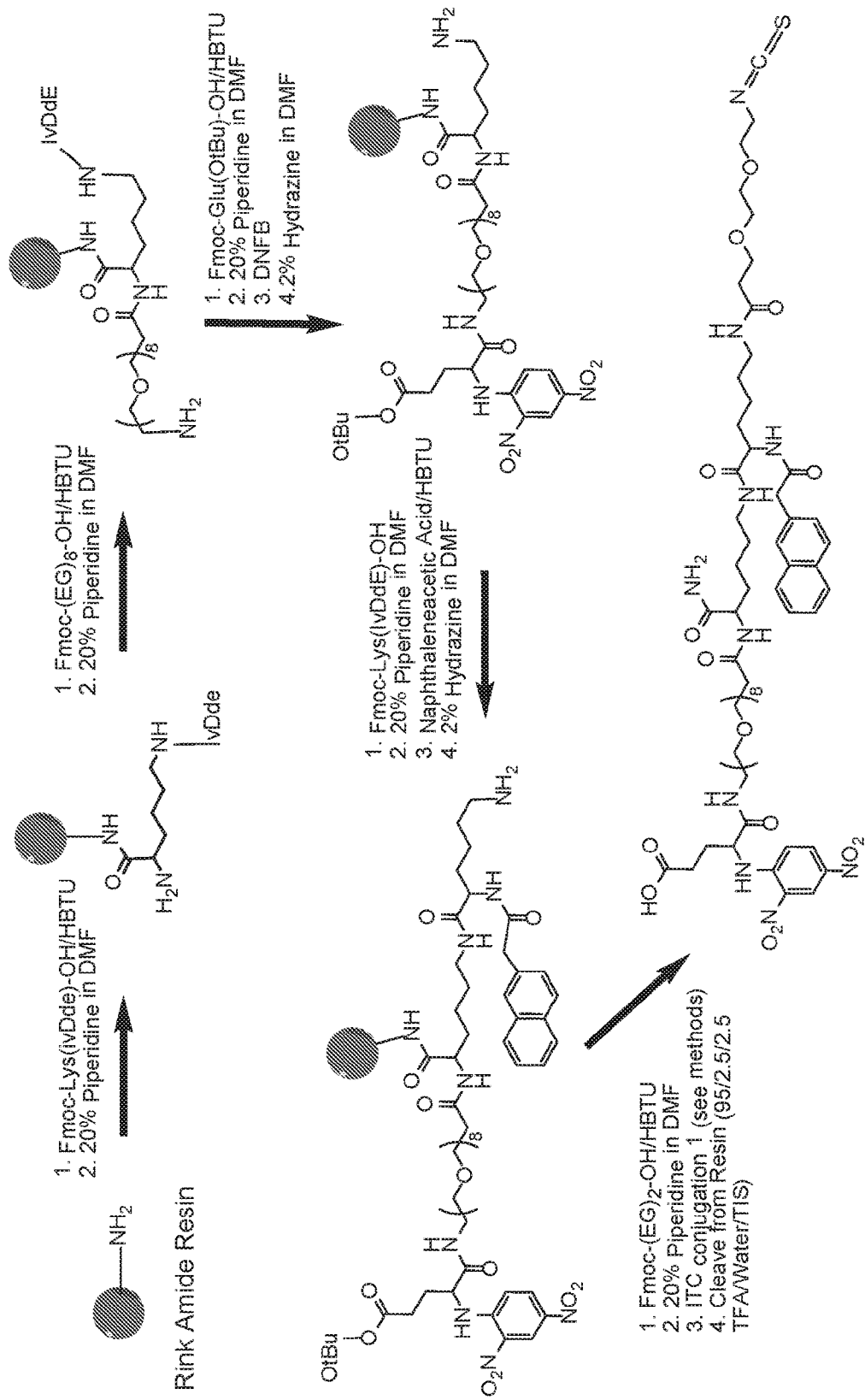
Figure 23:
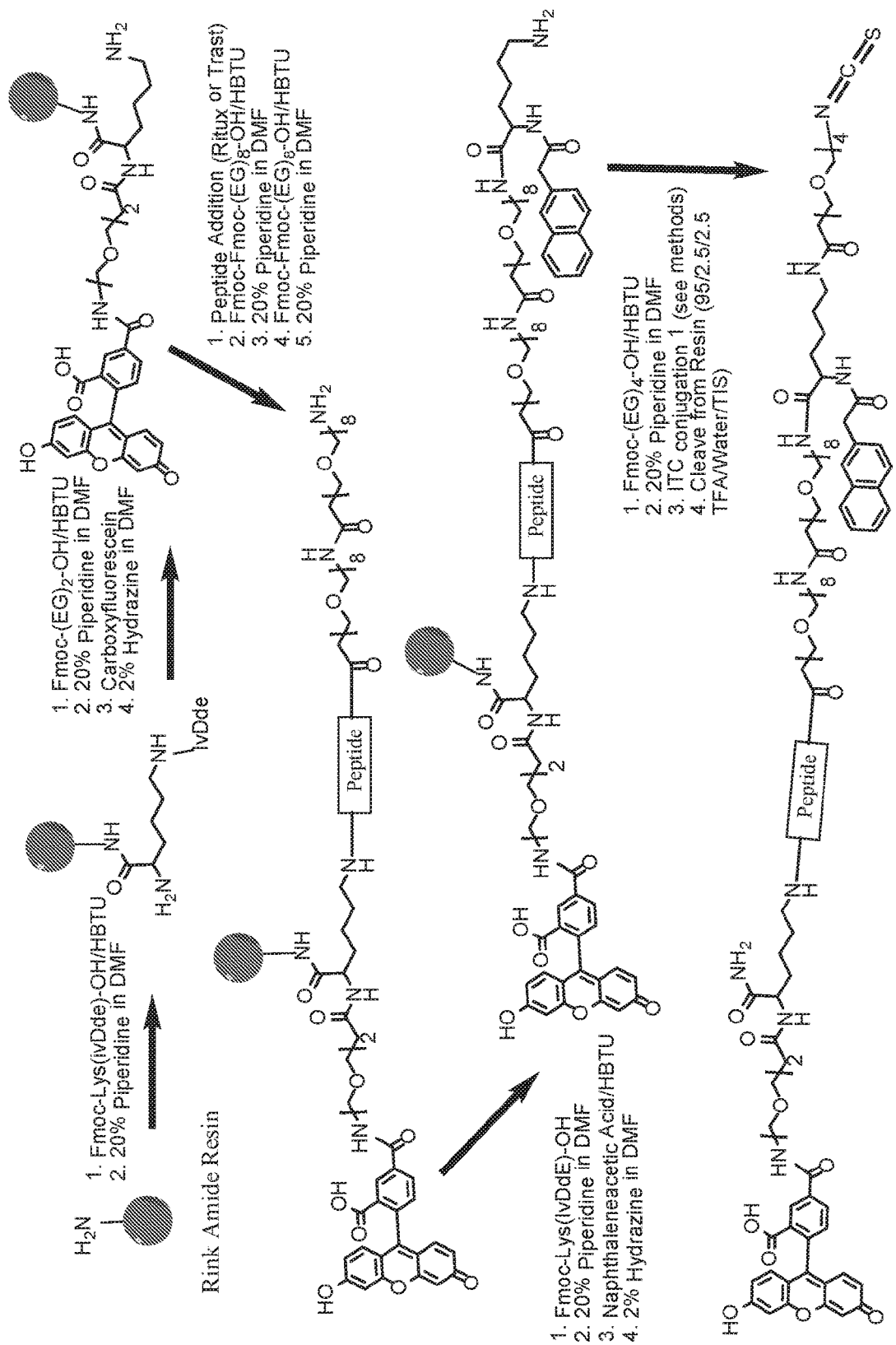
Figures 24A, 24B, 24C:
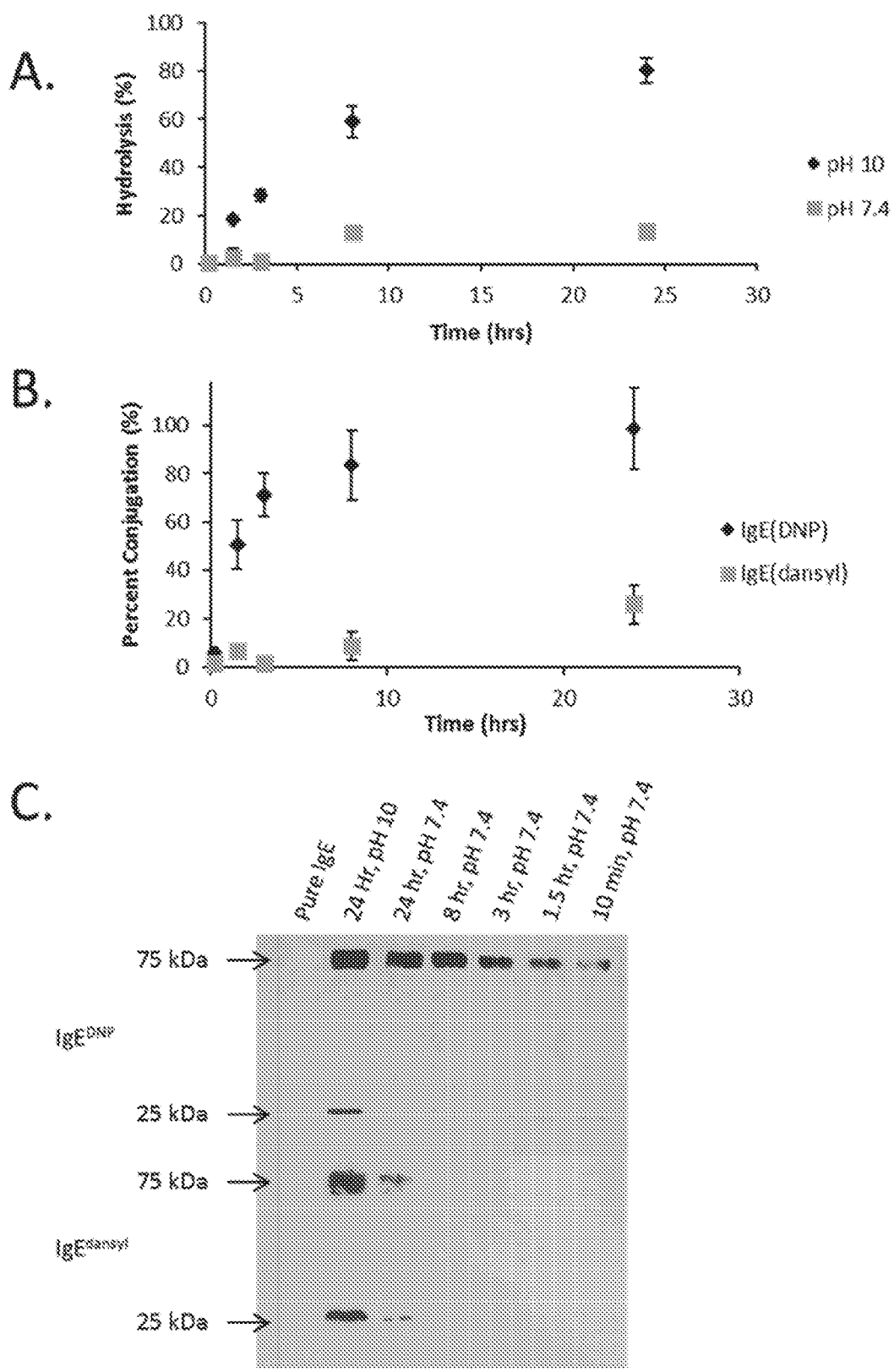

ABS and NBS ligands were synthesized using Fmoc chemistry-based solid support peptide synthesis as previously described (Handlogten M W, et al., Biochem J. 2013; 449: 91-99) The overall synthetic schemes of cHBLs are described in FIG. 22 and FIG. 23. Briefly, terminal acid groups with both Fmoc-protected amine and protected side chain groups were activated by 3.6-fold and 20-fold molar excess of HBTU and DIEA in DMF for 5 min. Activated carboxylic acids were coupled to resin-conjugated terminal amine for 30 min. Fmoc and IvDdE groups were deprotected by 20% piperidine and 2% hydrazine in DMF, respectively. Kaiser test was performed to monitor successful conjugation in every coupling and deprotection step. 5(6)-carboxy-fluorescein molecules following ethylene glycol spacer (EG$_2$) was conjugated to both rituximab and trast-cHBL to perform enzyme-linked immunosorbent assay (ELISA) while 2,4-Dinitro-1-fluorobenzene (DNFB) is conjugated to the EG$_2$ spacer to perform fluorescence quenching assays. Ethylene glycol spacer (EG$_6$×2) was conjugated to the ABS targeting ligand to allow for flexible binding of cHBLs. Both 2-Naphthaleneacetic acid and isothiocyanate (ITC) were branched using Fmoc-Lys (IvDdE)-OH to act as a NBS targeting ligand and functional molecule for covalent conjugation. 2-Naphthaleneacetic acid was directly coupled to a deprotected α-amine and ethylene glycol linker (EG$_4$) was coupled to the deprotected ε-amine for the following ITC conjugation.

ITC was conjugated to terminal amine group of EG$_4$ via base catalyzed synthesis as previously described by Munch et al. (Tetrahedron Lett. 2008; 49(19): 3117-3119). However, it is distinct from previous method in that isothiocynate conjugation occurred on solid support resin. Briefly, the Fmoc-protected primary amine of EG$_4$ was deprotected and washed with DMF, DCM, and anhydrous DMF three times in a sequential order. The deprotected amine group reacted with 10-fold and 20-fold molar excess of carbon disulfide (CS$_2$) and DIEA for 30 min at room temperature, respectively. Formation of dithiocarbamate was monitored by Kaiser test and followed by addition of 10-fold molar excess of DIEA in 1 mL to avoid protonation of sulfur anion. The resin was kept in −80° C. Freezer until it reached 0° C. 2-fold molar excess of Di-tert butyl carbonate (Boc$_2$O) was added to the resin followed by addition of 0.2-fold molar excess of 4-(Dimethylamine) pyridine (DMAP) base catalyst to initiate ITC conjugation in −20° C. freezer for 20 min. After 20 min, the reaction further took place in room temperature for 0.5 hour to yield ITC conjugates. The cHBLs were cleaved from the resin using 95/2.5/2.5% of TFA/water/TIS mixture for 2×45 min. Agilent 1200 RP-HPLC was used to purify the cHBLs with a two-phase system, 90/10 of ACN/water and water, and a Zorbax C18 semi-preparative column. The gradient was from 40 to 60% of ACN/water mixture for 10 mins with a flow rate of 4 mL min$^{-1}$. A Zorbax analytic C18 column was used to determine the purity (>95%) using the same gradient with a flow rate of 1 mL min$^{-1}$. The product was confirmed using a Bruker microToF II mass spectrometer, note that all are listed with a +1 charge: DNP-cHBL; 1346.60 Da expected, 1347.70 Da observed. Trast-cHBL; 3476.67 Da expected, 3477.67 Da observed. Trast-ITC; 2948.33 Da expected, 2949.33 Da observed. Rituximab-cHBL; 3020.43 Da expected, 3020.44 Da observed. Trast-DNP; 1893.95 Da expected, 1893.94 Da observed. Trast-Napht-DNP; 2881.45 Da expected, 2882.45 Da observed. Biotin-Napht; 1009.53 Da expected, 1010.54 Da observed. See Table 3 for structures of all molecules synthesized for this study.

Quantification of DNP cHBL by RP-HPLC

DNP cHBL (concentration) was incubated with either PBS (pH 7.4) or carbonate-bicarbonate buffer (pH 10) for various time points (10 min-24 hours) at room temperature. The cHBL was then mixed with 50/50/0.1% of ACN/water/TFA mixture to stop hydrolysis. Agilent 1200 RP-HPLC was used to quantify hydrolytic product and reactive ITC with a Zorbax C8 poroshell column as previously described (Deak P E, et al., Experimental Biology and Medicine. 2016). A two phase system of water and 90/10% of ACN/water was used with a flow rate of 2 mL min$^{-1}$ at 60° C. for 5 min. The absorbance was read at 220, 280, and 360 nm for quantification. Hydrolytic product and reactive ITC were eluted at around 2.8 and 3.3 min, respectively.

Quantification of Antibody-Conjugated DNP cHBL

DNP cHBL was incubated with either anti-DNP IgE or anti-dansyl IgE in PBS for various time points at room temperature. FITC in carbonate-bicarbonate buffer and anti-DNP IgE alone in PBS were used as a positive and negative control, respectively. After incubation, the IgE bound cHBL was purified using Amicon Ultra-0.5 mL Centrifugal Filters (Millipore) to remove the unbound cHBL. The molecule was mixed with 50/50% of ACN/water mixture and quantified using analytical RP-HPLC as described above.

Fluorescence Quenching Assay

The binding constants ($K_d$) of monovalent ABS (trastuzumab binding peptide), NBS (naphthalene), and heterobivalent ligand (trast-napht) were determined using fluorescence quenching assay as previously described (Handlogten M W, et al., Chem Biol. 2011; 18(9): 1179-1188). Briefly, ligands were titrated into trastuzumab (30 nM) as well as PBS and Indole-3-butyric acid (IBA) to exclude the effect of nonspecific interactions between DNP and tryptophan. Since DNP absorbs light at 335 nm and tryptophan emits light at 335 nm, the fluorescence of tryptophan is quenched by DNP. The fluorescence of tryptophan was read by SpectraMax M5 plate reader (Molecular Devices) at $\lambda_{ex}$=280 nm and $\lambda_{em}$=335 nm with various concentrations of ligands. The fluorescence signals dropped upon titration of ligands and apparent binding constants were calculated using a Hill's curve fit in OriginPro 2015.

Fluorescence Quenching.

To determine binding of HBI molecules to respective antibodies, we observed the quenching of tryptophan resides using a method previously described (Junutula J R, et al., Nat. Biotechnol. 2008; 26(8): 925-932). Briefly, either IgE$^{dansyl}$ or IgG$^{Penicillin}$ was diluted into a non-binding 96-well dish at 40 nM in PBS. Then, HBI molecules which contained either a dansyl or DNP group were titrated into well and fluorescence (Ex. 280 nm, Em. 335) was observed using a SpectraMax M2 spectrophotometer. PBS and free tryptamine diluted to similar initial fluorescence values were used as controls to account for HBI fluorescence and non-specific quenching respectively.

Enzyme-Linked Immunosorbent Assay (ELISA) for Selective Binding of cHBL

ELISA was used to confirm selective binding of trast-cHBL to trastuzumab. Trast-cHBL, trast-ITC conjugate, and rituximab cHBL with various concentration (0.1-10 µM) reacted with trastuzumab (200 nM in 500 µL of PBS, pH 7.4) for 8 hours at 37° C. incubator. FITC also reacted with trastuzumab at the same conditions except for pH; they were incubated in either PBS or carbonate-bicarbonate buffer. Trastuzumab without any covalent ligands was used as a negative control (pH 7.4). After an 8-hour reaction, all molecules were purified using Amicon Ultra-0.5 mL Centrifugal Filters to remove the unbound covalent ligands. Concentration of trastuzumab was determined by SpectraMax M5 plate reader. For ELISA, 96 well high-binding assay plate was coated with trastuzumab (0.5 nM in carbonate-bicarbonate buffer) overnight at 4° C. refrigerator. The next morning, the wells were washed with a washing buffer (0.05% Tween 20 in PBS) using AquaMax 2000 plate automatic washer (Molecular Devices) to remove unbound trastuzumab and blocked with blocking buffer (5% (w/v) BSA and 0.1% (v/v) Tween 20 in PBS) for 1 hour at room temperature. After 1 hour, the wells were washed and then incubated with goat anti-FITC IgG-HRP conjugate (1:20,000 in blocking buffer) for 1 hour. Amplex Red Hydrogen Peroxide/Peroxidase Assay kit was used to initiate enzymatic reaction and the fluorescence ($\lambda_{ex}$=570 nm and $\lambda_{em}$=592 nm) was read by SpectraMax M5 plate reader.

Competitive Enzyme-Linked Immunosorbent Assay for Specific Binding of cHBL

The specificity of naphthalene to NBS of IgG was confirmed using UV photo-cross-linking method and competitive sandwich ELISA. The wells of high binding plate were coated with goat-derived anti-human IgGs (1 nM in carbonate-bicarbonate buffer) overnight at 4° C. Trastuzumab (100 nM in PBS) prepared for ELISA described above was incubated with naphthalene-EG$_{11}$-biotin (25 µM in PBS) for 1 hour at room temperature. PBS with only naphthalene-EG$_{11}$-biotin was used as a negative control to normalize the binding curve. After 1 hour incubation, the molecules were exposed to UV light (1 J/cm$^2$) in a Spectroline UV select Series Cross-linker (Spectronics) to induce covalent photo-cross-linking of naphthalene to unbound NBS. The molecules were spun and 2 nM of the molecules were prepared in the blocking buffer. The wells coated with goat anti-human IgGs were washed and blocked with the blocking buffer for 1 hour. The wells were washed followed by incubation with the UV photo-cross-linked trastuzumab (2 nM) for 1 hour. The wells were washed and incubated with streptavidin-horseradish peroxidase conjugate (1:10,000 in blocking buffer) for 1 hour. An Amplex red assay kit was used to detect the fluorescence signals from the specific binding of naphthalene to NBS induced by UV photo-cross-linking. Since cHBL contains naphthalene, blocked NBS of trastuzumab is expected not to be photo-cross-linked to naphthalene-EG$_{11}$-biotin, leading to relatively lower signals of fluorescence in the presence of cHBL.

Western Blot Analysis of ITC Covalent Conjugation to Specific Lysine of Antibodies ITC conjugation to active lysine on either light chain (IgG) or heavy chain (IgE) proximal to NBS was confirmed by western blot as previously described (Alves N. J., et al., Langmuir. 2012; 28(25): 9640-9648). The samples (20 nM in 1×SDS reducing buffer) were run on a 10% SDS-PAGE gel at 110 V for 50 min in the presence of a Tris-glycine running buffer. The samples were then transferred to a nitrocellulose membrane (Bio-Rad) at 90 V for 90 min in a 20% methanol transfer buffer. The membrane was blocked with a blocking buffer (5% (w/v) non-fat dry milk in Tris buffered Saline with 0.05% Tween 20 (TBS-T)) for 1 hour. After 1 hour, the membrane was washed once with TBS-T and followed by incubation with HRP-conjugated goat anti-FITC IgG (1:20,000 in blocking buffer) for 45 min. The membrane was washed with 3×TBS-T for 10 min to remove the unbound secondary detection antibodies and subsequently incubated with chemiluminescent HRP substrate for 5 min to detect the location at which lysine on either heavy or light chain is conjugated to cHBL molecules. A second SDS-PAGE gel was run concurrently and stained in Commassie blue staining solution (0.15% Coomassie R-250 (EMD chemicals), 10% acetic acid and 20% methanol in DI water) and destained in destaining solution (10% acetic acid, methanol, and 80% DI water) to confirm that all the proteins were transferred to the membrane. Trastuzumab without any covalent ligands and trastuzumab-FITC (20 µM in carbonate-bicarbonate buffer and 1 µM in PBS) were used as a negative and positive control, respectively.

LC-MS/MS Sample Preparation and Analysis

IgE$^{DNP}$ with and without cHBL conjugation were run on 10% SDS-PAGE gels for 60 minutes under non-reducing conditions after being incubated for 3 hours with papian (20 ng papian/mg antibody). The gel was stained with coomassie stain and then washed with a washing buffer. Bands in the gel were compared to a standard protein ladder (Bio-Rad), cut out and washed several times with 50 nM ammonium bicarbonate buffer or acetonitrile to remove remaining protein stain. A portion of these gels were crushed and soaked in a formic acid/isopropyl alcohol/water mixture and the masses of the proteins observed with MALDI mass spectroscopy as previously described in order to ensure the isolation of a Fab fragment. The remaining gel was reduced with DTT and alkylated with iodoacetamide and then digested overnight with trypsin (20 ng trypsin/mg antibody) at 4° C. After digestion, trypsin peptide fragments were dried and desalted using micro C18 Ziptips, according to manufacturer's instructions. The fragments of both cHBL conjugated and unconjugated control were analyzed by Nano UHPLC/MS/MS on a 100 mm 100 mm C18 BEH column (Waters) running at 700 nL/min over a 60-min gradient from 5 to 35% acetonitrile (0.1% FA), then acquisition was performed using a LTQ-Velos Orbitrap mass spectrometer running a TOP8 data dependent mode acquisition as described previously (Llarrull L I, et al., J Biol Chem. 2011; 286(44): 38148-38158). Peak lists were analyzed against common typsin fragments, determined using an online calculator (web.expasy.org/peptide_cutter) with and without molecule addition.

Cell Culture

RBL-2H3 cells were cultured as previously described, split every 48-72 hours at a 1:3 dilution into fresh RBL-2H3 media. Plates for experiments were prepared at roughly 500,000 cells per mL in either 0.5 mL or 100 µL wells on tissue culture plates.

Cellular Binding Assay

Inhibition of trastuzumab by binding of trast-cHBL was confirmed by cellular binding assay with HER2-overexpressed breast and ovarian cancer cell lines (BT474 and SKOV3) using a Guava EasyCyte 8HT flow cytometer (Millipore). 0.5 mL of 50000 cells/mL were cultured on 2-well tissue culture plates overnight. The plate was kept on ice for 30 min to avoid receptor internalization. The wells were washed with a blocking buffer (1.5% BSA in PBS) and incubated with trastuzumab that had been previously incubated with trast-cHBL at various concentrations in the same fashion as the ELISA experiments for 1 hour on ice. The wells were washed once and incubated with Alexa Fluor 647-conjugated goat anti-human IgG (1:500 in blocking buffer) for 1 hour on ice. The wells were washed once with blocking buffer and the cells were gently scraped to run flow cytometer. Green (FITC) and Red2 (Alexa fluorophore with $\lambda_{em}$=667 nm) fluorescence were read to confirm trast-cHBL binding. Trastuzumab without any ligands and trastuzumab-FITC conjugate were used as positive controls and the cells with Alexa Flour 647-conjugated secondary antibody and without trastuzumab were used as negative controls.

Degranulation Inhibition Assay

RBL degranulation inhibition assay was performed as previously described except for the addition of DNP-specific cHBL inhibitor. RBL-2H3 cells (0.5×10$^6$ cells/mL) were cultured on 96-well tissue culture plate for overnight. The cells were primed with 25/75% of anti-DNP TgE/anti-cyclinA IgE (1 μg/mL in total antibody concentration). The wells were washed once with dPBS followed by incubation with DNP cHBL inhibitor (1 μM) for 5 hour. DNP-BSA conjugates synthesized as previously described were added into wells with various concentrations (0.01-10,000 ng/mL in Tyrodes buffer) to initiate degranulation. After 90 mM incubation, p-nitrophenyl N-acetyl-β-D-glucosamine solution (1 mM in pH 4.5 citrate buffer) was added to allow for enzymatic cleavage reaction by β-hexosaminidase in cell supernatant solution for 45 min. The reaction was stopped by glycine buffer (1 mM in pH 10.7 solution) and absorbance of product at 405 nm was read to analyze the data. Triton-X (1% (v/v) in DI water) was used as a positive control to normalize the percent degranulation curve.

Degranulation Assay for cHBIs

The degranulation assays followed this basic procedure: (1) RBL cells previously primed with IgEs (either from monoclonal sources or mouse sera from mouse sensitization below) were incubated with cHBIs for varying amounts of time, (2) cells were washed to remove any unbound or unconjugated cHBIs, (3) allergen was added to stimulate degranulation. Briefly, 50,000 cells were incubated in a 96-well tissue culture plate and either mixtures of monoclonal antibodies (with 25% IgE$^{dansyl}$ and 75% orthogonal IgE$^{cyclinA}$) to a concentration of 1 μg/mL or dilutions of mouse sera were added for 24 hours. Cells were then washed with sterile PBS and cHBI compounds were added at various dilutions for varying time points. Cells were then washed with tyrodes buffer and degranulation was triggered using either dansyl-BSA or penicillin-BSA as previously described (Junutula J R, et al., Nat Biotechnol. 2008; 26(8): 925-932). Percent inhibition was calculated by dividing percent degranulation with cHBI's by control without cHBI for same allergen concentration. For experiments in FIG. 32C, after incubating with inhibitors for 24 hours, cells were washed and allowed to incubate in cell culture media between 24-72 hours before testing degranulation response.

In Solution Conjugation of cHBI Molecules

Before ELISA analysis of cHBI-antibody conjugates, we performed an in-solution conjugation of cHBI molecules and antibodies allowing ITC moieties to react with primary amines on antibody proteins. Either dansyl or penicillin cHBI molecules at various concentrations were incubated with either IgE$^{dansyl}$ or IgE$^{DNP}$ (as control) or IgG$^{Penicillin}$ or BSA (as control) at 1 μM concentrations for various incubation times in either PBS (pH 7.4) or Bicarbonate-Carbonate Buffer (pH 9.6) at 50 μL total volumes at 37° C. After reaction, excess cHBI molecules were removed using membrane filtration with 10 kDa 0.5 mL Centrifugal Filters (Millipore) by washing antibodies three times in PBS. Purified antibodies were analyzed with a SpectraMax M5 spectrophotometer at 280 nm using an extinction coefficient of 200,000 cm$^{-1}$M$^{-1}$ for IgE$^{DNP}$ and IgE$^{dansyl}$ and 150,000 cm$^{-1}$M$^{-1}$ for IgG$^{Penicillin}$.

ELISA

Binding of cHBI molecules to antibodies was observed using a direct ELISA. 100 μL of 2 nM antibody or BSA molecules previously reacted with cHBIs that were labeled with biotin were incubated for 2 hours in bicarbonate buffer on a high binding 96-well plate. Plates were washed with a AquaMax 2000 plate-washer to remove unbound antibody. Wells were blocked with a 5% BSA, 0.2% Tween 20 solution in PBS for 1 hour, washed and incubated with a streptavidin conjugated to HRP for 1 hour in blocking buffer. Plate was washed again and an Amplex Red Kit was used to quantify ELISA signal using a SpectraMax M5 spectrophotometer according to manufacturer's instruction.

Flow Cytometry

Flow cytometry was performed on RBL-2H3 cells using a Guava easyCyte 8HT to demonstrate dansyl cHBI molecule attachment under more physiological conditions. RBL-2H3 cells split at 500,000 cells per mL into a 24-well dish (0.5 mL each) and allowed to attach to plate overnight. Following morning, 0.5 μg of IgE$^{DNP}$ or IgE$^{dansyl}$ was added and allowed to incubate for 24 hours. Cells were then washed twice with sterile PBS, and incubated with fresh media with dansyl cHBI-FITC between 0-1000 nM for 16 hours. Cells were then washed again with PBS and given fresh media, then chilled on ice for 30 minutes. Cells were washed with PBS and incubated in 1.5% BSA in PBS, scrapped and analyzed.

Protein-Hapten Conjugates

Protein-Hapten conjugates were prepared to sensitize mice for allergen challenges and to trigger in vitro degranulation. Two different haptens, penicillin and dansyl chloride were used with two different protein carriers, OVA and BSA. OVA conjugates while BSA conjugates were used to trigger degranulation and perform allergen challenges. Dansyl was conjugated to OVA and BSA by dissolving 20 mg of BSA or OVA in 3 mL bicarbonate-carbonate buffer (pH 9.6) and then adding 20 mg of dansyl chloride that was dissolved in DMF. These compounds reacted under mild stirring over 24 hours at 37° C. After reaction, products were passed through a 0.22 μM filter and filted using 10 kDa membrane filtration to remove excess dansyl. Using a dansyl extinction coefficient of 3400 cm$^{-1}$M$^{-1}$ at 335 nm, and an extinction coefficient of 43800 and 30950 cm$^{-1}$M$^{-1}$ at 280 nm for BSA and OVA respectively and a dansyl correction factor of 0.39 to correct for dansyl absorbance at 280 nm. Using the ratios of absorbance at 335/280 nm, we determined dansyl-BSA to have 18 dansyl per protein and dansyl-OVA to have 12 dansyl per protein.

For penicillin conjugates, performed a similar addition of hapten to protein, except using 200 mg of penicillin G salt and allowing reaction to take place over 72 hours. Penicillin-protein conjugates were filtered in a similar manner as dansyl. To determine conjugation efficiency, we used a Penmaldate assay from Levine et. al. (J Exp Med. 1961;

114(6): 875). We determined penicillin-BSA to have 12 penicillins per protein while penicillin-OVA had 8 penicillins per protein.

Example 2

Pharmaceutical Dosage Forms

The following formulations illustrate representative pharmaceutical dosage forms that may be used for the therapeutic or prophylactic administration of a compound of a formula described herein, a compound specifically disclosed herein, or a pharmaceutically acceptable salt or solvate thereof, or a composition thereof (hereinafter referred to as 'Compound X'):

| (i) Tablet 1 | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/mL) | mg/mL |
|---|---|
| 'Compound X' (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/mL) | mg/mL |
|---|---|
| 'Compound X' (free acid form) | 10.0 |
| Monobasic sodium phosphate | 0.3 |
| Dibasic sodium phosphate | 1.1 |
| Polyethylene glycol 400 | 200.0 |

| (v) Injection 2 (10 mg/mL) | mg/mL |
|---|---|
| 0.1N Sodium hydroxide solution (pH adjustment to 7.0-7.5) | q.s. |
| Water for injection | q.s. ad 1 mL |

| (vi) Aerosol | mg/can |
|---|---|
| 'Compound X' | 20 |
| Oleic acid | 10 |
| Trichloromonofluoromethane | 5,000 |
| Dichlorodifluoromethane | 10,000 |
| Dichlorotetrafluoroethane | 5,000 |

| (vii) Topical Gel 1 | wt. % |
|---|---|
| 'Compound X' | 5% |
| Carbomer 934 | 1.25% |
| Triethanolamine (pH adjustment to 5-7) | q.s. |
| Methyl paraben | 0.2% |
| Purified water | q.s. to 100 g |

| (viii) Topical Gel 2 | wt. % |
|---|---|
| 'Compound X' | 5% |
| Methylcellulose | 2% |
| Methyl paraben | 0.2% |
| Propyl paraben | 0.02% |
| Purified water | q.s. to 100 g |

| (ix) Topical Ointment | wt. % |
|---|---|
| 'Compound X' | 5% |
| Propylene glycol | 1% |
| Anhydrous ointment base | 40% |
| Polysorbate 80 | 2% |
| Methyl paraben | 0.2% |
| Purified water | q.s. to 100 g |

| (x) Topical Cream 1 | wt. % |
|---|---|
| 'Compound X' | 5% |
| White bees wax | 10% |
| Liquid paraffin | 30% |
| Benzyl alcohol | 5% |
| Purified water | q.s. to 100 g |

| (xi) Topical Cream 2 | wt. % |
|---|---|
| 'Compound X' | 5% |
| Stearic acid | 10% |
| Glyceryl monostearate | 3% |
| Polyoxyethylene stearyl ether | 3% |
| Sorbitol | 5% |
| Isopropyl palmitate | 2% |
| Methyl Paraben | 0.2% |
| Purified water | q.s. to 100 g |

These formulations may be prepared by conventional procedures well known in the pharmaceutical art. It will be appreciated that the above pharmaceutical compositions may be varied according to well-known pharmaceutical techniques to accommodate differing amounts and types of active ingredient 'Compound X'. Aerosol formulation (vi) may be used in conjunction with a standard, metered dose aerosol dispenser. Additionally, the specific ingredients and proportions are for illustrative purposes. Ingredients may be exchanged for suitable equivalents and proportions may be varied, according to the desired properties of the dosage form of interest.

SUMMARY

This disclosure describes cHBL molecules and characterizes their ability to form site specific covalent interactions to antibodies, in particular $IgE^{DNP}$ and trastuzumab. Due to the presence of three distinct chemical moieties, an ABS binder, an NBS binder, and an ITC reactive domain, cHBL's form covalent bonds selectively to antibody at a lysine near the NBS site. This allows covalent modification of antibodies without disrupting Fc interactions and minimizing off target conjugation. Additionally, as demonstrated by the data, covalent modification can be optimized for tagging antibodies of interest without disrupting antigen binding or for complete antigen binding inhibition simply by altering cHBL concentration (FIG. 30A). Furthermore, cHBL molecules form site specific bonds even in crude mixtures like cell culture media and function to inhibit potential dangerous cellular processes like degranulation (FIG. 30B).

The major impact of the cHBL design is the versatility of these molecules to selective bind antibodies. Given the evidence presented in this study, we believe that cHBLs could be adapted with any number of ABS targeting moieties, creating a large number of possibilities in disease therapeutics and diagnostics. With the appropriate targeting peptide or other small molecule, cHBLs can target, tag or inhibit any antibody of interest. This could be very useful for forming ADC or modifying particular antibodies to display unique chemical functionalities. This has particular application for autoimmune diseases. For example, systemic Lupus patients produce autoantibodies to N-methyl-d-aspartate receptor and dsDNA can be blocked by a peptide agonist, however, due to affinity issues this therapeutic is not clinically feasible. Using the cHBL design, these peptide agonists could perform as an effective therapeutic due to the avidity enhancements. Finally, because cHBL molecules rely upon standard peptide synthesis techniques and can be synthesized on a single resin, they can be readily scaled up for pharmaceutical use. Overall, this study describes the chemical synthesis, characterization and potential biological impact of a novel molecule for forming site specific covalent interactions with antibodies for antibody labeling and inhibition.

Figure 34:
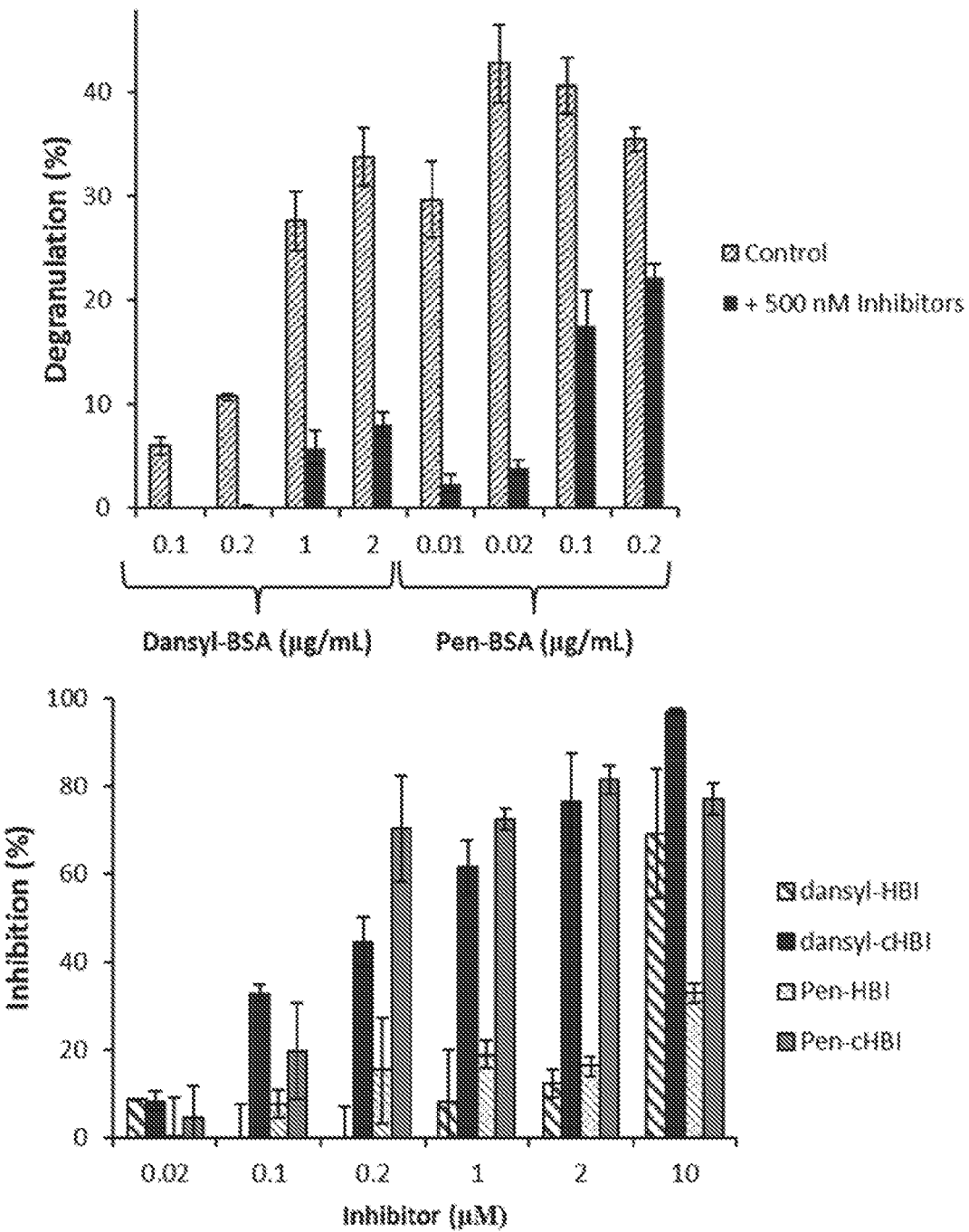
FIG. 34. Degranulation inhibition of RBL cells sensitized with hapten reactive mouse sera ((top), degranulation %; (bottom), inhibition %).
Figure 35A:
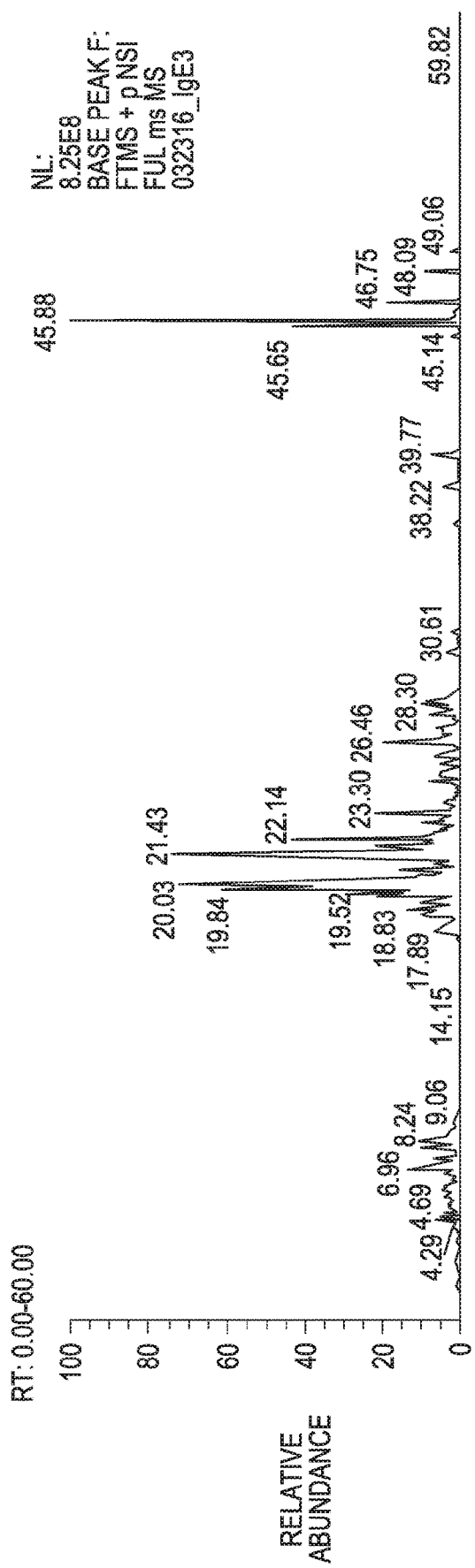
FIG. 35A-35C. MS-MS Result for unconjugated SPE-7 IgE (24-38) Band 1 (Control)—ASGYTFTSYWMHWVK (SEQ ID NO: 3)—MW=1862.85 Da, [M+2H]/2=932.936. Confirmed the presence of peptide ASGYTFT-SYWMHWVK (SEQ ID NO: 3) from unconjugated band 1 after de-staining and trypsinizing with the presence of a doubly charged peak of 932.94 m/z at a retention time of 23.15 mins. Chromatogram given in (A) for all peak, (B) for peptide of interest and MS result give in (C) at specified retention time.
Figure 35B:
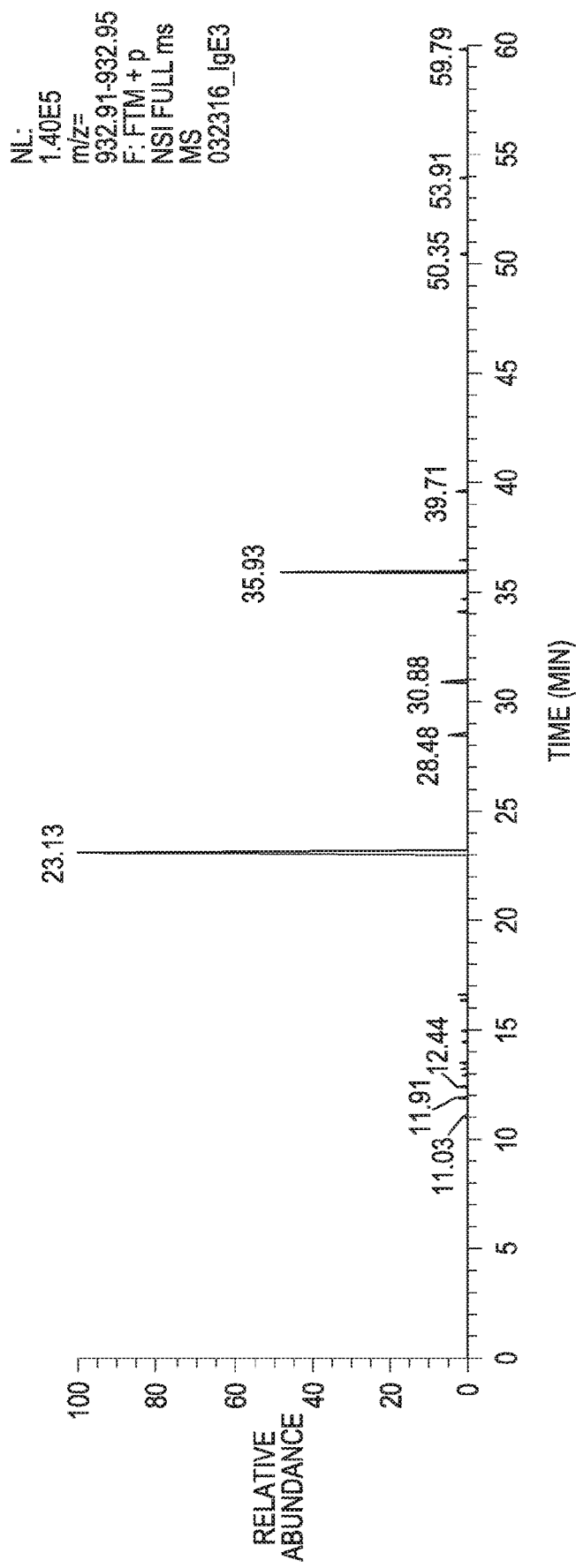
Figure 35C:
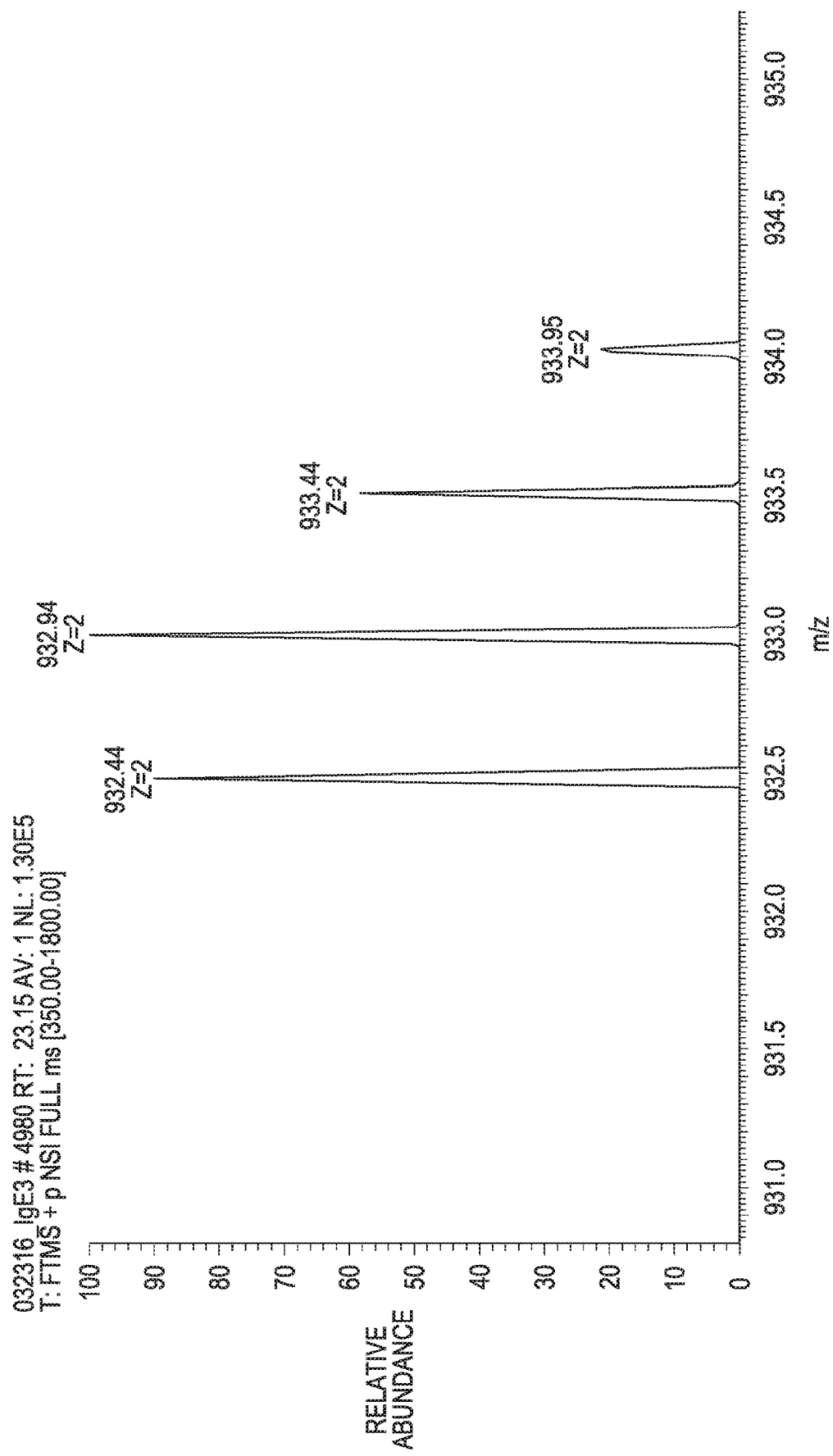
Figure 36A:
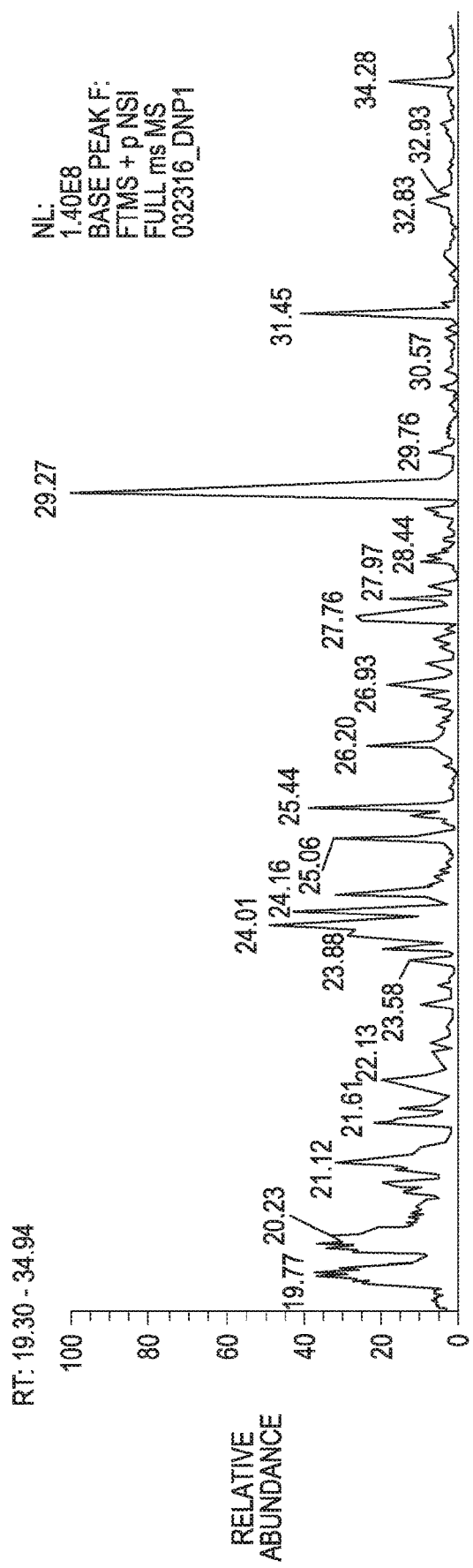
FIG. 36A-36C. MS-MS Result for conjugated SPE-7 IgE (24-38) Band 3 (+cHBL)—ASGYTFTSYWMHWVK (SEQ ID NO: 3)—MW=3135.41 Da, [M+3H]/3=1046.48. Confirmed the presence of peptide ASGYTFT-SYWMHWVK (SEQ ID NO: 3)+DNP from conjugated band 3 after de-staining and trypsinizing with the presence of a triply charged peak of 1046.47 m/z at a retention time of 27 mins. Chromatogram given in (A) for all peak, (B) for peptide of interest and MS result give in (C) at specified retention time.
Figure 36B:
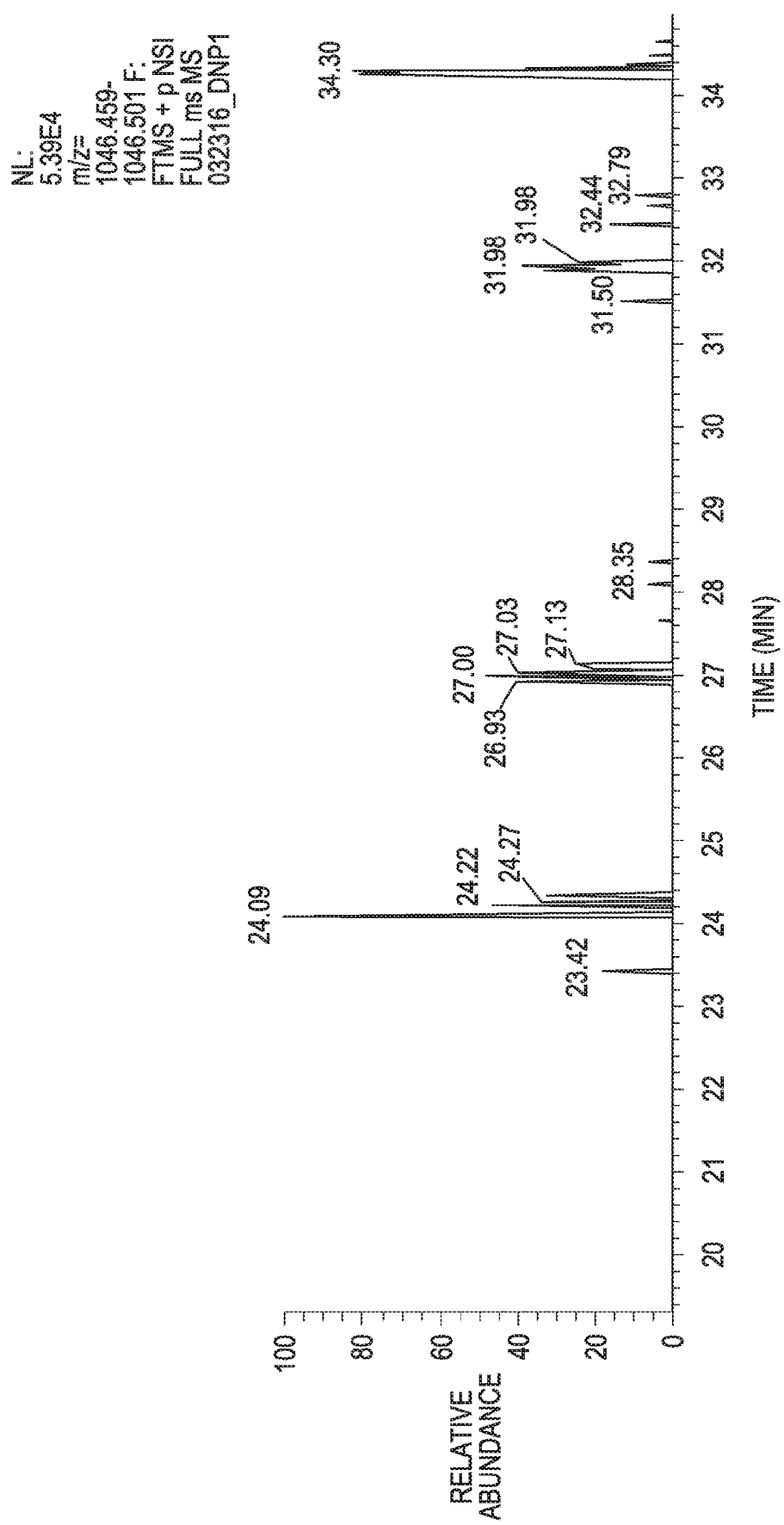
Figure 36C:
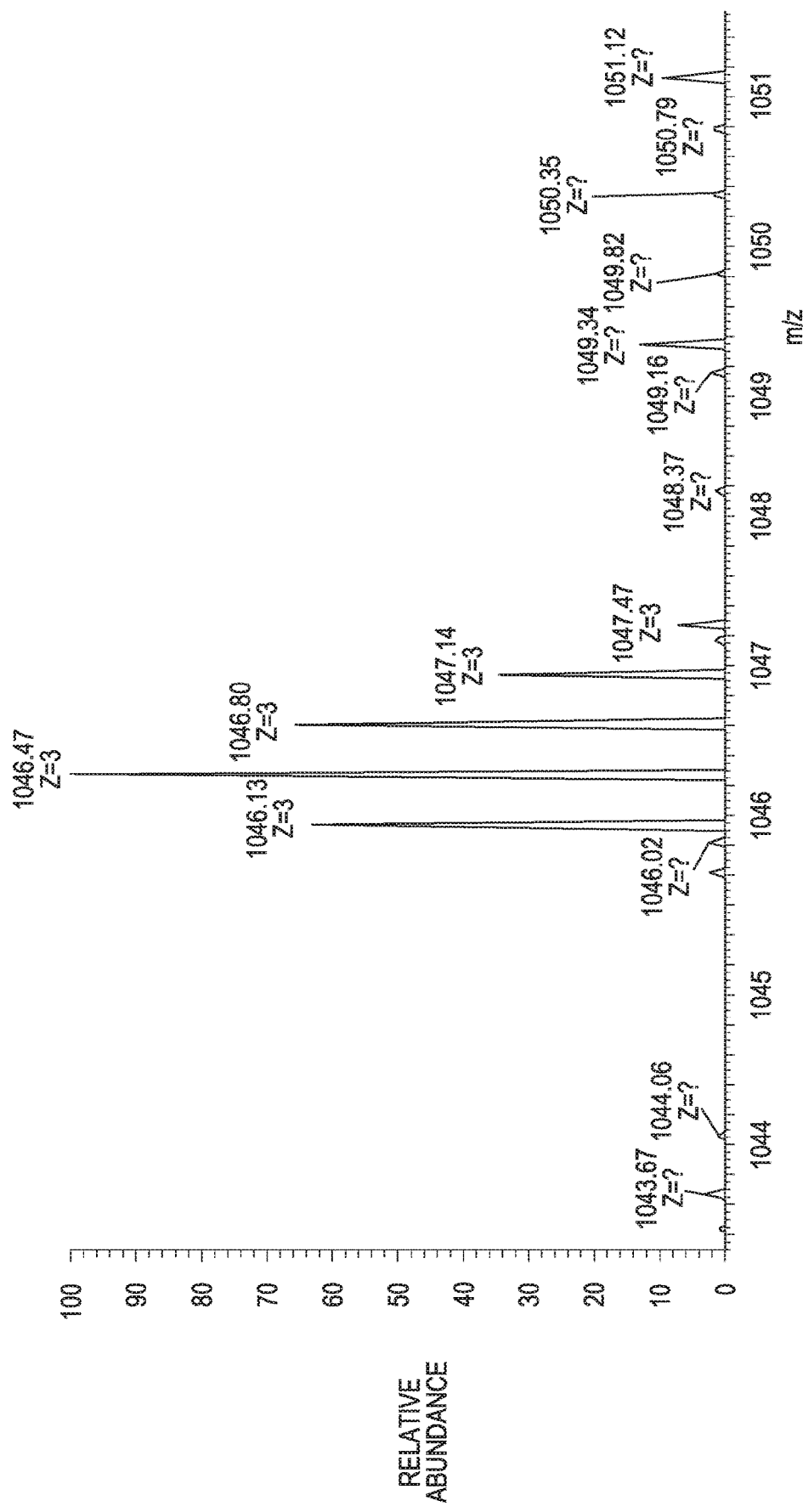
Figure 37A:
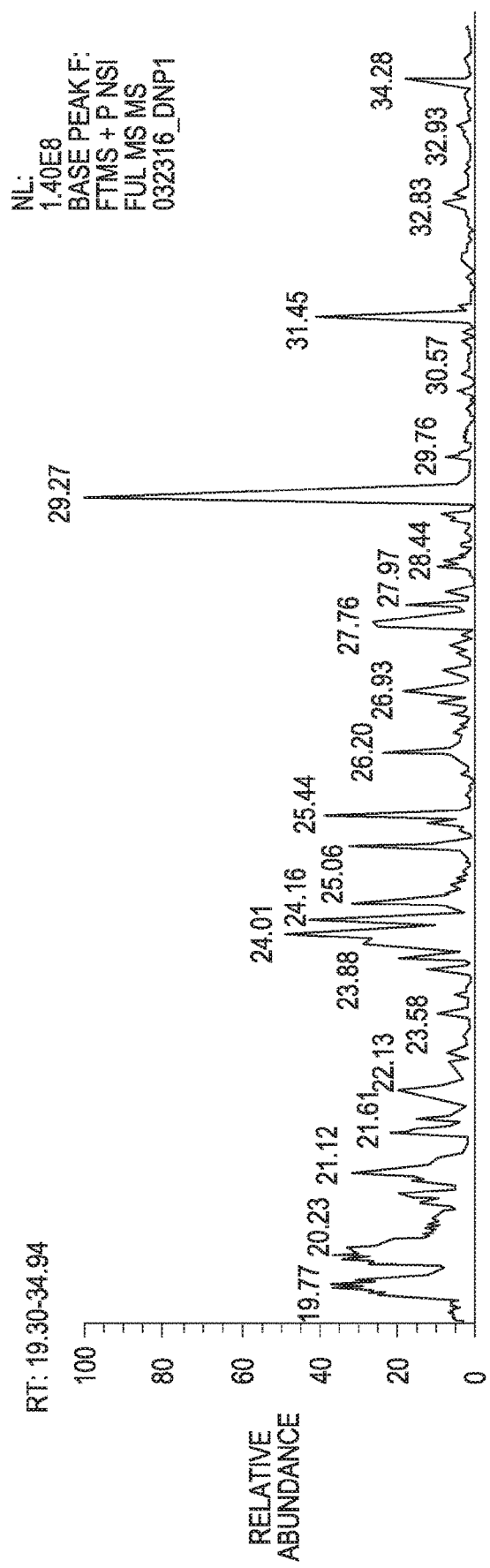
FIG. 37A-37C. MS-MS Result for conjugated SPE-7 IgE (24-40) Band 3 (+cHBL)—ASGYTFTSYWMHWVKQR (SEQ ID NO: 4)—MW=3419.56 Da, [M+2H]/2=1711.77. Confirmed the presence of peptide ASGYTFT-SYWMHWVKQR (SEQ ID NO: 4) +DNP from conjugated band 3 after de-staining and trypsinizing with the presence of a doubly charged peak of 1711.77 m/z at a retention time of 28 mins. Chromatogram given in (A) for all peak, (B) for peptide of interest and MS result give in (C) at specified retention time.
Figure 37B:
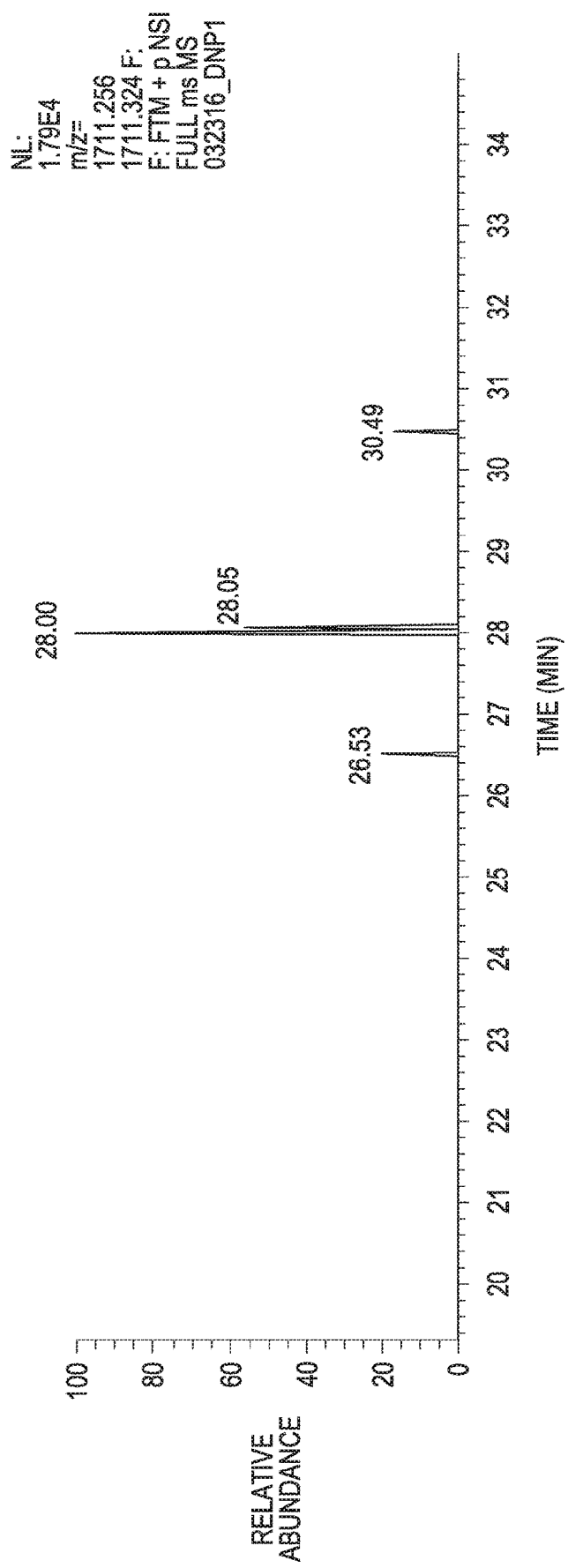
Figure 37C:
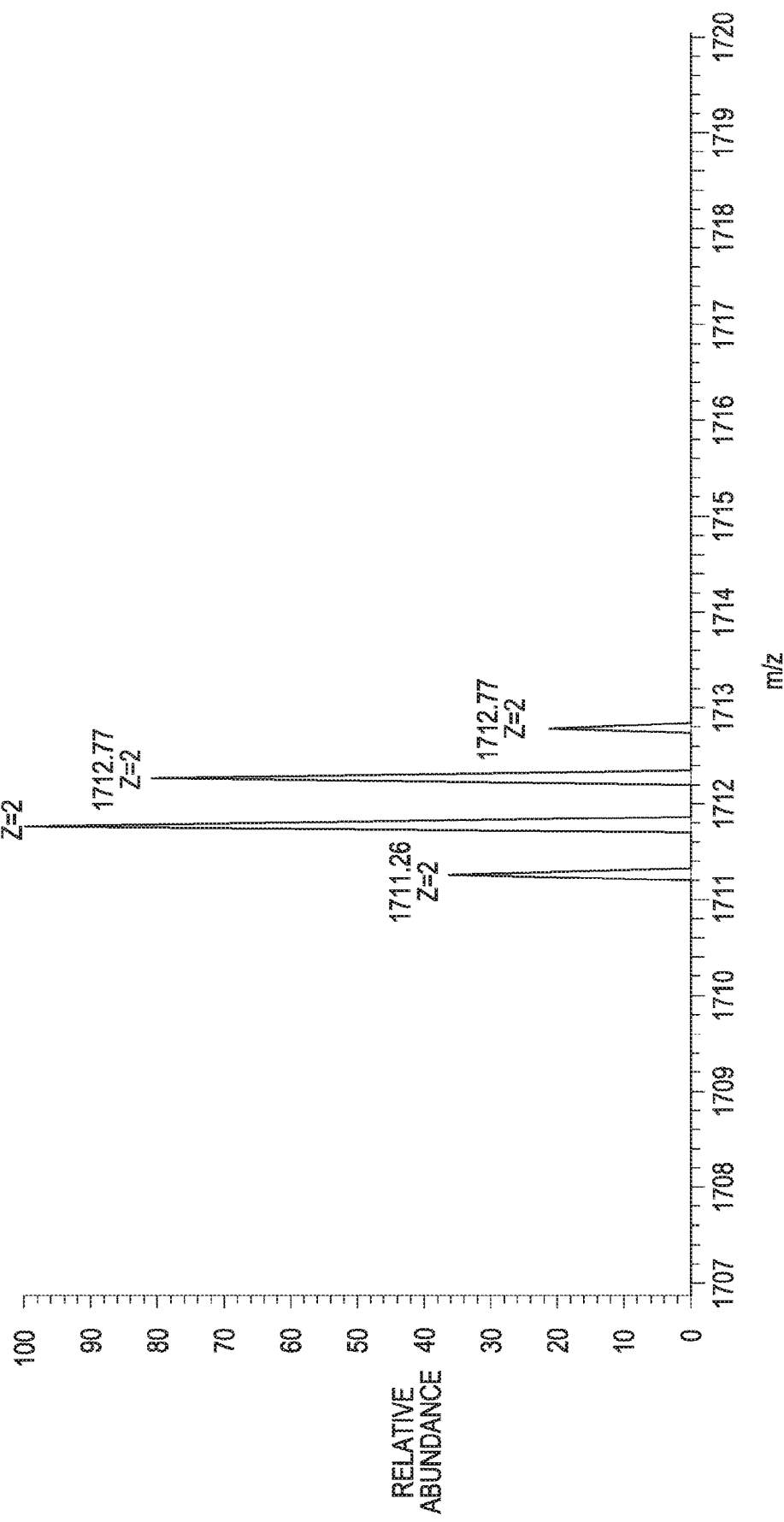
Figure 38A:
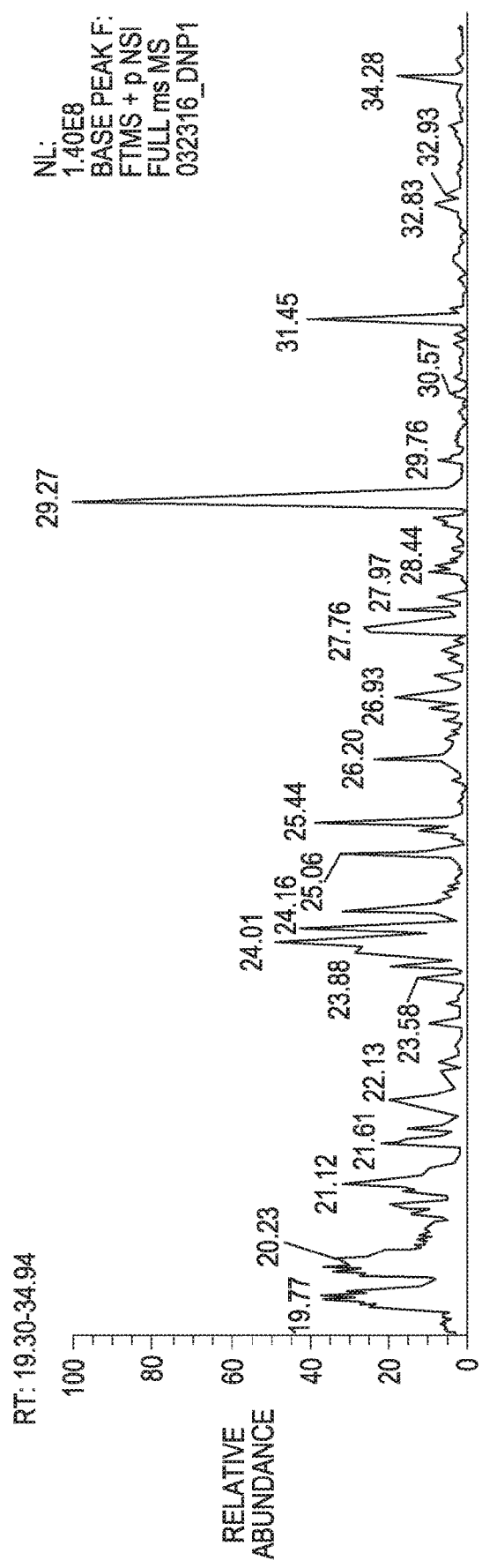
FIG. 38A-38C. MS-MS Result for conjugated SPE-7 IgE (24-40) Band 3 (+cHBL)—ASGYTFTSYWMHWVKQR (SEQ ID NO: 4)—MW=3419.56 Da, [M+3H]/3=1141.50. Confirmed the presence of peptide ASGYTFT-SYWMHWVKQR (SEQ ID NO: 4)+DNP from conjugated band 3 after destaining and trypsinizing with the presence of a triply charged peak of 1141.51 m/z at a retention time of 28 mins. Chromatogram given in (A) for all peak, (B) for peptide of interest and MS result give in (C) at specified retention time.
Figure 38B:
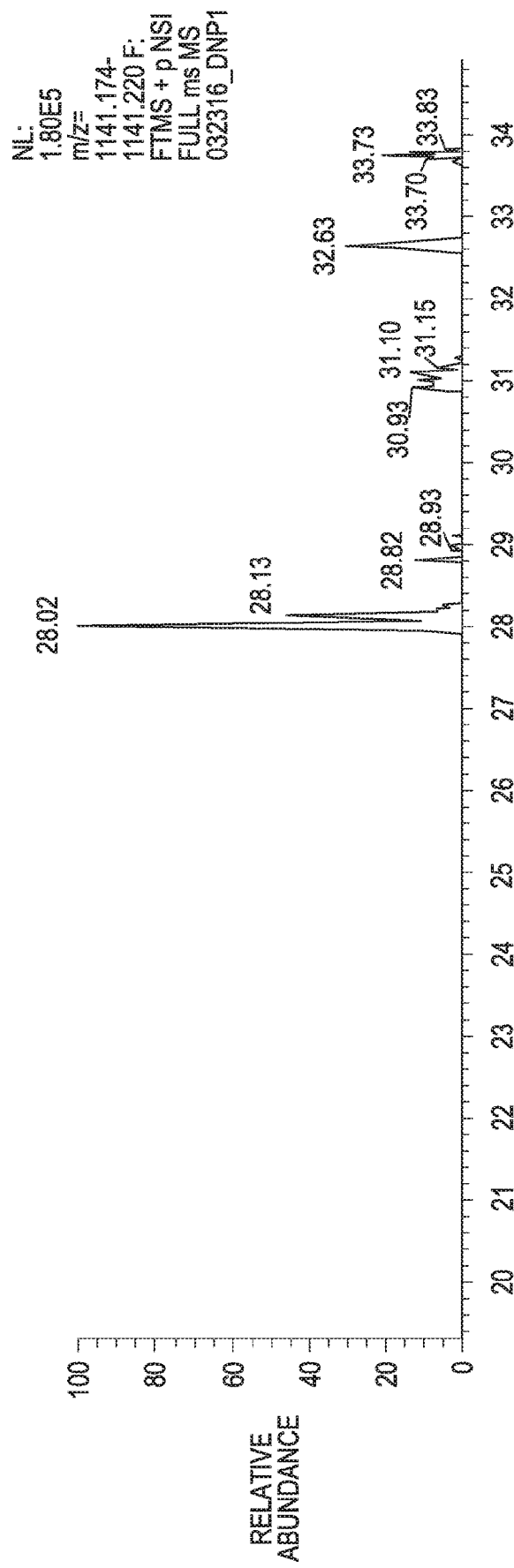
Figure 38C:
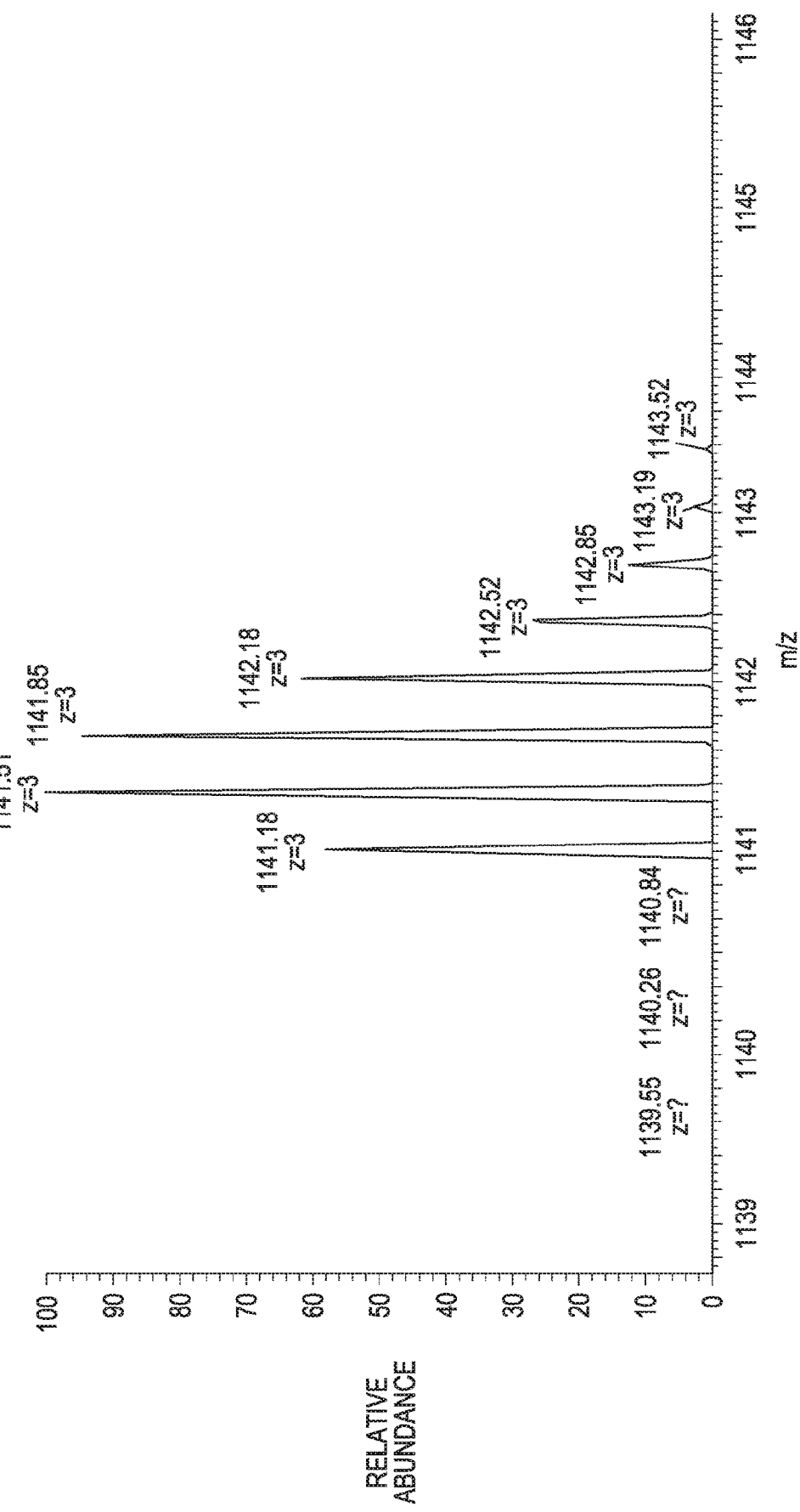
Figure 39A:
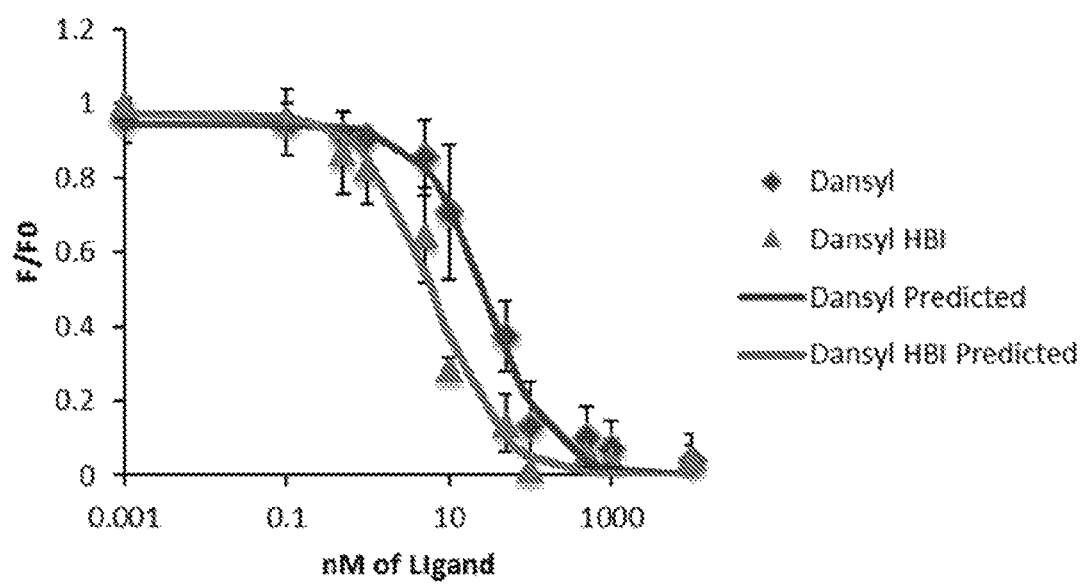
FIG. 39A-39B. Fluorescence quenching binding results for dansyl and penicilloyl HBI's. IgE$^{dansyl}$ was used in (A) and IgE$^{Penicillin}$ was used in (B).
Figure 39B:
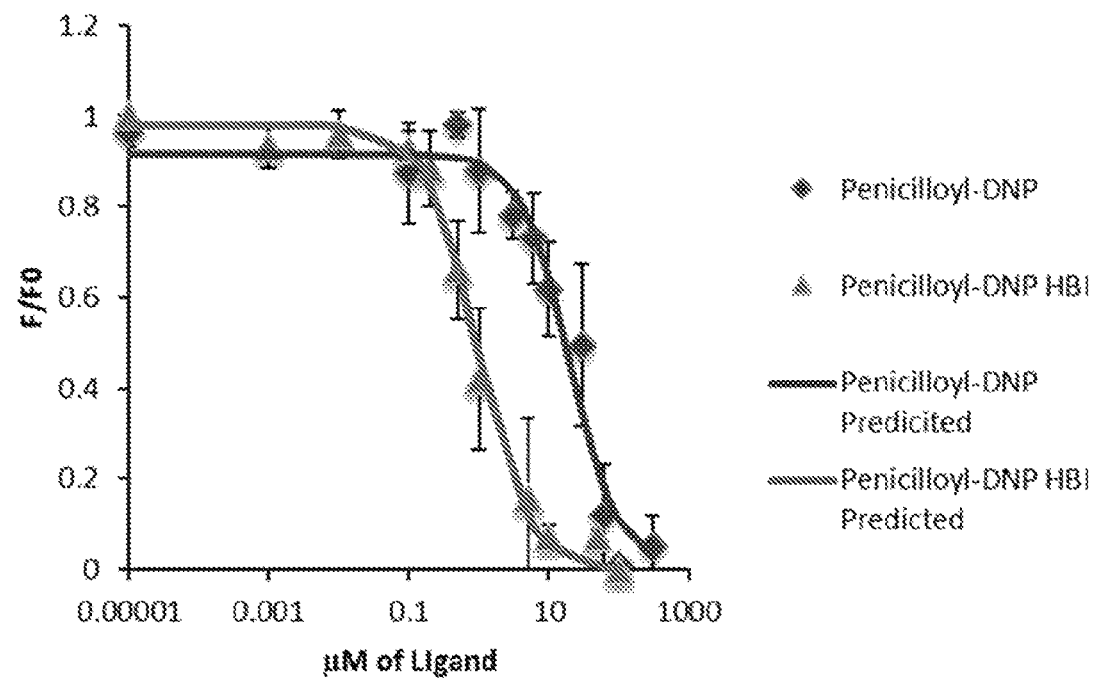
Figure 40:
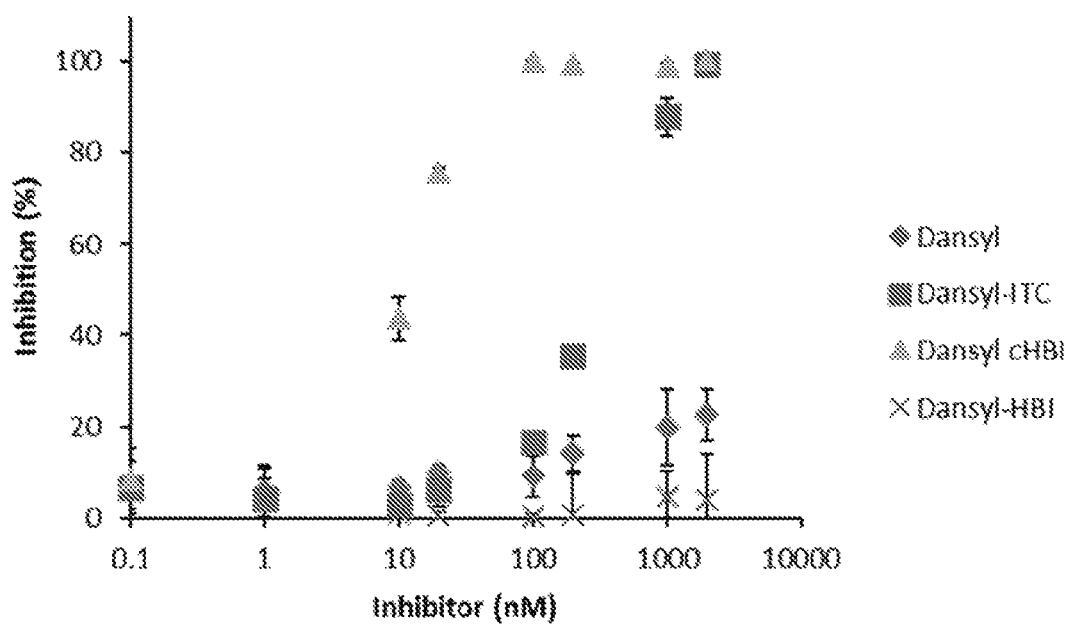
FIG. 40. Degranulation triggered with 1000 ng/mL dansyl-BSA after a 16-hour incubation with inhibitor molecules.
Figure 41:
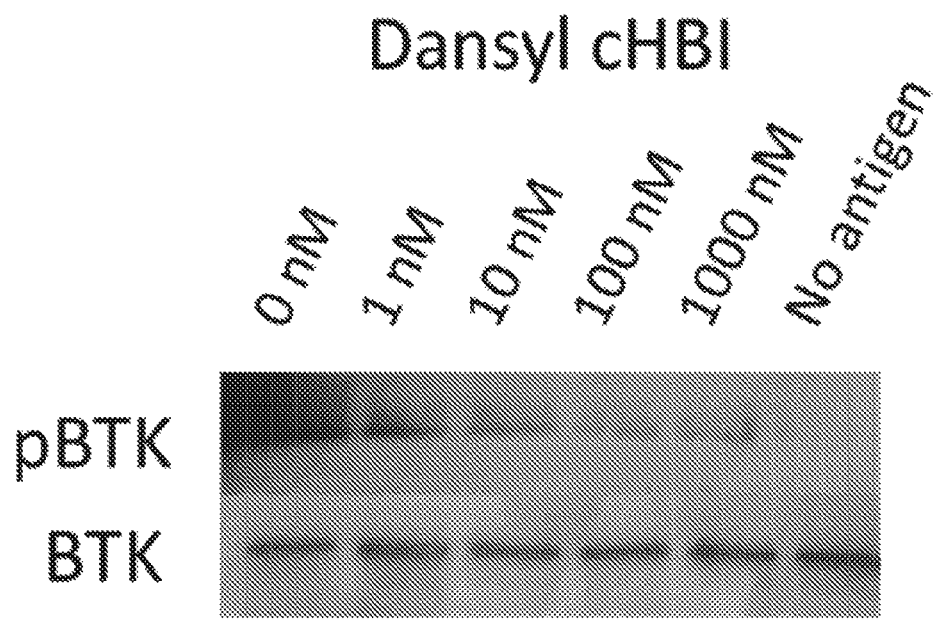
FIG. 41. Western blot of RBL cell lysates after 5-hour incubation with dansyl cHBIs. Degranulation was triggered with 1 µg/mL of dansyl-BSA prior to lysis and probing with anti-BTK or anti-pBTK antibodies.
Figure 42:
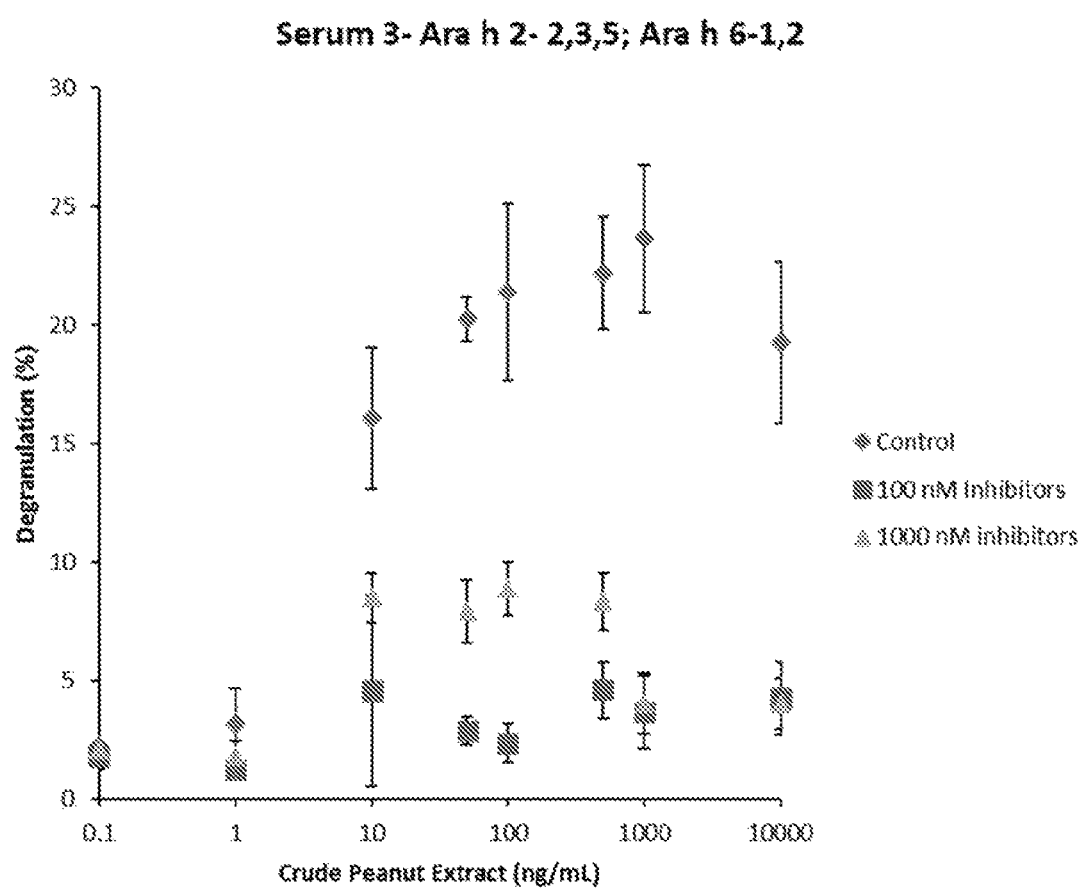
FIG. 42. Inhibition of crude peanut extract degranulation with RBL-SX38 cells sensitized with patient serum (serum 3) and incubated overnight with equimolar combination of ara h 2 peptide 2, 3, and 5 and ara h 6 peptide 1 and 2 inhibitors.
Figure 43:
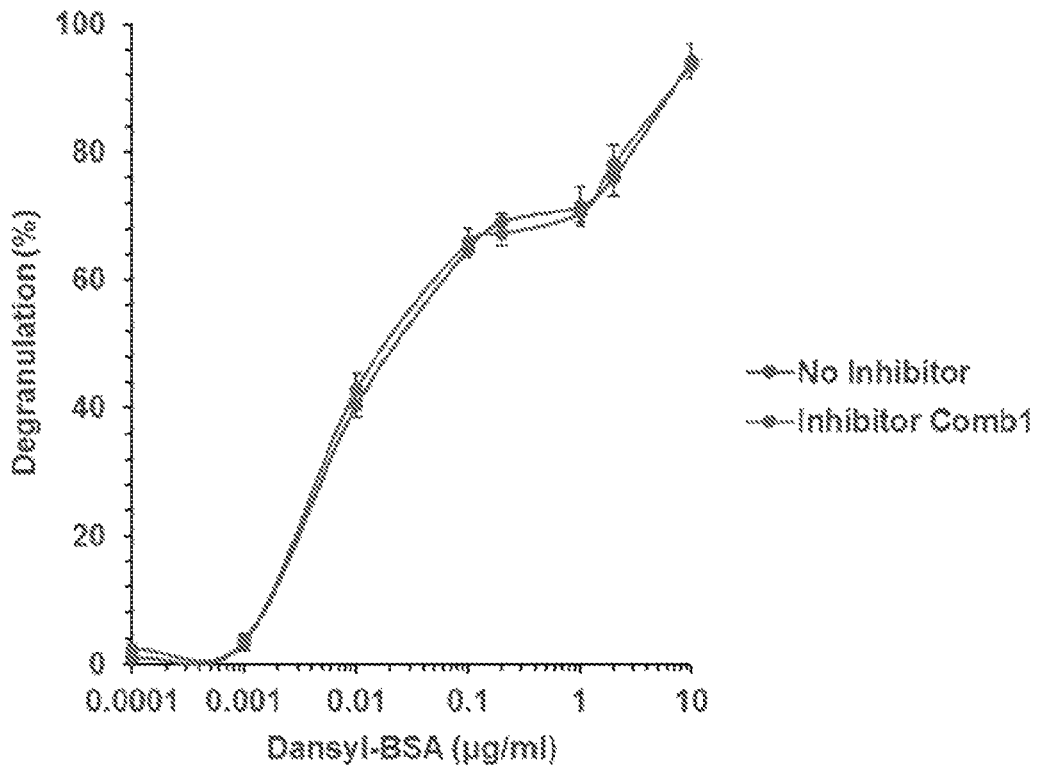
FIG. 43. 1000 nM of ara h 2 epitope 13 and ara h 6 epitope 10 combination was given to RBL-2H3 cells primed with an anti-dansyl IgE and then challenged with dansyl-BSA. These inhibitors do no disrupt degranulation to other compounds.
Figure 44:
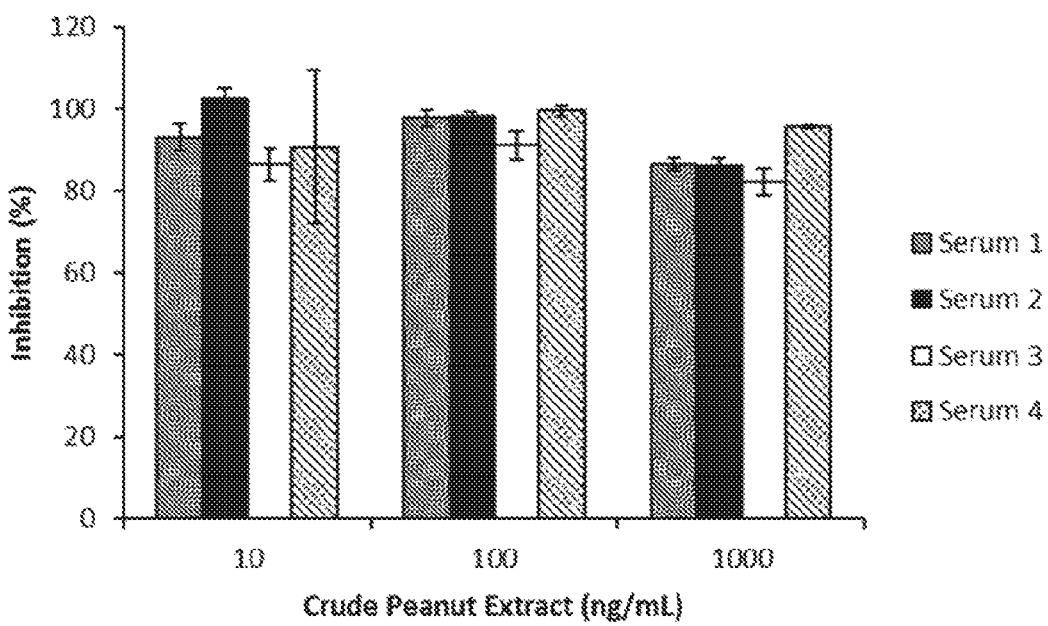
FIG. 44. Inhibition of CPE degranulation of RBL cell sensitized with patient serum. Inhibitor was a 1000 nM mixture of ara h 2 peptide 13 and ara h 6 peptide 10 inhibitors, 1:1 mixture incubated overnight.
Figure 46:
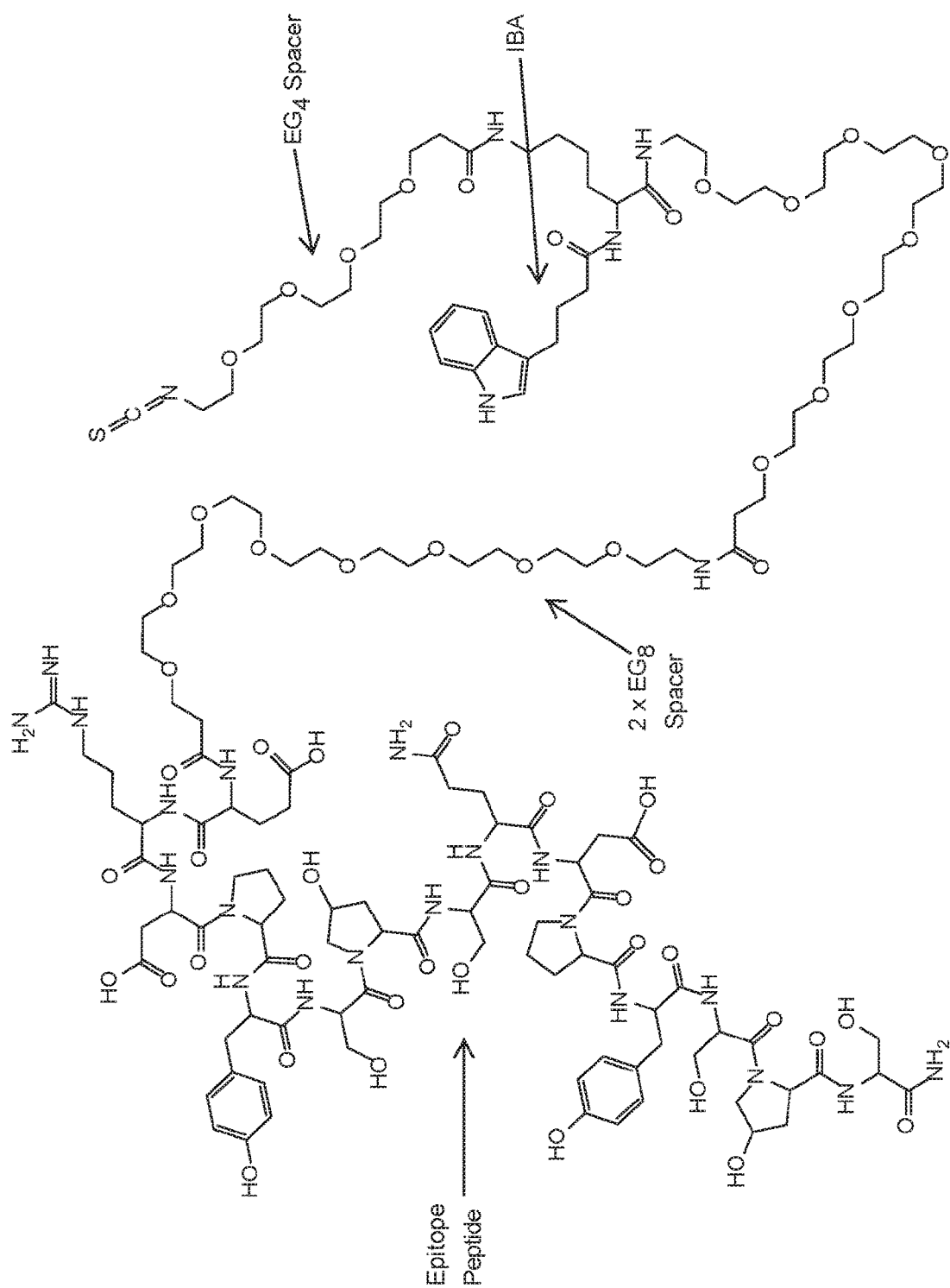
FIG. 46. Design of cHBI for peanut inhibitors. Note that epitope peptide can be replaced with any epitope from peanut proteins.

In conclusion, we have presented a versatile, effective and selective design for inhibitors to drug induced type I hypersensitivity basophil and mast cell degranulation. These cHBI molecules are potent and selective due to their ability to form specific covalent bonds with lysine side chains near the NBS site of antibodies, effectively permanently preventing hapten specific IgEs from participating in IgE crosslinking and degranulation of basophils and mast cells. Typically, inhibiting IgE crosslinking and degranulation responses to hapenized serum proteins is very challenging due to multiple hapten groups on serum proteins facilitating bivalent binding on single IgE molecules, greatly increasing the apparent avidity of the IgE-hapten complexes. These complexes are very stable and not inhibited by monovalent hapten molecules alone. We overcome this issue by tethering a hapten molecule to a lysine near the ABS, resulting in a large increase in effective concentration of competitive inhibitor which can effectively out-compete haptenized serum proteins for the same binding site. The innovative design of cHBIs makes them very effective and selective. As we have demonstrated in this manuscript, these inhibitors form off target covalent interactions slowly and utilize specific bivalent binding to both ABS and NBS to facilitate a covalent linkage only to the immunoreactive antibodies of interest (FIG. 31). Likewise, these inhibitors selectively inhibit degranulation to only the targeted hapten of interest in vitro (FIG. 32 and FIG. 34).

These inhibitors can be long lasting in a clinical setting as their inhibitory characteristics should persist throughout the course of a mast cell or basophil lifetime, which can be around a month in tissues but shorter in circulating basophils. We were able to demonstrate that these inhibitors completely inhibit hapten-BSA induced responses over the course of at least 72 hours (FIG. 32C). We demonstrated that cHBIs bind specifically to their target IgEs and prevent cellular degranulation to drug haptenized proteins both in vitro and in vivo. While we demonstrate the effectiveness to two hapten specific cHBIs, dansyl and penicillin, this design could be modified to accommodate any drug compound such as other penicillin derivatives, sulfa drugs or chemotherapeutics.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. An antibody inhibitor of Formula III:

$$
\begin{array}{c}
\text{FG} \\
| \\
\text{EG}^2-\text{K}^2-\text{TM}-\text{EG}^1-\text{K}^1-\text{EG}^1 \\
| \qquad\qquad\qquad | \\
\text{TG} \qquad\qquad \text{EG}^2-\text{TL}
\end{array}
\quad (\text{III})
$$

wherein
- TM is a targeting moiety for an antigen binding site (ABS) wherein the targeting moiety comprises a) an Ara h 2 allergen protein epitope ERDPYSPSQDPYSPS (SEQ ID NO: 6), b) a peptide WPRWLEN (SEQ ID NO: 1) or LLGPYELWELSH (SEQ ID NO: 2), or c) a penicillin G hapten, each which have a selective electrostatic affinity for the ABS of an immunoglobulin;
- TL is a targeting ligand for a conserved nucleotide binding site (NBS) of the immunoglobulin wherein the targeting ligand comprises indole-3-butyric acid (IBA) or 2-napthaleneacetic acid (NAA) and IBA or NAA has a selective electrostatic affinity for the NBS located proximal to the ABS and between the heavy chain and light chain of the immunoglobulin;
- FG is a reactive functional group capable of forming a site-directed covalent bond to the amine moiety of a lysine proximal to the NBS of an allergen reactive immunoglobulin;
- EG$^1$ is a variable length spacer comprising one or more spacers of the formula —(CH$_2$—X—CH$_2$CH$_2$—X—CH$_2$)$_y$— wherein the —(CH$_2$—X—CH$_2$CH$_2$—X—CH$_2$)$_y$— spacer is linked to one or more K$^1$ spacers;
- y is 1 to 12;
- X is O or NR wherein R is H or (C$_1$-C$_4$) alkyl;
- K$^1$ is a spacer comprising one or more lysine moieties;
- EG$^2$ is an optional variable length spacer comprising the formula —(CH$_2$—X—CH$_2$CH$_2$—X—CH$_2$)$_y$—;
- K$^2$ is an optional spacer comprising a lysine moiety;
- wherein the spacers EG$^1$, EG$^2$, K$^1$, K$^2$, and —(CH$_2$—X—CH$_2$CH$_2$—X—CH$_2$)$_y$— are linked by one or more amide bonds; and
- TG is an optional tag comprising a chromophore or a fluorophore;
- wherein the ABS targeting moiety (TM), the NBS targeting ligand (TL), and the reactive functional group (FG) are conjugated to K$^1$, EG$^1$ and EG$^2$, and TM is further conjugated to an optional tag (TG) by K$^2$ and EG$^2$, wherein when the antibody inhibitor bivalently binds to both the ABS and the NBS, the effective concentration of the reactive functional group (FG) near the amino acid of the immunoglobulin increases to irreversibly inhibit the immunoglobulin by the site-directed covalent bond formed by the inhibitor, and the irreversibly inhibited immunoglobulin is tagged by the chromophore or the fluorophore when the inhibitor contains TG.

2. The inhibitor of claim 1 wherein bivalent binding of TM and TL to the immunoglobulin synergistically enhance the avidity of the inhibitor.

3. The inhibitor of claim 1 wherein FG comprises a conjugate of isothiocyanate.

4. The inhibitor of claim 1 wherein the inhibitor is:
wherein Peptide is LLGPYELWELSH (SEQ ID NO: 2);

wherein Peptide is WPRWLEN (SEQ ID NO: 1);

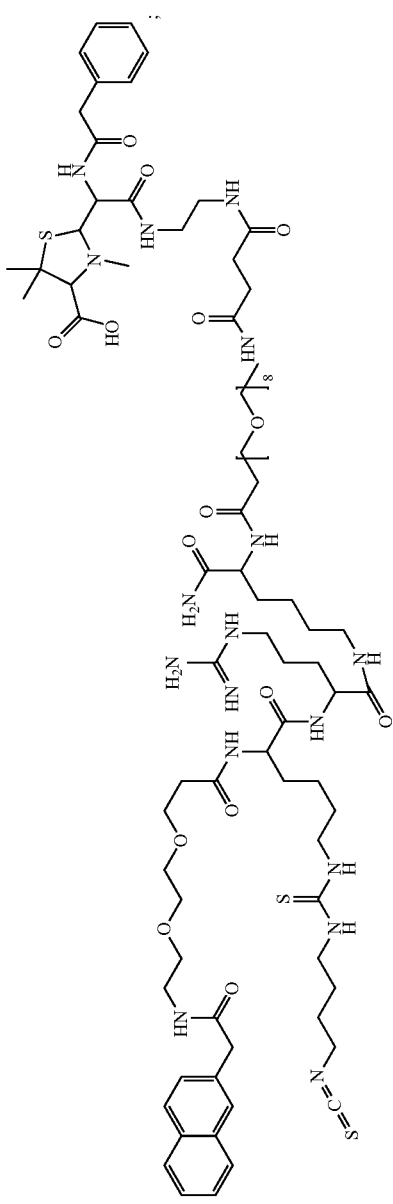
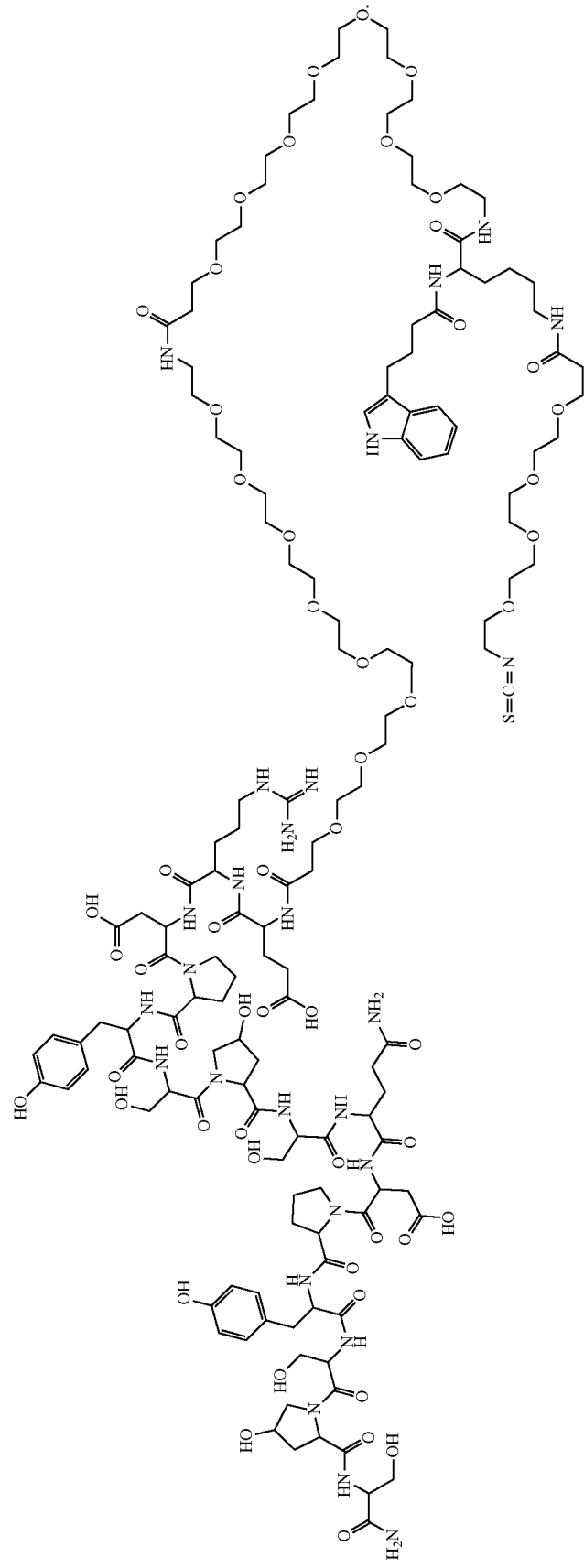

5. The inhibitor of claim 1 wherein TL comprises a conjugate of a ligand which electrostatically binds to NBS with a $K_d$ of less than 5 μM.

6. The inhibitor of claim 1 wherein FG comprises a conjugate of an isothiocyanate, an isocyanate, an alkyne, a bromine, an acrylamide, or a maleimide.

7. The inhibitor of claim 1 wherein X is O.

8. The inhibitor of claim 1 wherein the inhibitor is

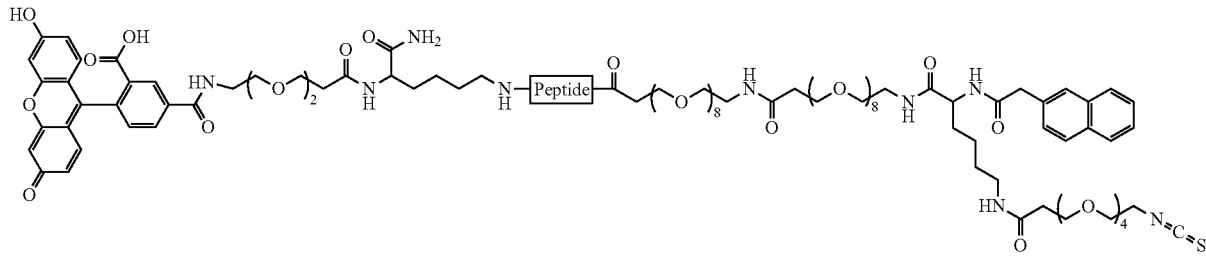

wherein Peptide is WPRWLEN (SEQ ID NO: 1) or LLGPYELWELSH (SEQ ID NO: 2).

9. A covalent heterobivalent inhibitor wherein the inhibitor is:

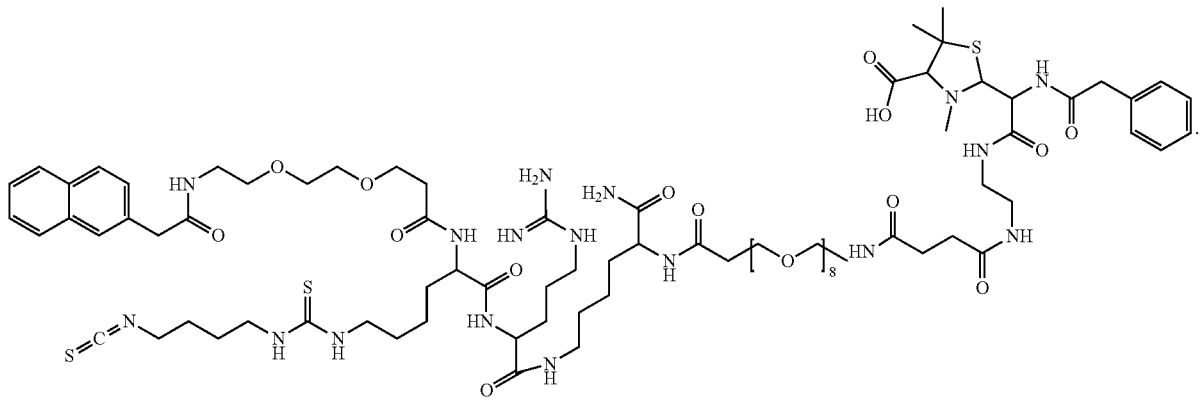

10. An inhibitor wherein the inhibitor is:

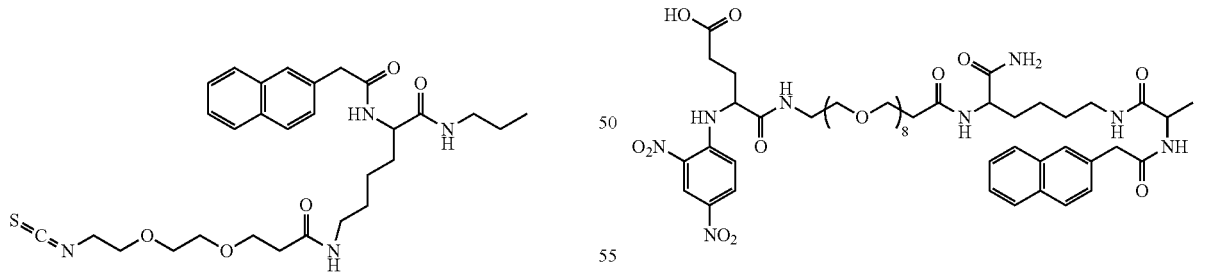

-continued

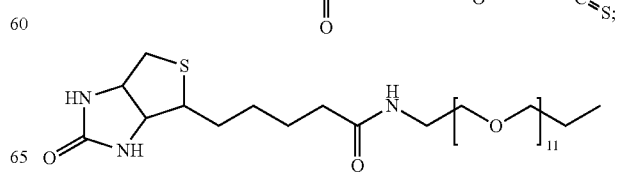

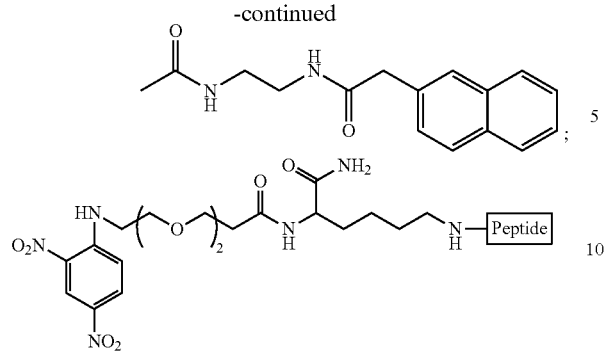
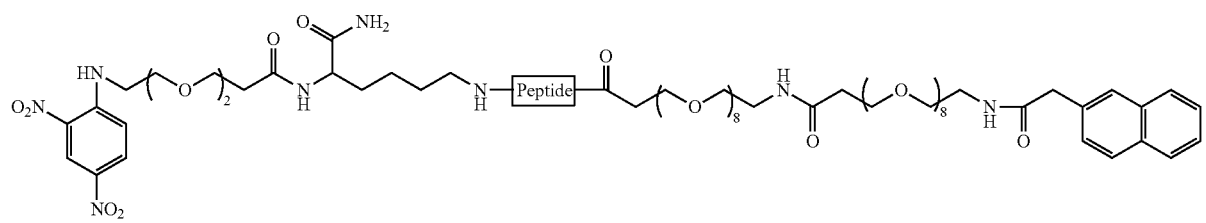
wherein Peptide is LLGPYELWELSH (SEQ ID NO: 2);
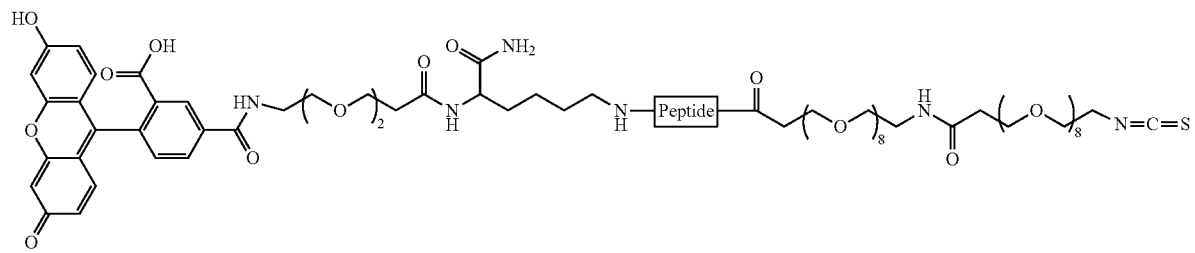
wherein Peptide is LLGPYELWELSH (SEQ ID NO: 2);
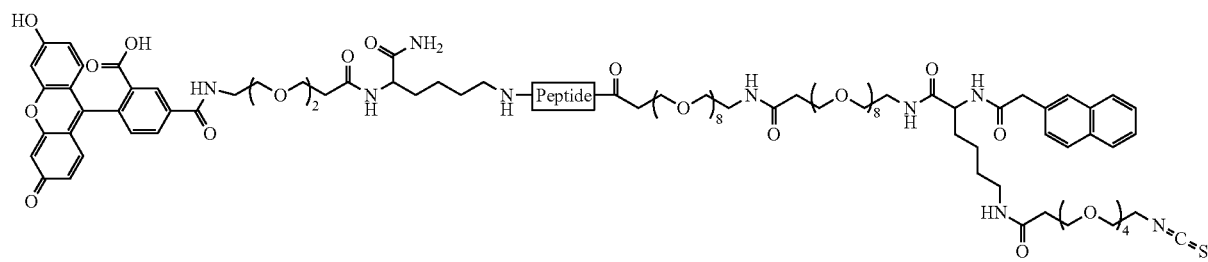
wherein Peptide is WPRWLEN (SEQ ID NO: 1) or LLGPYELWELSH (SEQ ID NO: 2);

91
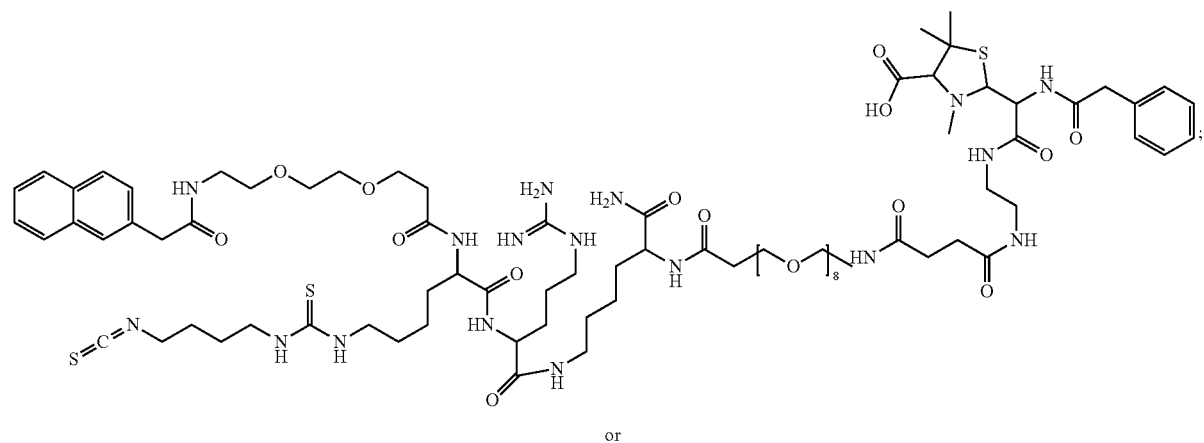
or
92
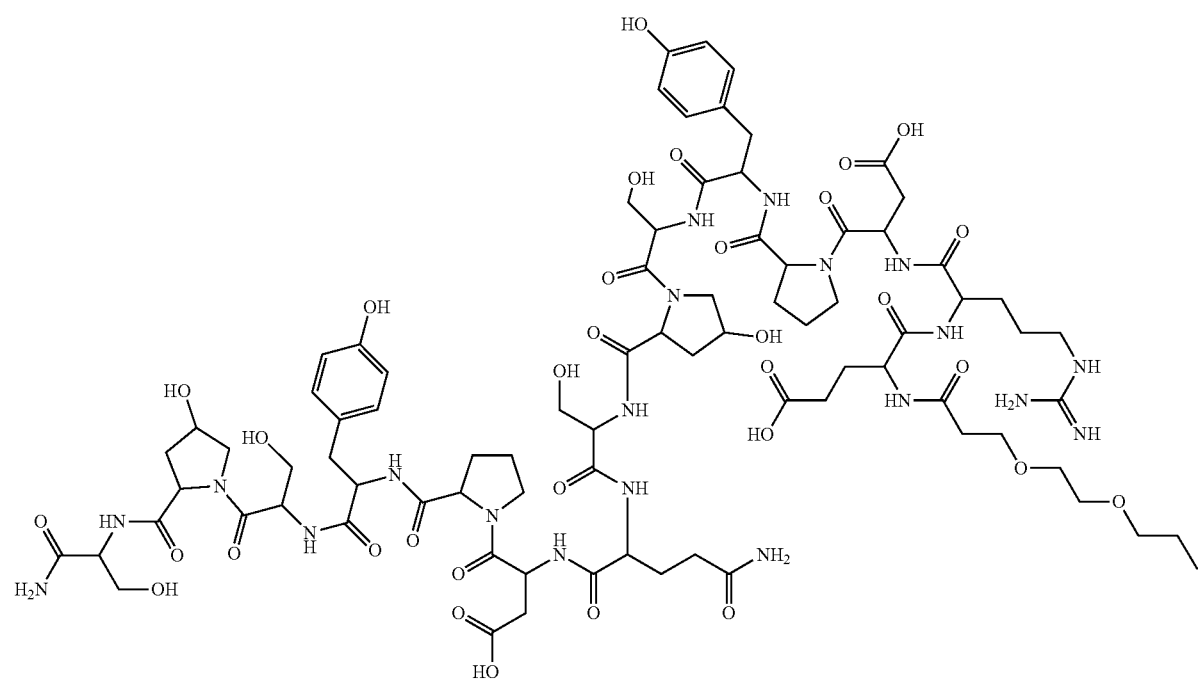

-continued

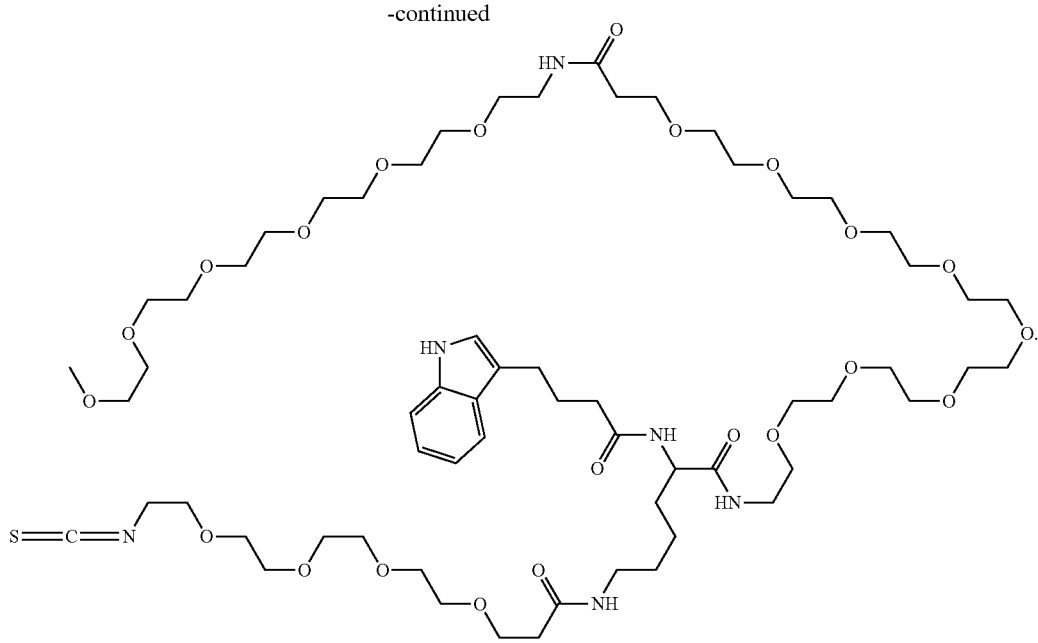

11. A method of inhibiting or reducing the severity of an allergic reaction comprising administering an effective amount of one of the inhibitor of claim 1 to a subject a) prior to exposure of the subject to an allergen, b) after exposure of the subject to an allergen, c) during an allergic response of the subject to an allergen, or d) prior to immunotherapy desensitization of a subject requiring immunotherapy desensitization, wherein inhibition of the immunoglobulin antibody to the allergen prevents degranulation of mast cells and basophils thereby substantially inhibiting or reducing lowering the allergic response of the subject to the allergen.

12. The method of claim 11 wherein the inhibitor is co-administered with epinephrine to mitigate an anaphylaxis response in a subject exposed to an allergen.

* * * * *

SEQUENCE LISTING

<160> NUMBER OF SEQ ID NOS: 42

<210> SEQ ID NO 1
<211> LENGTH: 7
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 1

Trp Pro Arg Trp Leu Glu Asn
1               5

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Leu Leu Gly Pro Tyr Glu Leu Trp Glu Leu Ser His
1               5                   10

<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Ser Gly Tyr Thr Phe Thr Ser Tyr Trp Met His Trp Val Lys
1               5                   10                  15

<210> SEQ ID NO 4
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ala Ser Gly Tyr Thr Phe Thr Ser Tyr Trp Met His Trp Val Lys Gln
1               5                   10                  15

Arg

<210> SEQ ID NO 5
<211> LENGTH: 16
<212> TYPE: PRT
<213> ORGANISM: Arachis hypogaea

<400> SEQUENCE: 5

Asn Leu Arg Pro Cys Glu Gln His Leu Met Gln Lys Ile Gln Arg Asp
1               5                   10                  15

<210> SEQ ID NO 6
<211> LENGTH: 15
<212> TYPE: PRT
<213> ORGANISM: Arachis hypogaea

<400> SEQUENCE: 6

Glu Arg Asp Pro Tyr Ser Pro Ser Gln Asp Pro Tyr Ser Pro Ser
1               5                   10                  15

<210> SEQ ID NO 7
<211> LENGTH: 9
<212> TYPE: PRT
```

```
<213> ORGANISM: Arachis hypogaea

<400> SEQUENCE: 7

Ser Asp Arg Leu Gln Gly Arg Gln Gln
1               5

<210> SEQ ID NO 8
<211> LENGTH: 9
<212> TYPE: PRT
<213> ORGANISM: Arachis hypogaea

<400> SEQUENCE: 8

Arg Arg Cys Gln Ser Gln Leu Glu Arg
1               5

<210> SEQ ID NO 9
<211> LENGTH: 10
<212> TYPE: PRT
<213> ORGANISM: Arachis hypogaea

<400> SEQUENCE: 9

His Ala Ser Ala Arg Gln Gln Trp Glu Leu
1               5                   10

<210> SEQ ID NO 10
<211> LENGTH: 17
<212> TYPE: PRT
<213> ORGANISM: Arachis hypogaea

<400> SEQUENCE: 10

Arg Gln Gln Glu Gln Gln Phe Lys Arg Glu Leu Arg Asn Leu Pro Gln
1               5                   10                  15

Gln

<210> SEQ ID NO 11
<211> LENGTH: 7
<212> TYPE: PRT
<213> ORGANISM: Arachis hypogaea

<400> SEQUENCE: 11

Pro Gln Arg Cys Asp Leu Glu
1               5

<210> SEQ ID NO 12
<211> LENGTH: 13
<212> TYPE: PRT
<213> ORGANISM: Arachis hypogaea

<400> SEQUENCE: 12

Cys Asp Leu Glu Val Glu Ser Gly Gly Arg Asp Arg Tyr
1               5                   10

<210> SEQ ID NO 13
<211> LENGTH: 13
<212> TYPE: PRT
<213> ORGANISM: Arachis hypogaea

<400> SEQUENCE: 13

Cys Glu Ala Leu Gln Gln Ile Met Glu Asn Gln Ser Asp
1               5                   10

<210> SEQ ID NO 14
<211> LENGTH: 12
<212> TYPE: PRT
```

```
<213> ORGANISM: Arachis hypogaea

<400> SEQUENCE: 14

Cys Asn Glu Leu Asn Glu Phe Glu Asn Asn Gln Arg
1               5                   10

<210> SEQ ID NO 15
<211> LENGTH: 12
<212> TYPE: PRT
<213> ORGANISM: Arachis hypogaea

<400> SEQUENCE: 15

Pro Arg Pro Cys Glu Gln His Leu Met Gln Lys Ile
1               5                   10

<210> SEQ ID NO 16
<211> LENGTH: 16
<212> TYPE: PRT
<213> ORGANISM: Arachis hypogaea

<400> SEQUENCE: 16

Glu Leu Gln Gly Asp Arg Arg Cys Gln Ser Gln Leu Glu Arg Ala
1               5                   10                  15

<210> SEQ ID NO 17
<211> LENGTH: 14
<212> TYPE: PRT
<213> ORGANISM: Arachis hypogaea

<400> SEQUENCE: 17

Asp Pro Tyr Ser Pro Ser Asp Arg Arg Gly Ala Gly Ser Ser
1               5                   10

<210> SEQ ID NO 18
<211> LENGTH: 14
<212> TYPE: PRT
<213> ORGANISM: Arachis hypogaea

<400> SEQUENCE: 18

Met Arg Arg Glu Arg Gly Arg Gly Gln Asp Ser Ser Ser Ser
1               5                   10

<210> SEQ ID NO 19
<211> LENGTH: 11
<212> TYPE: PRT
<213> ORGANISM: Arachis hypogaea

<400> SEQUENCE: 19

Lys Pro Cys Glu Gln His Ile Met Gln Arg Ile
1               5                   10

<210> SEQ ID NO 20
<211> LENGTH: 7
<212> TYPE: PRT
<213> ORGANISM: Arachis hypogaea

<400> SEQUENCE: 20

Tyr Asp Ser Tyr Asp Ile Arg
1               5

<210> SEQ ID NO 21
<211> LENGTH: 12
<212> TYPE: PRT
<213> ORGANISM: Arachis hypogaea
```

```
<400> SEQUENCE: 21

Cys Asp Glu Leu Asn Glu Met Glu Asn Thr Gln Arg
1               5                   10

<210> SEQ ID NO 22
<211> LENGTH: 13
<212> TYPE: PRT
<213> ORGANISM: Arachis hypogaea

<400> SEQUENCE: 22

Cys Glu Ala Leu Gln Gln Ile Met Glu Asn Gln Cys Asp
1               5                   10

<210> SEQ ID NO 23
<211> LENGTH: 10
<212> TYPE: PRT
<213> ORGANISM: Arachis hypogaea

<400> SEQUENCE: 23

Lys Arg Glu Leu Arg Met Leu Pro Gln Gln
1               5                   10

<210> SEQ ID NO 24
<211> LENGTH: 13
<212> TYPE: PRT
<213> ORGANISM: Arachis hypogaea

<400> SEQUENCE: 24

Cys Asn Phe Arg Ala Pro Gln Arg Cys Asp Leu Asp Val
1               5                   10

<210> SEQ ID NO 25
<211> LENGTH: 19
<212> TYPE: PRT
<213> ORGANISM: Arachis hypogaea

<400> SEQUENCE: 25

Gly Glu Gln Glu Gln Tyr Asp Ser Tyr Asn Phe Gly Ser Thr Arg Ser
1               5                   10                  15

Ser Asp Gln

<210> SEQ ID NO 26
<211> LENGTH: 4
<212> TYPE: PRT
<213> ORGANISM: Arachis hypogaea

<400> SEQUENCE: 26

Gln Asp Arg Gln
1

<210> SEQ ID NO 27
<211> LENGTH: 7
<212> TYPE: PRT
<213> ORGANISM: Arachis hypogaea

<400> SEQUENCE: 27

Ser Cys Glu Arg Gln Val Asp
1               5

<210> SEQ ID NO 28
<211> LENGTH: 12
<212> TYPE: PRT
<213> ORGANISM: Arachis hypogaea
```

```
<400> SEQUENCE: 28

Ile Arg Ser Thr Arg Ser Ser Asp Gln Gln Arg
1               5                   10

<210> SEQ ID NO 29
<211> LENGTH: 6
<212> TYPE: PRT
<213> ORGANISM: Arachis hypogaea

<400> SEQUENCE: 29

Gln Asp Arg Gln Met Val
1               5

<210> SEQ ID NO 30
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ala Ser Gly Tyr Thr Phe Thr Ser Tyr Trp Met His Trp Val Lys Gln
1               5                   10                  15

<210> SEQ ID NO 31
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ala Ser Gly Tyr Thr Phe Thr Ser Tyr Trp Met His Trp Val Lys Gln
1               5                   10                  15

Arg

<210> SEQ ID NO 32
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Ala Ser Gly Tyr Thr Phe Thr Ser Tyr Trp Met His Trp Val Lys Gln
1               5                   10                  15

Arg Arg

<210> SEQ ID NO 33
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ala Ser Gly Tyr Thr Phe Thr Ser Tyr Trp Met His Trp Val Lys Gln
1               5                   10                  15

Arg Arg Gly Arg
            20
```

<210> SEQ ID NO 34
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Glu Val Gln Leu Gln Gln Pro Gly Ala Glu Leu Val Lys
1               5                   10

<210> SEQ ID NO 35
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Glu Val Gln Leu Gln Gln Pro Gly Ala Glu Leu Val Lys Pro Gly Ala
1               5                   10                  15

Ser Val Lys

<210> SEQ ID NO 36
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Glu Val Gln Leu Gln Gln Pro Gly Ala Glu Leu Val Lys Pro Gly Ala
1               5                   10                  15

Ser Val Lys Leu Ser Cys Lys
            20

<210> SEQ ID NO 37
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Leu Ser Cys Lys
1

<210> SEQ ID NO 38
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Leu Ser Cys Lys Ala Ser Gly Tyr Thr Phe Thr Ser Tyr Trp Met His
1               5                   10                  15

Trp Val

<210> SEQ ID NO 39

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ile Asp Pro Asn Gly Gly Gly Thr Lys
1               5

<210> SEQ ID NO 40
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ile Asp Pro Asn Gly Gly Gly Thr Lys Tyr Asn Glu Lys
1               5                   10

<210> SEQ ID NO 41
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
                20                  25                  30

Asn Tyr Ala Asn Trp Val Gln Glu Lys Pro Asp His Leu Phe Thr Gly
            35                  40                  45

Leu Ile Gly Gly Thr Asn Asn Arg Ala Pro Gly Val Pro Ala Arg Phe
        50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

His Leu Val Glu Gly Gly Gly Thr Lys Leu Thr Val Leu Gly Gln Pro
            100                 105                 110

Lys Ser Ser Pro Ser Val Thr Leu Phe Pro Pro Ser Ser Glu Glu Leu
        115                 120                 125

Glu Thr Asn Lys Ala Thr Leu Val Cys Thr Ile Thr Asp Phe Tyr Pro
130                 135                 140

Gly Val Val Thr Val Asp Trp Lys Val Asp Gly Thr Pro Val Thr Gln
145                 150                 155                 160

Gly Met Glu Thr Thr Gln Pro Ser Lys Gln Ser Asn Asn Lys Tyr Met
                165                 170                 175

Ala Ser Ser Tyr Leu Thr Leu Thr Ala Gly Ala Trp Glu Arg His Asn
            180                 185                 190

Ser Tyr Ser Cys Gln Val Thr His Glu Gly His Thr Val Glu Lys Ser
        195                 200                 205

Leu Ser Arg Ala Asp Cys Ser
    210                 215
```

<210> SEQ ID NO 42
<211> LENGTH: 321
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 42

```
Glu Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Arg Gly Arg Gly Leu Glu Trp Ile
        35                  40                  45

Gly Arg Ile Asp Pro Asn Gly Gly Thr Lys Tyr Asn Glu Lys Phe
    50                  55                  60

Lys Ser Lys Ala Thr Leu Thr Val Asp Lys Pro Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Met Trp Tyr Tyr Gly Thr Tyr Tyr Phe Asp Tyr Trp Gly Gln
            100                 105                 110

Gly Thr Thr Leu Thr Val Ser Ser Ala Ser Ile Arg Asn Pro Ala Leu
        115                 120                 125

Tyr Pro Leu Lys Pro Cys Lys Gly Thr Ala Ser Met Thr Leu Gly Cys
    130                 135                 140

Leu Val Lys Asp Tyr Phe Pro Gly Pro Val Thr Val Thr Trp Tyr Ser
145                 150                 155                 160

Asp Ser Leu Asn Met Ser Thr Val Asn Phe Pro Ala Leu Gly Ser Glu
                165                 170                 175

Leu Lys Val Thr Thr Ser Gln Val Thr Ser Trp Gly Lys Ser Ala Lys
            180                 185                 190

Asn Phe Thr Cys His Cys Thr His Pro Pro Ser Phe Asn Glu Ser Arg
        195                 200                 205

Thr Ile Leu Val Arg Pro Val Asn Ile Thr Glu Pro Thr Leu Glu Leu
    210                 215                 220

Leu Trp Ser Ser Cys Asp Pro Asn Ala Phe Met Ser Thr Ile Gln Leu
225                 230                 235                 240

Tyr Cys Phe Ile Thr Gly His Ile Leu Asn Asp Val Ser Val Ser Trp
                245                 250                 255

Leu Met Asp Asp Arg Glu Ile Thr Asp Thr Leu Ala Gln Thr Val Leu
            260                 265                 270

Ile Lys Glu Glu Gly Lys Leu Ala Ser Thr Cys Ser Lys Leu Asn Ile
        275                 280                 285

Thr Glu Gln Gln Trp Met Ser Glu Ser Thr Phe Thr Cys Lys Val Thr
    290                 295                 300

Ser Gln Gly Val Asp Tyr Leu Ala His Thr Arg Arg Cys Pro Asp His
305                 310                 315                 320

Glu
```